(12) United States Patent
Purdum

(10) Patent No.: US 7,118,852 B2
(45) Date of Patent: Oct. 10, 2006

(54) METHODS AND APPARATUS FOR DECONTAMINATING FLUIDS

(75) Inventor: Howard E. Purdum, Alpharetta, GA (US)

(73) Assignee: Throwleigh Technologies, L.L.C., Ball Ground, GA (US)

( * ) Notice: Subject to any disclaimer, the term of this patent is extended or adjusted under 35 U.S.C. 154(b) by 432 days.

(21) Appl. No.: 10/119,907

(22) Filed: Apr. 11, 2002

(65) Prior Publication Data

US 2003/0194692 A1    Oct. 16, 2003

(51) Int. Cl.
*A01N 1/02* (2006.01)
*C12N 13/00* (2006.01)

(52) U.S. Cl. ........................... 435/2; 435/173.1
(58) Field of Classification Search ............ None
See application file for complete search history.

(56) References Cited

U.S. PATENT DOCUMENTS

| | | | | |
|---|---|---|---|---|
| 4,517,159 A | 5/1985 | Karlson | ................ | 422/20 |
| 4,632,980 A | 12/1986 | Zee et al. | ................ | 530/380 |
| 5,330,661 A | 7/1994 | Okuda et al. | ................ | 210/748 |
| 5,370,740 A | 12/1994 | Chao et al. | ................ | 134/1 |
| 5,401,237 A | 3/1995 | Tachibana et al. | ................ | 604/4 |
| 5,429,594 A | 7/1995 | Castle | ................ | 604/4 |
| 5,523,058 A | 6/1996 | Umemura et al. | ................ | 422/128 |
| 5,679,257 A | 10/1997 | Coate et al. | ................ | 210/695 |
| 5,997,812 A | 12/1999 | Burnham et al. | ................ | 422/24 |
| 6,083,387 A | 7/2000 | LeBlanc et al. | ................ | 210/199 |
| 6,802,892 B1 * | 10/2004 | Newman et al. | ................ | 96/156 |

FOREIGN PATENT DOCUMENTS

| | | |
|---|---|---|
| JP | 2000-325702 | 11/2000 |
| WO | WO 98/01394 | 1/1998 |

OTHER PUBLICATIONS

Zhu CP et al. "Sonochemical effects of . . . radiation". Chinese Science Bulletin, Jan. 2000, 45(2): 142-145. entire document.*
Burleson GR et al. "Inactivation of viruses and bacteria . . . without sonication". Applied Microbiology, Mar. 1975, 29(3): 340-344. entire document.*
Butterfield DA et al. "Structural and functional charges in proteins . . . and vitamin E". Ann. N. Y. Acad. Sci. 1998, 854: 448-62.*

* cited by examiner

*Primary Examiner*—Sandra E. Saucier
*Assistant Examiner*—Satyendra K. Singh
(74) *Attorney, Agent, or Firm*—Oblon, Spivak, McClelland, Maier & Neustadt, P.C.

(57) ABSTRACT

Fluids, such as protein-containing biological fluids, particularly plasma, may be effectively decontaminated by treatment with ultrasonic energy alone or in conjunction with either ozone or UV radiation. Suitable apparatus for decontaminating protein-containing biological fluids with such methods are disclosed.

16 Claims, 11 Drawing Sheets

Platelet Contactor

METHODS AND APPARATUS FOR DECONTAMINATING FLUIDS

BACKGROUND OF THE INVENTION

1. Field of the Invention

The present invention relates to methods for decontaminating fluids, including protein-containing biological fluids, in particular blood products, other natural biologicals, and synthetic biotechnology products. The present invention also relates to apparatus useful for decontaminating fluids, including protein-containing biological fluids, in particular blood products, other natural biologicals, and synthetic biotechnology products. The present invention further relates to apparatus for contacting ozone with a liquid.

2. Discussion of the Background

Protein-containing biological fluids are important for a number of reasons. In particular, protein-containing fluids such as whole blood and blood products, such as red blood cells, platelets, and plasma, are important components of the health care system. Likewise, modern health care is also dependent on other important protein-containing biological fluids, including synthetic biotechnology products such as recombinant clotting factors, as well as natural biological products, such as antitoxins and vaccines. Unfortunately, the source of these fluids and the fact that these fluids contain proteins make them susceptible to contamination by a variety of infectious agents, such as parasites, bacteria, fungi, and viruses.

The common factor in all of these contaminants is that they contain DNA and/or RNA. Decontamination of the protein-containing fluid thus does not necessarily require the removal of the contaminating agents, but only the disruption of the contaminating agents' DNA and/or RNA so that these agents cannot propagate and thus spread disease.

The approach of attacking DNA and/or RNA is particularly useful in the blood industry because red blood cells, platelets and plasma, which are the useful components of blood for transfusion and pharmaceutical manufacture, contain no DNA or RNA. Furthermore, the leukocytes, or white blood cells, do contain DNA and RNA, but it is desirable to destroy this material to eliminate graft versus host disease (GVHD), as recently recommended for general transfusion practice.

Because of these potential benefits, several techniques have been developed to attack DNA and/or RNA in blood and blood products. The main target of this work is plasma, which is the straw-colored material left after the cellular blood components have been removed. Rich in proteins and nutrients, plasma can harbor many contaminants, but the smallest of the above contaminants, and thus the most difficult to treat, are the viruses. Specifically, potentially lethal viruses, such as HIV and Hepatitis B, are of great concern. These contaminants pose a great hazard when contaminated units are inadvertently included in the large pools of plasma used for the manufacture of pharmaceuticals, thus possibly leading to large scale infection among the treated population.

The existing techniques to eliminate such pathogens from plasma were recently summarized at the 1998 AABB annual meeting (Transfusion Transmitted Diseases (Prions; Bacteria and Parasites); Selected Topics in Transfusion-Transmitted Infections: American Association of Blood Banks Annual Meeting, The Compendium, 1998) and the 1999 CHI annual blood safety and screening symposium (Safety Issues: New Inactivation Technologies: Plasma; Cambridge Healthtech Institute's Fifth Annual Blood Safety & Screening Symposium, Feb. 23–24, 1999). These techniques can be roughly divided into two groups: (1) those that can treat only enveloped viruses, and (2) those that can treat both enveloped and non-enveloped viruses.

Beginning with the techniques that can treat only enveloped viruses, the most notable example is the solvent/detergent combinations that are specifically directed at the viral envelope itself. In particular, the Red Cross and V. I. Technologies are now actively promoting one such product as Plas+SD. Intended for direct transfusion, Plas+SD provides some degree of safety and uniform product consistency. There are, however, concerns over: (1) cost; (2) residual solvent/detergent left in the product; (3) the use of a donor pool, albeit a relatively small one at about 2,000 units; (4) the inability to treat non-enveloped viruses; (5) the impact of new or emerging viruses (A. Pereira; "Cost-effectiveness of transfusing virus-inactivated plasma instead of standard plasma," Transfusion, vol. 39, pp. 479–487 (1999)); and (6) recent recalls (V. I. Tech Sees $3M, Or 24c/Shr 2Q Chg from Pdt Recall: Wall Street Journal/Dow Jones Newswires, Jul. 14, 1999).

Another technique for treating enveloped viruses is very high static pressure, on the order of 45,000 to 60,000 psi. However, the required pressure vessels are quite expensive and this technique, though used elsewhere (S. Denys et al, "Modeling conductive heat transfer and process uniformity during batch high-pressure processing of foods," Biotechnol. Prog., vol. 16(1), pp. 92–101 (2000)), is still under development in the plasma industry. Beyond the limitation to enveloped viruses, there are also the practical problems of contamination and/or leaking of the pump oil, as well as rupture of the plasma bag. One variation is to freeze the plasma (D. W. Bradley, et al, "Pressure cycling technology: a novel approach to virus inactivation in plasma," Transfusion, vol. 40(2), pp. 193–200 (2000)), but this process is relatively slow and raises the problem of freeze damage to the plasma proteins.

Of the many techniques capable of treating both enveloped and non-enveloped viruses, the most common example is intense light exposure. At high enough frequencies, in the UVC to gamma range, the energy in the light disrupts the basic structure of the contaminants. However, at these energies, there is also the problem of oxygen radical formation. To prevent these radicals from damaging the proteins, quenching agents are typically added to the plasma. Unfortunately, these agents are expensive, at least partially toxic, and must be removed before the plasma can be used. To avoid such problems, a limited exposure technique has recently been reported, but the results to date show only partial success, as well as some degree of protein damage (K. M. Remington, "Identification of Critical Parameters and Application to UVC Viral Inactivation in the Absence of Additives," Cambridge Healthtech Institute's Sixth Annual Blood Product Safety Symposium, Feb. 13–15, 2000).

An extension of these direct light exposure techniques is the addition of a light-sensitive compound, such as methylene blue, to the plasma. When activated by light of the appropriate wavelength, this compound then attacks the contaminants. Like the above solvent/detergent processes, however, there are concerns over costs and the effects of residual material in the so-treated plasma.

Yet another approach commonly used for both enveloped and non-enveloped viruses is heat treatment, typically with steam. Obviously, however, this approach is not suitable for heat-sensitive proteins and is not used for single plasma units.

Finally, there are also other techniques under development, such as various ozone processes, but these processes are typically expensive and difficult to execute in the closed environment required for plasma processing. In addition, ozone-based methods suffer from the disadvantage of requiring long treatment times. On the other hand, ozone itself is cheap and is quite effective given sufficient processing time, and leaves no toxic residue (M. M. Kekez, S. A. Sattar; "A new ozone-based method for virus inactivation: preliminary study," Phys. Med. Biol., vol. 42, pp. 2027–2039 (1997); U.S. Pat. No. 4,632,980; and U.S. Pat. No. 5,882,591).

To achieve better results, some of the above decontamination techniques have been combined. For example, the combination of the heat and solvent/detergent processes is quite effective against pathogens such as HIV (B. Horowitz; "Virus Inactivation by Solvent/Detergent Treatment and the Manufacture of SD-Plasma," Vox Sang, vol. 74, Suppl. 1, pp. 203–206 (1998)).

Unfortunately, all of the above decontamination techniques, as well as others, have serious problems. The underlying difficulty is that the contaminant viral DNA and/or RNA are both proteins, any thus any technique that disrupts these contaminants can also cause significant damage to the desired proteins in the treated fluid. This is of great concern because damaged proteins are less effective clinically. For example, excessive decontamination damage of this protein will reduce the concentration in the fibrin glues used during surgery, and the resulting glue will thus not be capable of either approximating a wound or inducing hemostasis. Furthermore, damaged proteins also induce antibody formation, thereby making future treatment quite difficult (Barbara A. Konkle; "New Products for Patients with Hemophilia or von Willebrand Disease," American Association of Blood Banks Annual Meeting, The Compendium, Baltimore, MD, pp. 111–115, 1998).

In addition, the contaminants and the desired proteins are also so similar that any technique that completely destroys all of the contaminants would also destroy all of the desired proteins. For this reason, no practical decontamination technology can be completely effective, and thus some small degree of contamination will always remain in the treated fluid. This is a particular problem for lethal contaminants such as HIV and Hepatitis B. In such cases, the goal is thus to reduce the contaminant as much as possible. In practice, acceptable levels are generally considered to be a logarithmic reduction factor (LRF) of 6, which means that 1 part in 1 million survives treatment.

Of course, because erythrocytes and platelets also have proteins similar to those found in contaminant, DNA and RNA, the problems of protein damage and incomplete decontamination also extend to these blood components.

Furthermore, similar problems also arise in the treatment of biologics other than blood products. Specifically, these other biologics, whether of synthetic or natural origin, should contain no untreated genetic material of their own, and should also not be contaminated with foreign DNA and/or RNA. On the other hand, the proteins in these biologics are similar to the proteins in the contaminating DNA and/or RNA. The net result of any treatment is thus again at least some protein damage, along with limited decontamination.

Finally, blood products and other biologics are also subject to several other problems. For example, in the modern health care environment, costs must be carefully controlled, both for capital equipment and any disposables. Likewise, technician time and training must be kept to minimum levels. Beyond these cost factors, however, there are also several process concerns. Specifically, the overall processing time must be kept as short as possible, as demonstrated by the recent and ongoing shortages in various intravenous immunoglobulins (IVIGs). In addition, there is only a limited supply of starting material, which must therefore be treated as efficiently as possible. Of course, all of the above concerns must be met, while also satisfying stringent regulatory requirements for safety and efficacy, along with full documentation.

The most difficult problem in decontamination work, however, is the possibility of contamination by agents that do not follow the normal DNA or RNA infection route. Specifically, recent work indicates that infections may also proceed by distortions in protein shape. In this case, the underlying agent is referred to as a "prion" and the resulting disease is commonly called "mad cow disease" in the bovine form, "scrapie" in the sheep form, and Creutzfeldt-Jakob Disease in the human form. Although their resistance to conventional decontamination technologies in fact characterizes prions, recent work indicates that these infectious agents may be at least partially susceptible to gamma irradiation, and possibly subject to sonic or ozone effects as well. It is therefore understood that the following techniques that are designed to protect proteins during decontamination for conventional agents can also be applied to protect proteins during prion decontamination.

A method for freeing blood and blood components of viable enveloped viruses by contacting the blood or blood product with ozone is disclosed in U.S. Pat. No. 4,632,980. U.S. Pat. No. 5,882,591 discloses a method and apparatus for disinfecting biological fluids, such as plasma/serum, through the interaction with gases, such as ozone.

SUMMARY OF THE INVENTION

Thus, there remains a need for effective processes for decontaminating fluids, including protein-containing biological fluids, such as plasma. In particular, there remains a need for processes for decontaminating protein-containing biological fluids, such as plasma, which may be applied to individual units as well as pooled units, and which afford improved protection against infectious agents, including viruses. In addition, these processes must be fast, efficient, inexpensive, and cause minimum damage to the desired proteins. There also remains a need for apparatus which are useful for carrying out such processes.

Accordingly, it is one object of the present invention to provide novel methods for decontaminating fluids.

It is another object of the present invention to provide novel methods for decontaminating protein-containing biological fluids.

It is another object of the present invention to provide novel methods for decontaminating plasma.

It is another object of the present invention to provide novel methods for decontaminating human plasma.

It is another object of the present invention to provide novel methods for decontaminating protein-containing biological fluids which provide a high level of protection from infectious agents.

It is another object of the present invention to provide novel methods for decontaminating plasma which provide a high level of protection from infectious agents.

It is another object of the present invention to provide novel methods for decontaminating human plasma which provide a high level of protection from infectious agents.

It is another object of the present invention to provide novel methods for decontaminating protein-containing biological fluids which provide a high level of protection from viruses.

It is another object of the present invention to provide novel methods for decontaminating plasma which provide a high level of protection from viruses.

It is another object of the present invention to provide novel methods for decontaminating human plasma which provide a high level of protection from viruses.

It is another object of the present invention to provide novel methods for decontaminating plasma which may be readily applied to individual plasma units.

It is another object of the present invention to provide novel methods for decontaminating human plasma which may be readily applied to individual plasma units.

It is another object of the present invention to provide novel methods for decontaminating plasma which may be readily applied to batch processing of pooled plasma units.

It is another object of the present invention to provide novel methods for decontaminating human plasma which may be readily applied to batch processing of pooled plasma units.

It is another object of the present invention to provide novel apparatus useful for decontaminating fluids.

It is another object of the present invention to provide novel apparatus useful for decontaminating protein-containing biological fluids.

It is another object of the present invention to provide novel apparatus useful for decontaminating plasma.

It is another object of the present invention to provide novel apparatus useful for decontaminating human plasma.

It is another object of the present invention to provide novel apparatus useful for decontaminating protein-containing biological fluids which provide a high level of protection from infectious agents.

It is another object of the present invention to provide novel apparatus useful for decontaminating plasma which provide a high level of protection from infectious agents.

It is another object of the present invention to provide novel apparatus useful for decontaminating human plasma which provide a high level of protection from infectious agents.

It is another object of the present invention to provide novel apparatus useful for decontaminating protein-containing biological fluids which provide a high level of protection from viruses.

It is another object of the present invention to provide novel apparatus useful for decontaminating plasma which provide a high level of protection from viruses.

It is another object of the present invention to provide novel apparatus useful for decontaminating human plasma which provide a high level of protection from viruses.

It is another object of the present invention to provide novel apparatus useful for decontaminating plasma which may be readily applied to individual plasma units.

It is another object of the present invention to provide novel apparatus useful for decontaminating human plasma which may be readily applied to individual plasma units.

It is another object of the present invention to provide novel apparatus useful for decontaminating plasma which may be readily applied to batch processing of pooled plasma units.

It is another object of the present invention to provide novel apparatus useful for decontaminating human plasma which may be readily applied to batch processing of pooled plasma units.

It is another object of the present invention to provide novel apparatus for contacting ozone with a liquid.

These and other objects, which will become apparent during the following detailed description, have been achieved by the inventor's discovery, in a first main embodiment, of a method for decontaminating plasma by:

(a) treating plasma with ultrasonic energy.

The inventor has also discovered, in a second main embodiment, that plasma may be effectively decontaminated by a method involving:

(a') a step for the treatment of plasma with ultrasonic energy.

The inventor has further discovered, in a third main embodiment, that a fluid, such as a protein-containing biological fluid, may be effectively decontaminated by a method involving:

(a) treating a fluid with ultrasonic energy, while degassing the fluid.

The inventor has also discovered, in a fourth main embodiment, that such fluids may be effectively decontaminated by a method involving:

(a') a step for the treatment of a fluid with ultrasonic energy, while degassing the fluid.

The inventor has further discovered, in a fifth main embodiment, that a fluid, such as a protein-containing biological fluid may be effectively decontaminated by a method involving:

(a) simultaneously treating a fluid with at least two different frequencies of ultrasonic energy.

The inventor has also discovered, in a sixth main embodiment, that such fluids may be effectively decontaminated by a method involving:

(a') a step for the simultaneous treatment of a fluid with at least two different frequencies of ultrasonic energy.

The inventor has also discovered, in a seventh main embodiment, that such fluids may be effectively decontaminated by a method involving:

(a) treating a fluid with ultrasonic energy to obtain a de-oxygenated fluid; and (b) irradiating said de-oxygenated fluid.

The inventor has also discovered, in an eighth main embodiment, that such a fluid may be effectively decontaminated by a method involving:

(a') a step for the treatment of a fluid with ultrasonic energy to obtain a de-oxygenated fluid; and (b') a step for the irradiation of said de-oxygenated fluid.

The inventor has further discovered, in a ninth main embodiment, that such fluids may be effectively decontaminated by a method involving:

(a) treating a fluid with ultrasonic energy to obtain a de-oxygenated fluid; and (b) contacting said de-oxygenated fluid with a pulsed electric field.

The inventor has also discovered, in a tenth main embodiment, that such a fluid may be effectively decontaminated by a method involving:

(a') a step for the treatment of a fluid with ultrasonic energy to obtain a de-oxygenated fluid; and (b') a step for contacting said de-oxygenated fluid with a pulsed electric field.

The inventor has further discovered, in an eleventh main embodiment, that a fluid, such as a protein-containing biological fluid may be effectively decontaminated by a method involving:

(a) treating a fluid with ultrasonic energy to obtain a de-oxygenated fluid; and (b) contacting said de-oxygenated fluid with ozone.

The inventor has also discovered, in a twelfth main embodiment, that such a fluid may be effectively decontaminated by a method involving:
 (a') a step for the treatment of a fluid with ultrasonic energy to obtain a de-oxygenated fluid; and
 (b') a step for the treatment of said de-oxygenated fluid with ozone.

The inventor has further discovered, in a thirteenth main embodiment, that a fluid, such as protein-containing biological fluid, may be effectively decontaminated by a method involving:
 (a) mixing a fluid with ozone, to obtain an ozone-containing fluid; and
 (b) treating said ozone-containing fluid with ultrasonic energy.

The inventor has also discovered, in a fourteenth main embodiment, that such a fluid may be effectively decontaminated by a method involving:
 (a') a step for mixing a fluid with ozone, to obtain an ozone-containing fluid; and
 (b') a step for the treatment of said ozone-containing fluid with ultrasonic energy.

The inventor has further discovered, in a fifteenth main embodiment, that a fluid, such as a protein-containing biological fluid, may be effectively decontaminated by a method involving:
 (a) treating a fluid with ultrasonic energy to obtain a de-oxygenated fluid;
 (b) contacting said de-oxygenated fluid with ozone, to obtain an ozone-containing fluid; and
 (c) treating said ozone-containing fluid with ultrasonic energy.

The inventor has also discovered, in a sixteenth main embodiment, that such a fluid may be effectively decontaminated by a method involving:
 (a') a step for the treatment of a fluid with ultrasonic energy to obtain a de-oxygenated fluid;
 (b') a step for the treatment of said de-oxygenated fluid, to obtain an ozone-containing fluid; and
 (c') a step for the treatment of said ozone-containing fluid with ultrasonic energy.

The inventor has further discovered, in a seventeenth main embodiment, that a fluid, including a protein-containing biological fluid, may be effectively decontaminated by a method involving:
 (a) treating a fluid with ultrasonic energy to obtain a de-oxygenated fluid;
 (b) irradiating said de-oxygenated fluid, to obtain an irradiated fluid; and
 (c) contacting said irradiated fluid with ozone, to obtain an ozone-containing fluid.

The inventor has also discovered, in an eighteenth main embodiment, that such a fluid may be effectively decontaminated by a method involving:
 (a') a step for the treatment of a fluid with ultrasonic energy to obtain a de-oxygenated fluid;
 (b') a step for the irradiation of said de-oxygenated fluid, to obtain an irradiated fluid; and
 (c') a step for the treatment of said irradiated fluid, to obtain an ozone-containing fluid.

The inventor has further discovered, in a nineteenth main embodiment, that a fluid, including a protein-containing biological fluid, may be effectively decontaminated by a method involving:
 (a) treating a fluid with ultrasonic energy to obtain a de-oxygenated fluid;
 (b) irradiating said de-oxygenated fluid, to obtain an irradiated fluid;
 (c) contacting said irradiated fluid with ozone, to obtain an ozone-containing fluid; and
 (d) treating said ozone-containing fluid with ultrasonic energy.

The inventor has also discovered, in a twentieth main embodiment, that such a fluid may be effectively decontaminated by a method involving:
 (a') a step for the treatment of a fluid with ultrasonic energy to obtain a de-oxygenated fluid;
 (b') a step for the irradiation of said de-oxygenated fluid, to obtain an irradiated fluid;
 (c') a step for the treatment of said irradiated fluid, to obtain an ozone-containing fluid; and
 (d') a step for the treatment of said ozone-containing fluid with ultrasonic energy.

The inventor has also discovered, in a twenty-first main embodiment, that a fluid, including a protein-containing biological fluid, may be effectively decontaminated by means of an apparatus which contains:
 (1) a chamber for containing a fluid;
 (2) a vacuum source coupled to the chamber; and
 (3) a source of ultrasonic energy coupled to the chamber, wherein said chamber comprises (i) a flat panel, (ii) an inlet, and (iii) an outlet; and wherein said flat panel of said chamber and said inlet are dimensioned such that a fluid flowing through said inlet and across said flat panel to said outlet will form a thin film and travel in plug flow at least during some portion of its flow across said flat panel.

The inventor has further discovered, in a twenty-second main embodiment, that such a fluid may be effectively decontaminated by means of an apparatus which contains:
 (1') a means for containing said fluid;
 (2') means for contacting said fluid with a vacuum; and
 (3') a means for introducing ultrasonic energy into said means for containing said fluid, wherein said means for containing said fluid comprises (i) a means for the introduction of said fluid into said containing means, (ii) a means for said fluid to flow through said containing means, and (iii) a means for the removal of said fluid from said containing means; and wherein said containing means is dimensioned such that a protein-containing fluid flowing through said containing means will form a thin film and travel in plug flow at least during some portion of its flow through said containing means.

The inventor has also discovered, in a twenty-third main embodiment, that a fluid, including a protein-containing biological fluid, may be effectively decontaminated by means of an apparatus which contains:
 (1) a chamber for containing a fluid;
 (2) a vacuum source coupled to the chamber;
 (3) a source of ultrasonic energy coupled to such chamber; and
 (4) a source of UV, gamma, or x-ray radiation.

The inventor has also discovered, in a twenty-fourth main embodiment, that a fluid, including a protein-containing biological fluid, may be effectively decontaminated by means of an apparatus which contains:
 (1') a means for containing said fluid;
 (2') means for contacting said fluid with a vacuum;
 (3') a means for introducing ultrasonic energy into said means for containing said fluid; and
 (4') a means for the treatment of said fluid with UV, gamma, or x-ray radiation.

The inventor has also discovered, in a twenty-fifth main embodiment, that a fluid, including a protein-containing biological fluid, may be effectively decontaminated by means of an apparatus which contains:
(1) a chamber for containing a fluid;
(2) a vacuum source coupled to the chamber;
(3) a source of ultrasonic energy coupled to such chamber; and
(4) a source of ozone, wherein said chamber comprises: (i) an inlet for introducing ozone from the source of ozone; (ii) an inlet for introducing plasma; and (iii) a device for mixing ozone from the source of ozone with a fluid.

The inventor has further discovered, in a twenty-sixth main embodiment, that a fluid, including a protein-containing biological fluid, may be effectively decontaminated by means of an apparatus which contains:
(1') a means for containing said fluid;
(2') a means for contacting said fluid with a vacuum;
(3') a means for introducing ultrasonic energy into said means for containing said fluid; and
(4') a means for generating ozone, wherein said means for containing said fluid comprises: (i) a means for the introduction of ozone from said means for generating ozone into said containing means; (ii) a means for the introduction of said fluid into said containing means; and (iii) a means for mixing said ozone from said means for generating ozone with said fluid in said containing means.

The inventor has also discovered, in a twenty-seventh main embodiment, that a fluid, including a protein-containing biological fluid, may be effectively decontaminated by means of an apparatus which contains:
(1) a chamber for containing a fluid;
(2) a vacuum source coupled to the chamber;
(3) a source of UV, gamma, or x-ray radiation;
(4) a source of ultrasonic energy coupled to such chamber; and
(5) a source of ozone, wherein said chamber comprises: (i) an inlet for introducing ozone from the source of ozone; (ii) an inlet for introducing plasma; and (iii) a device for mixing ozone from the source of ozone with a fluid.

The inventor has further discovered, in a twenty-eighth main embodiment, that a fluid, including a protein-containing biological fluid, may be effectively decontaminated by means of an apparatus which contains:
(1') a means for containing said fluid;
(2') a means for contacting said fluid with a vacuum;
(3') a means for the treatment of said fluid with UV, gamma, or x-ray radiation.
(4') a means for introducing ultrasonic energy into said means for containing said fluid; and
(5') a means for generating ozone, wherein said means for containing said fluid comprises: (i) a means for the introduction of ozone from said means for generating ozone into said containing means; (ii) a means for the introduction of said fluid into said containing means; and (iii) a means for mixing said ozone from said means for generating ozone with said fluid in said containing means.

The inventor has further discovered, in a twenty-ninth main embodiment, that ozone may be effectively contacted with a liquid with an apparatus which comprises:
(1) a substrate which has a lower surface and an upper surface and which has a plurality of passage-ways connecting said lower surface with said upper surface;
(2) a source of ultrasonic energy coupled to said substrate, such that said ultrasonic energy is introduced into the liquid by the vibration of said substrate;
(3) a source of ozone connected to said lower surface of said substrate.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
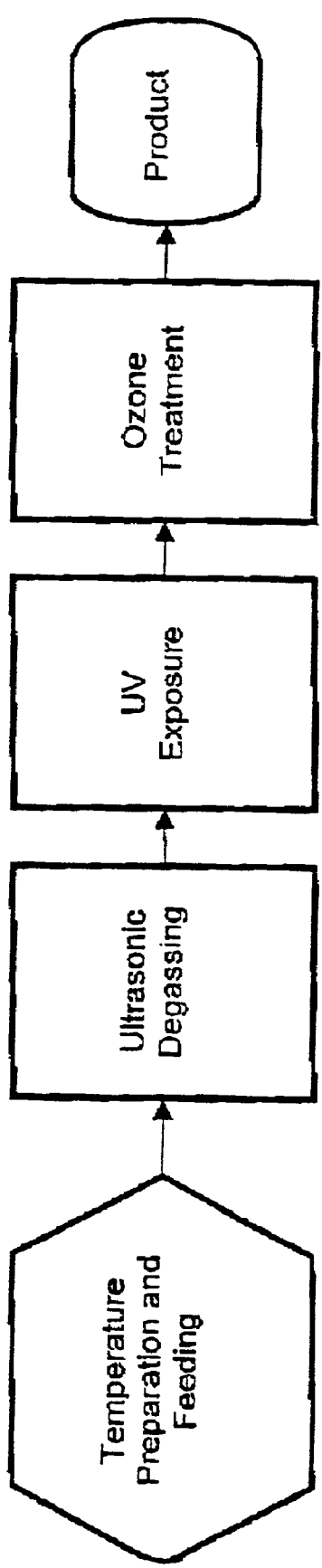
FIG. 1 is a flow chart which depicts one embodiment of the method according to the present invention.

Thus, the present invention provides novel methods and apparatus for decontaminating a fluid. In certain preferred embodiments, the fluid is a liquid such as a protein-containing biological fluid. Suitable protein-containing biological fluids include body fluids, such as whole blood, saliva, semen, spinal fluid, etc. In addition to whole blood, the protein-containing biological fluid may be a blood product, such as plasma, sera, and the red blood cell (erythrocyte) or platelet fractions of whole blood. The protein-containing biological fluid may also be any natural or synthetic protein-containing fluid derived from various in vitro or in vivo processes, such as a fermentation broth.

In a particularly preferred embodiment of the present invention, the protein-containing biological fluid is plasma. The present methods and apparatus are discussed in detail below primarily in the context of the decontamination of plasma. However, it is to be understood that the present methods and apparatus may also be used to decontaminate the protein-containing biological fluids discussed above, including foodstuffs (including eggs) and reaction mixtures containing fermentation products such as those obtained by recombinant DNA technology. The present invention is applicable not only to protein-containing biological fluids, but other heat-sensitive materials as well. In particular, the pulsed electric field (PEF) methods discussed below are effective for decontaminating apple juice. Thus, in the context of the present methods, the fluid may be any liquid which is desired in decontaminated form, and includes juices such as apple juice, orange juice, tomato juice, etc. In the context of the present invention, the term fluid also includes liquid-like materials which are not typically thought of as liquids. Thus, the present methods and apparatus may also be applied to the decontamination of eggs, etc. for in vitro fertilization (IVF). The present methods may also be applied to foodstuffs, which do not necessarily have to include proteins. Likewise, the present methods may be used anywhere there is a problem of contamination, particularly in regard to PEF.

The plasma to be treated may be that of any mammal, such as dog, cat, cow, horse, pig, chimpanzee, and human. In a preferred embodiment, the plasma to be decontaminated is human plasma.

The plasma to be decontaminated may be collected by any conventional technique, such as from whole blood donation or apheresis, in which cells are returned to the donor. Whole blood donation involves taking less volume from the donor (about 200 ml), but requires a fairly long time (on the order of months) between donations. Apheresis involves taking a greater volume from the donor (about 600 ml) but, since cells are returned to the donor, requires a shorter time (on the order of weeks) between donations. The collection of plasma is described in AABB (American Association of Blood Banks) Press Technical Manual, $13^{th}$ Edition, Baltimore Md., 1999, which is incorporated herein by reference.

The plasma to be decontaminated may be an individual unit obtained from a single donor. Alternatively, the plasma to be decontaminated may be obtained by pooling a large number of individual units taken from a correspondingly large number of donors.

As noted above, a method of decontaminating plasma need not remove or even inactivate all infectious agents to be considered useful. In fact, many methods of decontaminating plasma are specifically designed to address only certain types of infectious agents, e.g., enveloped viruses, and none guarantees removal or inactivation of 100% of even the infectious agent for which it is designed. Accordingly, in the context of the present invention, the term "method of decontaminating plasma" refers to a method which is capable of removing and/or inactivating a significant portion of at least one infectious agent found in plasma. Typically, the present methods for decontaminating plasma are capable of achieving a log reduction factor or log kill of at least 4, preferably at least 5, more preferably at least 6, for at least one infectious agent found in plasma.

The present methods are also capable of affecting the decontamination of plasma, while minimizing the damage to plasma proteins. The amount of protein damage will depend on the particular protein in question, the particular embodiment of the decontamination method used, and, to some extent the source and prior handling of the plasma. However, the present methods are capable of achieving the above-noted log kills of at least one infectious agent while causing protein damage of less than 20%, less that 10%, and even on the order of a few percent, as determined by the accepted clinical laboratory method used to quantify the given protein. For example, to determine the fibrinogen concentration, a known amount of thrombin is added to a known amount of plasma, and then the elapsed time for clot formation is measured and compared to a calibrated standard. In a modern hematology laboratory, this and similar tests for other proteins are routinely performed by automated equipment, thus providing an accurate, documented means of determining the degree of protein damage.

Examples of the types of infectious agents which may be removed and/or inactivated by the present methods include parasites, bacteria, fungi, and viruses, and possibly prions.

Of these agents, parasites pose significant threats mainly in tropical climates. The greatest such risk is malaria, which is spread by all four different species of Plasmodium, but principally by *Plasmodium malariae*. Another parasitic risk is *Trypanosoma cruzi*, which causes Chaga's Disease, a serious problem in Central and South America. In the United States, two species of Babesi protozoans, which cause Babesiosis, can be transmitted by transfusion, although the more common route is tick bite. Leishmania infantum is also a parasite which may be found in blood products.

Bacteria also present a continuous threat in transfusion. For this reason, the CDC and leading members of the blood community have recently launched the BaCon (Bacterial Contamination) study to determine the risks of transfusion related infections. Of particular interest are *Yerisinia enterocolitica, Escherichia coli, Citrobacter freundii*, as well as Bartonella and Brucella species.

Fungal infections are a continuous and escalating problem in medical care, particularly for those patients with compromised immune systems due to cancer therapy, HIV, etc. Although the terms fungus and mold are often interchanged, one convention is that mold refers to the typically woolly appearance of a growing fungus. Following this convention, a yeast is then a particular minute fungus, especially of the Saccharomycetaceae family. There are many such opportunistic infections, some of the more common agents of clinical concern being *Candida albicans* and *Candida stellatoidea*, as well as *Cryptococcus neoformans*.

Finally, the main viruses of concern are the various strains of hepatitis (A through E, and G), HIV (human immunodeficiency virus), HTLV (human t-cell lymphotropic virus) types I and II, CMV (cytomegalovirus), EBV (Epstein-Barr virus) and parvovirus B19.

In most cases, the above contaminants are of concern mainly in transfusion from one patient to another. It is also possible, however, to treat the blood of any individual for such contaminants, and then transfuse this blood back to the patient. For example, such an approach lowers the burden of HIV circulating in the blood of AIDS patients. Such an approach could also be applied to the treatment of non-infectious agents in the blood, such as non-Hodgkins lymphoma (see, "Theratechnologies Enrolls 1st Patient In Theralux Trial," Wall Street Journal, Jan. 29, 2001).

Beyond the blood industry, there are also several applications in other biologics. In particular, there is great emerging interest in biotechnology and related technologies. The underlying problems will be discussed at the upcoming joint Parenteral Drug Association (PDA) and FDA Viral Clearance Forum, PDA Conference Files, Fall 2001. For example, one problem facing this industry is that a murine hybridoma would likely be contaminated with murine retroviruses, whatever they may be found to be. The possibility of a resulting cross-species contamination is of great concern, given that swine flu in the past has caused devastating pandemics. Highly effective decontamination measures are therefore essential for the emerging biotechnologies.

In addition to biologics, there are also other applications for decontamination technologies. One major area is food science, which requires effective decontamination of a variety of contaminants, notably bacteria such as Salmonella. Effective decontamination of food products thus improves safety and extends shelf life.

There are also other possibilities of using improved decontamination techniques where the material to be treated is not normally considered to be a contaminant. Specifically, recent advances in in vitro fertilization (IVF) have raised the possibility of taking an oocyte from a female donor, and removing the nucleus along with most of the genetic material. The genetic material from a second female is then inserted into the oocyte, which is then fertilized with the intent of producing a viable pregnancy. The problem with this approach is that not all of the donor genetic material can be removed, leaving primarily some mitochondrial DNA. As a result, the resulting infant has a genetic contribution from three "parents," causing a great deal of practical and ethical concerns. Using a decontamination technique to disrupt all of the donor genetic material, while leaving the other proteins essentially intact, would eliminate such concerns.

Finally, the unique equipment described in the following can also be used for purposes other than decontamination. In particular, the ozone treatment unit is also useful for adding gasses to liquids in general. For example, in the case of medical applications, the device can be used to oxygenate blood during cardiopulmonary bypass. For food and/or industrial applications, the ozone treatment unit can be used to add carbon dioxide to aqueous solutions; other similar applications are also possible.

I. Thus, in a first main embodiment, the present invention provides a method for decontaminating plasma which comprises:

(a) treating plasma with ultrasonic energy.

The terms "ultrasonic energy" and "ultrasound" refer to sonic waves with frequencies in the range of 20 kHz, the upper limit of human hearing, to several hundred MHz.

Several different techniques can be used to generate ultrasound, but the most common approach is to apply electrical impulses to a piezoelectric crystal. The activated crystal then expands and contracts along its primary axes to yield pressure pulses or sonic waves (ultrasound). In addition, ultrasonic vibrations may also be generated by other conventional means, in particular by electromagnetic, electrostrictive, or magnetostrictive devices. Such devices are described in published PCT Patent Application WO 92/20420, which is incorporated herein by reference.

Because of its relatively high frequency range, ultrasound has many applications in industry and medicine. In particular, ultrasound has many unique and beneficial applications in the treatment of liquids.

Of these applications, the most common and most significant involve cavitation. Cavitation is a localized vaporization that occurs when the low pressure part of the ultrasonic wave becomes less than the vapor pressure of the liquid. Under these conditions, the local temperatures and pressures become extremely high as the cavitation bubbles grow and then collapse.

These extreme conditions are used for many practical applications, including the rupture of biological cell walls. This capability thus has immediate use in decontamination, particularly for parasites. Due to wavelength restrictions, smaller contaminants such as bacteria, fungi and viruses can also be treated, but to a lesser degree. The treated liquids thus include all non-cellular protein containing liquids. In particular, in the blood industry, the treated liquids are plasma or sera, but not red blood cells or platelets.

The overall arrangement for this first embodiment is therefore much like that used for cell disruption. Specifically, three separate components are required: a source of ultrasound, a target, and some means of coupling the source to the target. The limiting factor here is that the high frequency waves of ultrasound do not propagate well in gasses such as air, and therefore require a carrier medium such as a rigid metal or a liquid. In the case of metal, waveguides are commonly made of aluminum. With careful shaping into geometries called horns, these waveguides can produce waves of high amplitudes and energies, resulting in efficient transfer of the ultrasonic energy into the target.

Another similarity between the decontamination technology in this first embodiment and the existing cell disruption technology is that both units operate in the lower range of ultrasound frequencies. The underlying physical principle here is that, for water and dilute aqueous systems, the power required to produce cavitation increases dramatically above 100 kHz. Of course, some cavitation occurs at even higher frequencies and the present method may utilize such higher frequencies of ultrasonic energy. In particular, it is anticipated that higher frequencies will be used as more equipment in the several hundred kHz to the MHz frequency, or "megasonic" range, becomes readily available.

In this first embodiment of the present method, plasma is therefore treated with ultrasonic energy having a frequency sufficient to result in cavitation of the plasma. Thus, the plasma is suitably treated with ultrasonic energy having a frequency of 20 kHz to 10 MHz, preferably 20 kHz to 1 MHz, more preferably 20 kHz to 500 kHz, even more preferably 20 kHz to 100 kHz.

Although there are thus some similarities between the decontamination technology described in this first embodiment and conventional cell wall rupturing equipment, there are, however, some significant differences. Specifically, it is important for effectiveness and for regulatory compliance that the ultrasonic frequency is tightly maintained and that cavitation actually occurs in each and every use of the equipment. To ensure that these conditions are met, the process must be monitored, preferably by the use of a hydrophone and supporting electronics (model bx-208/308, ppb, Inc., San Diego, Calif.).

Another significant difference between the new decontamination and conventional cell disruption equipment is that the decontamination unit must carefully preserve the desired protein components, to a level well beyond the degree of protection required for cell disruption devices.

The first problem in the protection of these proteins is limiting the strong chemical reactions that are induced by ultrasonic cavitation. One such reaction is the breaking of long chain organic compounds by the severe agitation due to bubble growth and collapse during cavitation. This breaking may be a significant concern for the large, relatively delicate proteins involved in the clotting process, as described by El'piner (I. E. El'piner, *Ultrasound Physical, Chemical, and Biological Effects*, Consultants Bureau, New York, p. 217, 1964).

In the present method, such damage of the plasma proteins may be managed by two techniques. First, the treatment times are kept short, i.e., less than 5 minutes, preferably less than 2 minutes, more preferably less than 30 seconds. Second, the intensity levels are kept low, i.e., 0.1 to 50 W/cm$^2$, preferably 0.5 to 10 W/cm$^2$, and more preferably 1 to 6 W/cm$^2$. Of course, in practice these techniques must be adjusted to specific protein solutions and contaminants.

Another reaction that is quite damaging to protein solutions undergoing sonic treatment is the formation of free radicals in the liquid due to the extreme temperature and pressure changes of cavitation (V. Misik and P. Riesz, "Detection of primary free radical species in aqueous sonochemistry by EPR spectroscopy," in *Sonochemistry and Sonoluminescence*, edited by L. A. Crum, T. J. Mason, J. L. Reisse and K. S. Suslick, NATO ASI Series C, Kluwer Academic Publishers, Dordrecht, pp. 225–236, 1999). The preferred method to limit these radicals is to reduce the ultrasonic treatment intensities and exposure times, as described above to prevent chain breakage.

In addition to the liquid, however, free radicals can also form at the surface of the treated liquid. Of these radicals, the most damaging ones are those formed from oxygen.

Accordingly, in a preferred subembodiment of this first main embodiment, the ultrasonic energy is applied after the gas above the plasma has been replaced with an inert atmosphere. In this case, "inert" does not include the noble gasses, because such monatomic species have too few degrees of freedom to disperse the ultrasonic energy (S. Y. Wang, in *Symposium on Biological Effects and Characterizations of Ultrasound Sources*, edited by D.G. Hazzard, et al, US Dept. HEW (FDA) 78-8948, US Government Printing Office, p. 196, 1977). Instead, suitable inert gasses must be polyatomic, notably carbon dioxide. In practice, forming a carbon dioxide gas layer simply amounts to dropping a pellet of dry ice into the solution to be treated (*High Intensity Ultrasonic Processor User's Guide*, Sonics & Materials, Inc. Newton, Conn., 1999). The evolved gas then displaces the oxygen, and without oxygen, no oxygen radicals can form.

During this process, some of the dissolved gasses are also displaced by carbon dioxide. Part of this displacement occurs by a concentration gradient in the immediate vicinity of the pellet, but most of this displacement is due to transport from the enriched carbon dioxide gas layer above the liquid surface. In either case, the net result is preferential removal of oxygen, which again is beneficial because oxygen radicals are quite damaging to proteins. Note that the overall process is thus similar to the helium sparging technique commonly used in hplc, but helium cannot be used here because of the above described formation of noble gas radicals.

Beyond controlling the formation of free radicals, another major problem in limiting protein damage is the control of excess heat, primarily from the source of the ultrasound. To achieve this control, some means of cooling must be provided. A preferred means of limiting the source heat is to apply a water flow to the ultrasound source and/or horn. A preferred means to cool the target is immersion in a water bath, which also yields strong acoustic coupling to the ultrasound horn and source.

With these techniques, it is thus possible to maintain the target at any selected temperature. This temperature, however, depends on concerns that are often conflicting. Specifically, proteins are typically heat sensitive, particularly clotting factors such as Factor VIII. For maximum protection, the temperature should therefore be kept relatively low, within the FDA specified range of 2 to 10° C. On the other hand, cavitation in water or dilute aqueous systems is most effective at about 50° C. (J. Blitz, *Ultrasonics: Methods and Applications*, The Butterworths Group, London, pp. 133–4, 1971). At this temperature, a minimum amount of energy is required to induce bubble formation, and with less energy there is less protein chain breakage and less radical formation. In addition, there is less dissolved gas at higher temperatures, thereby further reducing the formation of the oxygen radicals that are most damaging, as noted above.

For these reasons, the unit should be operated at about 50° C., if the target can withstand such elevated temperatures. In particular, for those proteins that can tolerate even higher temperatures, use of the highest possible range provides thermal inactivation of pathogens, which is an additional safety measure. In this case, temperatures slightly greater than 50° C. may result in some decrease in cavitation efficiency, but this is more than compensated by the resulting improvement in thermal inactivation. Alternatively, even higher decontamination temperatures can be used as a separate step, with cavitation done in the lower, 50° C. range.

For less robust materials, the liquid should be kept cold until immediately before treatment, at which time rapid heating techniques should be applied to small samples to raise the operating temperature to no more than 50° C. At this time, the ultrasound should be applied for as short a duration and intensity as possible, with the sample then rapidly cooled back to storage temperatures.

Finally, for those samples that cannot withstand even minimal times at elevated temperatures, the sonic treatment should be performed at the highest allowable temperature, followed by rapid cooling to remove any residual heat from the ultrasound source or from the cavitation process.

All three of these processes thus require some means of effective heat transfer. For those materials that can withstand elevated temperatures, there are several heating options to achieve such temperatures in practice. For robust materials that can withstand prolonged heating, the entire source bag or container can be warmed and maintained at the desired elevated temperature. Water bath immersion, microwaves, air blast, or any other convenient technique can be employed for this warming.

For rapid heating of more temperature sensitive materials, the volume to be treated is first broken into smaller units, or into a continuous, low volume per time flow. These smaller units or flows are then passed through a separate bag with a large surface area where they are subjected to heat transfer from any convenient source, such as from a water bath, microwave, air blast, etc.

A similar approach is used for rapid cooling. In this case, however, suitable cooling mechanisms are water bath immersion, or contact with plates that are cooled by gas expansion or Peltier effects.

It should also be understood that the method of the first main embodiment may be carried out in either a batch-wise, semi-continuous, or continuous fashion. For batchwise decontamination, single bag units may be individually treated with the ultrasonic energy. Alternatively, in a semi-continuous operation, single units or individual small volumes of plasma may flow through one or more stations or stages in which they are treated with ultrasonic energy. In this mode of operation, each individual unit or volume is held at each station or stage for processing, and is then passed in bulk to the next station or stage. Yet another alternative is a continuous operation, in which the plasma may flow without interruption through the stations or stages. Both the semi-continuous and continuous modes are applicable to fractionation or to other processes involving very large pools of material to be treated.

To achieve all of these different modes of operation in practice, a special treatment chamber is required.

The first condition on this chamber is that the inlet tube or tubes must not harbor any pathogens. The underlying problem can be seen in conventional blood bags, in which the inlet tube passes through a port in the top seam of such containers. As such, any untreated fluid that remains in this tube can subsequently contaminate the treated fluid. This is a particular problem for ultrasound and the other treatment technologies described below because after such treatment processes are terminated, no residual material remains in the fluid to prevent any recurrence of the pathogens.

To prevent this problem, the inlet tube may be heat sealed close to the bag, but this approach still leaves the port, which is relatively hard to seal. Since such ports are also rather narrow, the ultrasonic waves are thus effectively attenuated within a few tube diameters of the tube orifice, thereby leaving little or no treatment of any pathogens farther up the length of the tube.

A simple alternative for batch treatment is to heat seal the bag itself, below the tube orifice. For effective sealing, this procedure must be carried out when the liquid has already been forced out of the sealing zone by external compression of the bag.

For semi-continuous processes, a modified compression approach is preferred. In this case, the treatment chamber is clamped tightly just below the tube orifice, as described above, but in this case, no heat seal is used. Instead, the fluid in the chamber is treated and then drained before the next batch of fluid is allowed to enter by releasing the clamp. To ensure complete treatment of the fluid volume, specifically the fluid near the clamp, the face of the clamp jaws are made of aluminum or stainless steel, thereby preventing any dampening of the waves at the clamp. On the other hand, solid metal clamp jaws would allow the sound waves to propagate through the clamp and into the input reservoir, thus possibly causing excessive sound treatment. To prevent this potential problem, the backs of the clamp jaws are coated with rubber or other sound insulation.

Note that continuous units require no such modifications because the flow is progressively treated.

The second condition on the treatment chamber is that the liquid layer must be relatively thin. There are several advantages of such thin liquid layers. First, a thin layer is necessary to ensure uniform temperatures and uniform cooling. In addition, thin layers also allow the evolved gas bubbles in the liquid to rise quickly to the surface. This is important because rapid bubble rising reduces the time that the ultrasound can induce strong surface oscillations of the bubbles or strong slip-streaming around the bubbles, thereby reducing protein damage. Furthermore, rapid bubble rising also prevents agglomeration of the bubbles to excessive size. Compared to such large bubbles, smaller bubbles are preferable because they provide more uniform treatment, and have less surface oscillation and slip-streaming.

In practice, the plasma is therefore preferably formed into a thin film having a thickness of 2 to 20 mm, preferably 2 to 10 mm, and more preferably then 2 to 4 mm, at least during some part of the application of the ultrasonic energy. Preferably, the plasma is formed into such a thin film prior to the commencement of the application of the ultrasonic energy and maintained in such a thin film during the entire application of the ultrasonic energy.

On the other hand, to obtain adequate treatment volumes, these thin layers must be relatively broad. In the case of batch or semi-continuous mode, the broad surface can be of any desired shape, such as a circle, square, etc., as long as the total resulting volume can be treated uniformly by the ultrasound. The limiting factor here is that ultrasonic waves typically do not produce uniform exposures in containers of water. For this reason, the ultrasonic cleaning industry has developed a number of ways to avoid "hot" and "cold" spots, primarily by using a mixture of frequencies over a narrow bandwidth and by building treatment tanks to dimensions that avoid resonant standing waves. These approaches can be used directly for batch and semi-continuous decontamination units, although the liquid layer in decontamination devices is much more shallow than that commonly used for ultrasonic cleaners.

These approaches, however, must be modified to match the unique geometry required of continuous flow systems. The goal here is to ensure uniform treatment of the flowing fluid. The problem is that moving fluids can follow several different flow patterns. In common experience, such as in rivers, slow moving pipe flows, etc., laminar flow develops such that the center of the fluid moves rapidly, while the fluid near the boundaries is essentially stationary. Although quite simple to develop, such flows must be avoided in decontamination work because the fluid near the chamber walls would thus receive excessive treatment, while the fluid in the center would be essentially untreated.

One means of avoiding this problem is to use a turbulent flow so that eddy currents result in thorough bulk mixing of the fluid. Unfortunately, this approach is not appropriate for protein decontamination for several reasons. First, the Reynolds number $Re=(\rho Vd/\mu)$ where $\rho$ is the density, V is the velocity, d is the diameter and $\mu$ is the viscosity, must be about 1000 for open top flow channels. As such, extremely high flow velocities must be used to achieve turbulence, but it is quite difficult to obtain such velocities in practice. Moreover, even if such velocities could be achieved, a very long processor would be required to produce acceptable treatment times. Finally, even if a high velocity, long residence time chamber could be built, the resulting, prolonged turbulence would damage delicate proteins, thus limiting the range of utility of such a device. For these reasons, turbulent mixing is not appropriate for most protein decontamination work.

The alternative is to use a plug flow, in which all of the fluid moves in bulk through the processor. To generate such a flow, the fluid entering through an inlet tube is first spread out through an expanding section called a diffuser. At the exit of this diffuser, a rectangular geometry is used to provide the plug flow region. For example, this region can be 30 cm wide, 60 cm long, with a fluid depth of 0.4 cm. At the end of this rectangular component, a converging section, which is essentially a reversed diffuser, is then used to guide the flow into an exit tube. This simple geometry is used in ultraviolet flow cells and similar, common laboratory equipment.

For decontamination applications, the ultrasonic sources are placed directly beneath the rectangular section. With this approach, the ultrasound can not only cause decontamination, but can also reduce the effective viscosity of the fluid. This reduction in viscosity is important because lower viscosities reduce the tendency of the plug flow to become laminar, which would otherwise occur over several chamber flow diameters. The net result of this geometry is therefore quite uniform ultrasonic treatment of the fluid.

II. In a second main embodiment, the present invention provides a method for decontaminating plasma which comprises:

(a') a step for the treatment of plasma with ultrasonic energy. In this second main embodiment, the step (a') "for the treatment of plasma with ultrasonic energy" may be carried out in the same way as the step "(a) treating plasma with ultrasonic energy" is carried out in the context of the first main embodiment.

III. In a third main embodiment, the present invention provides a method for decontaminating a fluid, which comprises:

(a) treating a fluid with ultrasonic energy, while degassing the fluid.

Thus, in this third main embodiment, a vacuum is applied to the fluid during the application of the ultrasonic energy.

In this third main embodiment, the ultrasonic energy may be applied to the fluid using the same equipment described above in the context of the first and second embodiments, except for the means of controlling the free radicals. Specifically, in one preferred embodiment of the first and second main embodiments, the ultrasonic energy is applied after the gas above the plasma has been replaced with an inert atmosphere. While quite effective, this approach unfortunately suffers from the material costs for sterile consumables, and the problems of introducing these materials without also allowing contaminants into the system.

An alternative approach is to apply a vacuum to remove the gasses above the liquid being treated with ultrasound (see, *High Intensity Ultrasonic Processor User's Guide*, Sonics & Materials, Inc. Newton, Conn., 1999). In this third main embodiment, the liquid being decontaminated may be any of fluids discussed above. In a preferred embodiment, the fluid is a protein-containing biological fluid, such as plasma. The discussion below explains the method in the context of plasma, but it is to be understood that the method may be applied to any of the fluids discussed above.

The gas above the fluid is effectively removed by applying a vacuum of about 2 to 100 mbar, preferably about 10 to 80 mbar, more preferably 20 to 60 mbar, to the gas above the fluid. The limiting factor here is the evaporation of the solvent: at low enough pressures, the liquid will boil uncontrollably. Since different liquids may require different levels of vacuum, it is preferred that the apparatus be configured such that the level of vacuum can be varied.

The vacuum may be applied by means of a vacuum pump. To avoid oil contamination, the vacuum pump should use a scroll, or other dry, evacuation method.

It is preferred that the vacuum be applied to the gas above the fluid, e.g., plasma, at least at the time of commencement of the application of ultrasonic energy to the plasma. More preferably, the vacuum is applied to the gas above the plasma prior to the commencement of the application of ultrasonic energy to the plasma. Even more preferably, the vacuum is applied to the gas above the plasma: (1) prior to the commencement of the application of ultrasonic energy to the plasma; and (2) and during the application of at least a portion of the ultrasonic energy to the plasma. Of course, ultrasonic energy may be continued to be applied after cessation of exposure to the vacuum.

Beyond eliminating the formation of oxygen radicals at the liquid-gas interface, this vacuum technique also has additional benefits in the decontamination of protein solutions.

The main such benefit is that the applied vacuum reduces the vapor pressure above the liquid and thereby reduces the energy required to induce cavitation. With less applied energy, there is less undesirable protein damage, as would otherwise occur as described above in the first and second embodiments.

Another benefit of applying a vacuum to the decontamination system is rapid, effective degassing of the liquid upon ultrasound treatment. Generally considered to be the simplest application of ultrasound (T. J. Mason, "Industrial Applications of Sonochemistry and Power Ultrasonics," in *Sonochemistry and Sonoluminescence*, edited by L. A. Crum, T. J. Mason, J. L. Reisse and K. S. Suslick, NATO ASI Series C, Kluwer Academic Publishers, Dordrecht, p. 385, 1999), degassing is used in industries ranging from soda and beer production (*Marks' Standard Handbook for Mechanical Engineers*, Tenth Edition; McGraw-Hill, New York, 12_121–12_123, 1996) to hplc oil cleaning. In these and similar applications, the goal is to remove at least some of the gasses dissolved in a liquid product.

It is important to note that there are actually two sources of gas involved in the sonification of a liquid. A general discussion is provided in U.S. Pat. No. 4,597,876. The first gasses to be evolved are the dissolved gasses, in a process referred to as "rectified diffusion" or "gaseous cavitation." In this case, the dissolved gasses are simply trapped in progressively large bubbles because the gasses are forced out of solution more rapidly than they can diffuse back into the liquid. Conversely, the process more often called "cavitation" or "vaporous cavitation" in the sonochemistry literature refers to the formation of bubbles from the sonified liquid phase itself. In terms of energy, rectified diffusion requires only strong vibrations, as readily demonstrated by shaking a soda can. Much greater energy, however, is required to vaporize a liquid to yield what is conventionally called cavitation. As a consequence, sonochemical systems and various ultrasonic cleaners are first "degassed" by extended operation and/or the use of various additives (soaps) before actual processing; otherwise, the dissolved gasses "soften" the sound waves and thus decrease the performance of the ultrasonic device.

Of course, neither long operating times nor soaps are acceptable for decontamination work. As a result, applying sound waves of sufficient energy to plasma yields a combination of rectified diffusion and cavitation of water. Furthermore, rectified diffusion can occur from the dissolved gasses towards the bubbles formed by cavitation. As described in the first and second embodiments, however, it is desirable to keep the ultrasound exposure as low as possible to limit protein damage. Under these conditions, relatively little gas evolution occurs from either source.

Conversely, applying a vacuum reduces the vapor pressure and thus greatly accelerates the growth of gas bubbles from both sources. In addition, the vacuum also removes any gas bubbles that reach the surface. The net result is a liquid with little dissolved gasses; in particular, the liquid thus has little dissolved oxygen. This reduced oxygen concentration results in fewer oxygen radicals due to cavitation, and therefore less protein damage occurs during cavitation.

An enhancement of this process is to use low intensity ultrasound and vacuum to degas the liquid before the higher intensity, cavitation inducing ultrasound is applied. The advantage of this approach is that the dissolved oxygen is thus largely removed before any cavitation occurs, thus minimizing the protein damage.

Because the dissolved gas bubbles tend to collect along the walls of the containment vessel and around interior points of reduced wave action, some existing ultrasonic degassing devices (Polaris Degasser, Polaris Instruments Ltd., Cambridge, UK) use a pulsed ultrasound driver to allow time for the evolved gasses to escape. A further enhancement of this approach is to use progressively longer, higher intensity pulses. The advantage of this approach is that as the degassing process continues, the remaining gasses are more difficult to remove. In addition, the progressive elimination of oxygen allows more power to be applied without radical damage to the proteins.

The net result is that the application of a vacuum allows the initial use of degassing intensities of one fourth or less of the intensities required for atmospheric pressure cavitation. As the degassing continues, progressively higher intensities can be used. At the completion of the degassing process, intensities of more than twice those used for atmospheric cavitation can be used, without significant protein damage from oxygen radicals.

In practice, hydrophone monitoring is used to separate the different steps in this sequence. Specifically, hydrophones record a slight hissing or "frying" sound as the liquid degasses under sonification, followed by a sharp "popping" sound as vapor formation and collapse occurs (A. A. Atchley and L. A. Crum, "Acoustic Cavitation and Bubble Dynamics," in *Ultrasound: Its Chemical Physical, and Biological Effects*, edited by K. S. Suslick, VCH Publishers, Inc., NY, pp. 19–20, 1988). The difference in these two signals is so distinct that it can be recognized by automated equipment, thus providing the basis for activating the different levels of ultrasound described above.

A final additional benefit of vacuum operation is improved feeding of the liquid into the system. In particular, protein solutions such as blood products are easily damaged by pumping, whether by piston or peristaltic arrangements. A vacuum system avoids this problem by drawing in the fluids under a body force. In this regard, a "body force" refers to an action on each component of the entire fluid stream, much like gravity. Gravity feeding, however, requires a sufficient height to provide adequate flows, and this height can sometimes be difficult to arrange in a laboratory setting.

In such cases, vacuum feeding provides a useful alternative. To implement such a system, valves are placed between the source bag or container and the vacuum chamber. Upon activation, these valves thus allow the fluid to enter the processor with minimum transfer damage. To prevent excessive fluid velocities, a flow restrictor is placed in the fluid path.

In addition, these valves can be arranged to match or control the flow through the heat transfer devices described in embodiments one and two. To achieve this effect in practice, the heat transfer unit described earlier is placed directly beneath the source bag or container. This arrangement provides supplemental gravity feeding, as well as complete draining of the input bag for maximum yield. Likewise, the output of the warming unit is placed directly over the inlet of the ultrasonic processing chamber. Two valves are thus used for operation, one valve on each side of the warming bag. Opening the valve between the source bag and the warming bag allows the warming bag to fill to capacity. This valve is then closed, and the fluid is warmed. Next, the valve between the warming bag and the ultrasound chamber is opened, allowing the fluid to enter this chamber under the influence of both gravity and/or the applied vacuum.

There are thus several benefits of vacuum operation; however, vacuum operation also imposes several special requirements. In particular, effective decontamination requires that the vacuum operations must be performed under sterile conditions. One possible solution to this problem is extensive cleaning and decontamination of conventional vacuum hardware. Unfortunately, this approach is expensive and time-consuming, and is thus only of use in very large processors.

A preferred approach is to use a special disposable that can be easily changed between applications. One possible approach is to use a disposable chamber that can withstand a 1 atmosphere vacuum. Such a device, however, would require a great deal of material and would therefore be quite expensive. A preferred alternative is to use a thin disposable plastic liner inside a conventional vacuum chamber made of metal, preferably stainless steel.

In practice, this disposable amounts to a tent arrangement, with an inlet and outlet at opposite sides of the base. At the apex of the tent, a connecting tube provides vacuum access, which thus equalizes the inner and outer pressures. For sterility, an FDA approved filter prevents entry or exit of any pathogens through this tube. To prevent any liquid contamination, a plastic cover is attached to this filter; this cover is opened before use of the unit and closed afterward. Alternatively, a connecting hose with a sterile coupling device (SCD) can also be used for direct vacuum connection. SCDs are also used for the inlet and exits. The entire disposable can thus be sterilized by gamma radiation, autoclave, gas treatment, or any other conventional sterilization technique.

As for materials, the tent can be made of either rigid or flexible plastic. Rigid plastic tents would be clamped to the ultrasound driver for highly effective sound transfer and great structural integrity. Unfortunately, such an arrangement would be relatively expensive and would require a significant amount of storage space. An alternative is a flexible tent with mounting hooks at the corners to maintain the proper shape. This cheaper arrangement is preferable. If desired, the tent can be immersed in a liquid bath to improve acoustic coupling and heat transfer.

With or without this bath, however, all vacuum systems pose a potential risk of aspiration when treating liquids. The standard means of avoiding this problem is to use a vacuum trap to capture any aspirated liquids before they are drawn into the pump. While this approach can be used for decontamination work, a preferred technique is to use separate traps for the plasma container and the vacuum chamber.

Under this arrangement, any contaminated liquid aspirated from the plasma container is thus captured in a separate chamber for disposal. For least expense, this trap is placed beyond the sterile filter so that the trap can be used for multiple cycles. To save space in the vacuum chamber, the trap is located externally. Under this approach, the connection to the plasma chamber is made through a molded insert placed in a recess of the vacuum chamber door seal. Routing the vacuum hose, and any feed lines, through this insert thus allows the disposable to be mounted and dismounted quickly and easily.

The vacuum chamber trap in this approach thus captures any immersion liquid, and also provides an additional safety measure should the plasma container fail.

The vacuum chamber trap also provides a convenient mounting location for the vacuum gauge that is required to monitor the process. Specifically, this gauge must be mounted on the pump side of the trap and sterile filters for protection from any aspirated material.

With this arrangement, the system can be operated in batch, semi-continuous, or continuous mode, as described in the previous embodiments.

In batch mode, the system is evacuated simply by closing the vacuum chamber and turning on the vacuum pump. If the system is not pre-filled, the vacuum then draws the fluid to be treated into the processing chamber. Next, a vacuum sensor and relay activate the ultrasound at the selected vacuum level. Degassing and cavitation are then performed as described above, with the process continuing for a preset time. At the conclusion of this process, the vacuum is released, and the processed material is removed. After fitting a new disposable unit, the system is then ready for another operation.

Semi-continuous operation is performed in a like fashion, except that the filling is done in steps from a large reservoir, and the disposable is not changed at each cycle. In this case, the processed material is collected in a second reservoir at the end of each cycle. Finally, after draining the input reservoir, there will be some residual material left in the processor. To achieve maximum yield, with minimal residual material to pose a biohazard waste product, the treatment unit is then tilted slightly to drain the residual product. This action can be driven by a pneumatic piston, an electric motor, a solenoid, etc.

Continuous operation shares these features, but also requires additional modifications. The first problem is that a continuous flow precludes the use of variable intensity and time pulses of ultrasound on a single batch, as described above. Instead, the ultrasound treatment may be achieved by passing the plasma through sequential pools, each pool having its own ultrasound sources acting at successively higher powers and longer times. Plug flow, as described above in embodiment I, is used in each pool.

Because water is an excellent conductor of ultrasound, however, the pools must be acoustically isolated. This is achieved by having the flow cascade from one pool to the next, with sufficient space so that the fluid thins out to sheets. Next, these sheets flow over a saw tooth pattern of streamers cut from the outlet plate, thus forming a series of ligaments. Under the action of gravity and ultrasound, these ligaments then break up into multiple droplets. The space between these droplets cannot propagate ultrasound, thus providing the necessary acoustic isolation between treatment pools.

Once so treated, it is then necessary to remove the fluid without releasing the vacuum. One means of achieving this removal is to use a peristaltic pump, which is quite useful for those fluids that can withstand the action of such pumps. The limiting factor here is that conventional peristaltic pumps do not work well in vacuum due to heat buildup and lubricant degassing. It is therefore necessary to use either an external driver with an access port through the vacuum chamber wall, or a sealed peristaltic pump.

Another means of removal is to collect the treated fluid in a vessel that is alternately exposed to vacuum and atmospheric environments by a valve and vacuum pump arrangement. Under this approach, opening the valve at the exit of the treatment chamber allows the treated fluid to flow into a collection bag that is also in an evacuated chamber. When this bag is full, the treatment chamber valve is closed, and the vacuum in the collection chamber is released. After the collection chamber reaches atmospheric pressure, the outlet valve is then released. When the collection bag is completely drained, the exit valve is closed, and the collection chamber is pumped back to vacuum conditions. The process is then repeated as necessary. This approach thus provides minimum protein damage during fluid transfer.

IV. In a fourth main embodiment, the present invention provides a method for decontaminating a fluid, which comprises:
 (a') a step for the treatment of a fluid with ultrasonic energy, while degassing the fluid.

In this fourth embodiment, the step (a') "for the treatment of a fluid with ultrasonic energy, while degassing the fluid" may be carried out in the same way as step "(a) treating a fluid with ultrasonic energy, while degassing the fluid" is carried out in the context of the third main embodiment.

V. In a fifth main embodiment, the present invention provides a method for decontaminating a fluid, which comprises:
 (a) simultaneously treating a fluid with at least two different frequencies of ultrasonic energy.

As described above, ultrasound is quite beneficial in the decontamination of liquids, but such treatment has four main problems: protein damage by excessive cavitation, protein damage by excessive heat, long processing time, and low effectiveness.

To overcome these problems, it is necessary to improve the delivery of the ultrasound to the liquid being treated. The limiting factor here is the interaction of the ultrasound with the bubbles in the liquid, which arise from either dissolved gasses or from vaporous cavitation of the liquid itself, as described above. From wave mechanics, the effectiveness of the interaction between these bubbles and the sound waves depends principally on the intensity and the frequency of the ultrasound. As discussed above, higher intensities promote cavitation of the liquid, while lower intensities promote degassification. Depending on the size of the bubble, however, it is also possible for the sound waves to cause the gas bubbles to be absorbed entirely back into the liquid. In this case, the growing bubbles are said to be unstable.

This size dependence arises because the sound waves induce motions in the shape of the bubble wall, as well as motions of the bubble through the liquid. These motions are particularly strong when the frequency of the applied sound matches the resonant frequency of the bubble, as discussed in U.S. Pat. No. 4,597,876. In this patent, a sweep over multiple frequencies is proposed so that the growing bubbles are always subjected to resonance conditions. In practice, however, bubbles of multiple sizes are continuously generated, so that no one frequency is ideal at any time. As such, the expensive electronics and the difficulty in resonance matching of the ultrasound source and the treatment vessel over a broad range of frequencies make this approach undesirable.

Another approach is to use two different frequencies simultaneously (see, CP Zhu, R Feng, YY Zhao, "Sonochemical effect of a bifrequency radiation," *Chinese Science Bulletin*, vol. 25, No. 2 (Jan), pp. 142–145 (2000)). The advantage of this approach is that the combined exposure of two separate sources of greatly different frequencies is significantly greater than the sum of the two sources acting alone. The importance of this result in the context of the present invention is that the use of multiple frequencies provides a means of achieving the same level of cavitation, but with less power applied to the system. With less input power, there is less sample heating, and less intense shear and oscillation around the bubbles. As a result, the material suffers less damage during sonification, while also providing the option of increased total power to improve decontamination and/or to shorten the processing times.

An important condition of such multiple source applications is that the sound must be applied in orthogonal directions to prevent simple superposition. For this reason, Zhu et al used two sources arranged at right angles. For decontamination, this is preferentially extended to three dimensions, so that the waves propagate along the conventional x, y, and z-axes. Note, of course, that such arrangements can be compromised by multiple reflections, so that it is therefore necessary to design the exposure chamber appropriately. This can be done using the standard conventions of acoustics, with the addition of wave scatter at the induced bubbles.

A second consideration in multiple source arrangements is that the frequencies must also be sufficiently great to prevent beating or even prolonged superposition of extrema. For this reason, Zhu et al used frequencies in the low tens of kHz range to the MHz range. The general relationship is that the waves must be separated by at least an order of magnitude in frequency, and preferably also separated in addition by a small constant scale factor. As such, suitable separations can be on the order of 15 or 20 or so.

Using this arrangement for a 3-dimensional system, the lowest frequency band is on the order of 20 to 100 kHz, the next band is on the order of 500 kHz to 1.5 MHz, and the highest band is on the order of 10 MHz. As long as the frequency separation is at least an order of magnitude, these ranges are not extremely critical; the main limitation in this procedure is simply the availability of commercial generating equipment.

While the above work was developed for cavitation, this approach also has significant benefits for degassing. For example, it is known that bubble growth under rectified diffusion is greatly accelerated under conditions that favor microstreaming and asymmetric bubble geometries. It is also known that the Bjerknes force strongly separates bubbles relative to their resonance size. Furthermore, under traveling wave conditions, bubbles can translate rapidly through a sonified volume. Combined with the diffusion shell limitations of rectified diffusion, dissolved gasses are thus released quite rapidly under exposure to multiple sound sources.

In practice, this can be achieved using the same geometry and frequencies required for multiple frequency cavitation. Only the intensity needs to be lowered.

A useful enhancement, however, is to use cavitation power for the highest frequency, with or without pulsing. The evolved gas pockets are quite small, and thus provide nucleation points for subsequent growth by rectified diffusion under the influence of the lower frequency sources.

Finally, it is also possible to extend the above techniques to the reverse process of adding a gas to a liquid. This aspect will be discussed below in the ozone treatment embodiments.

The other conditions and parameters for application of the ultrasonic energy to the fluid may be carried out as described above in the context of the first, second, third, and fourth main embodiments.

VI. In a sixth main embodiment, the present invention provides a method for decontaminating a fluid, which comprises:
(a') a step for the simultaneous treatment of a fluid with at least two different frequencies of ultrasonic energy.

In this sixth embodiment, the step (a') "for the simultaneous treatment of a fluid with at least two different frequencies of ultrasonic energy" may be carried out in the same ways as step "(a) simultaneously treating a fluid with at least two different frequencies of ultrasonic energy" is carried out in the context of the fifth main embodiment.

VII. In a seventh main embodiment, the present invention provides a method for decontaminating a fluid, which comprises:
(a) treating a fluid with ultrasonic energy to obtain a de-oxygenated fluid; and
(b) irradiating said de-oxygenated fluid.

In this seventh main embodiment, the ultrasonic energy may be applied to the fluid in the same way and by using the same apparatus discussed above in the context of the first, second, third, fourth, fifth, and sixth main embodiments. In this seventh main embodiment, the main role of the ultrasonic energy is to affect degassing of the fluid prior to exposure to the radiation.

The purpose of this irradiation is to achieve more effective decontamination than can be achieved by using the previously described ultrasound techniques alone, while still protecting the treated liquids from excessive damage. In terms of prior art, U.S. Pat. No. 3,362,823 describes using ultraviolet light to improve decontamination after ultrasound treatment. Later, U.S. Pat. No. 4,597,876 describes using ultraviolet light on liquids that have been treated with ultrasound and vacuum for degassing purposes. These patents, however, do not address the unique problems of protein protection, as described in the present invention.

As described above, the major limitation in applying radiation, such as UV, gamma, or x-rays, for decontamination is the formation of free radicals of oxygen. Also as described above, one possible solution to this problem is to use some type of scavenging agent, but these agents are expensive and often toxic, and they must therefore be removed before the product can be used.

To avoid this problem, the present invention uses a degassing technology before irradiating the liquid. In particular, this technology is directed towards the removal of oxygen. Without dissolved oxygen, no oxygen radicals can form under subsequent irradiation, thereby sparing the proteins being decontaminated.

There are several alternative means of degassing liquids in general industrial practice. For example, freezing and boiling are commonly used for degassing, but both of these processes cause severe protein damage. It is also possible to use tubes or membranes as separation media, with or without a vacuum assist. Because these media are currently expensive and clog readily, however, their use is somewhat restricted for most protein solutions. There are also several mechanical devices, such as static mixing nozzles (Upchurch Scientific, Oak Harbor, Wash.) or rotor based systems (Walter P. Nold Company, Natick, Mass.). The mechanical action of such devices, however, is quite damaging to delicate materials such as proteins. Alternatively, the oxygen alone can be displaced by other gasses, but this is expensive and time consuming. For these reasons, vacuum ultrasonic degassing techniques have been developed, particularly in terms of treating small volumes of expensive reagents (Polaris Degasser, Polaris Instruments Ltd., Cambridge, UK).

As described in embodiments I-VII above, however, applying ultrasound to protein systems results in some undesirable damage to the material being treated. In particular, embodiment III describes the protein damage expected during degassing prior to ultrasound decontamination.

This raises the question of just how much oxygen removal is necessary prior to irradiation. In this regard, chemical quenching agents can reduce, but not eliminate, radical damage. The underlying physical principle is that the incoming photon splits the dissolved oxygen molecule into two radicals, but these radicals may not be in immediate contact with a quenching agent. The radicals can therefore contact and damage some protein molecules before eventually being inactivated. It should also be noted that in addition to radicals, there are other products of irradiated oxygen that are less reactive, but still damaging. Called "reactive oxygen species," these high energy oxygen forms are bound with other molecules, notably hydrogen. Depending on the type of the quenching agent, and the type of the oxygen species, quenching agents may have little or no inactivating effects on such species. The net result is that quenching agents do not eliminate all oxygen effects, leaving some radical damage and some damage due to other reactive oxygen species. Because quenching agents are known to be effective even with these limitations, it is therefore not necessary that the new degassing technology remove all of the dissolved oxygen to be effective in protecting the proteins during irradiation.

In practice, the actual amount of residual dissolved oxygen must be determined on an individual basis. One factor to be considered in this determination is the damage that the degassing process itself inflicts upon the proteins. When performed under the procedure described above, however, most materials suffer little or no damage during degassing, at least for moderate oxygen removal. At progressively lower oxygen concentrations, however, there is the possibility of some protein damage, especially for labile clotting factors. Conversely, there is less protein damage due to radical formation at such lower oxygen concentrations. Finally, progressively more time and expense are required to reach progressively lower concentrations. The net result is that there are several competing factors to be considered in any practical application.

Applying these considerations to blood products, it is generally helpful to keep process losses at less than 10%, and preferably less than 5%, which is more or less the accuracy of the measuring instruments. Before processing, blood products have normal oxygen levels on the order of several ppm; the actual concentration depends on the individual product, the temperature, the type of storage bag, the length of storage, etc. With the previously described degassing techniques, the dissolved oxygen concentration can easily be decreased to about 1 to 2 ppm in 5 minutes or less, depending on the starting temperature and oxygen concentration. To achieve concentrations in the hundreds of ppb range, however, the processing time increases to about 30 minutes. As will be described more fully below, it is possible to treat the degassed material with several different radiations. The result of such irradiation is about 50% protein damage for untreated plasma. The protein damage is less than 10% for the 1 to 2 ppm samples, and there is progressively less damage, down to the limit of machine accuracy, in the ppb dissolved oxygen levels.

Of course, at dissolved oxygen concentrations in the ppb range, only very few oxygen radicals are formed under irradiation. Under such conditions, it is possible that these few oxygen radicals would be most damaging to the most sensitive components, which are typically the pathogens themselves. If so, the residual oxygen may thus actually have a slight benefit in terms of decontamination.

With or without such an effect, the target dissolved oxygen range for blood products is preferably 10 to 3000 ppb, more preferably 100 to 2500 ppb, and most preferably 500 to 2000 ppb.

Incidentally, it should be noted that in the determination of these limits, conventional electric resistance-based dissolved oxygen meters are not accurate because the samples are too small and there is inadequate flow to ensure representative reactions at the electrodes. This flow limitation is particularly important in the ppb range, where a significant amount of liquid must be tested in order to obtain enough oxygen for an accurate result; otherwise, false low readings will occur as the local environment is depleted of the few oxygen molecules present. Because of these limitations, an optical absorption meter (Model VVR, CHEMetrics Calverton, Va.) with appropriate dilution factors should therefore be used to determine the actual dissolved oxygen concentrations.

Having thus determined the means and the appropriate level of degassing, the remaining concern is the radiation to be used for the subsequent decontamination. Specifically, it is necessary to select the type of radiation, the required dosage of this radiation, and the means of applying this radiation to the material to be treated.

In this regard, gamma radiation is commonly used in the decontamination industry, typically from Cobalt-60 or Cesium-137 sources. In either case, the required dosages are known for most pathogens, but for general decontamination work, a dosage must be selected that will treat most pathogens, without causing excessive protein damage. An appropriate test virus must therefore be selected; the conditions that inactivate this virus are then considered to be adequate for other pathogens as well.

A particularly useful test subject is parvovirus. This small, non-enveloped virus is quite difficult to inactivate, thus assuring destruction of less robust viruses such as HIV. In its porcine form, parvovirus is harmless to humans, and is therefore easy to handle in the laboratory. Furthermore, because of its potential damage to a developing human fetus, and because of its ease of transmission by transfusion, the human form of this virus is of clinical significance. For these reasons, parvovirus is therefore commonly used as a benchmark for inactivation technologies (SI Miekka et al, "New methods for inactivation of lipid-enveloped and non-enveloped viruses," Haemophilia 1998 July; 4(4):402–8).

On the basis of this benchmark, the appropriate dosage range for gamma radiation of blood products is between 1 to 100 kGy (kiloGray), more preferably 2 to 60 kGy, and even more preferably 4 to 40 kGy.

In practice, it is quite easy to obtain such dosages with gamma radiation because the high energy photons are quite penetrating, and can thus be readily used without concern for shadowing or incomplete local exposures. In the present invention, this capability allows great flexibility in the design of the exposure chamber. One option is to irradiate the liquid while it is still in the vacuum chamber. In this case, the radiation source is placed outside the sterile tent arrangement described above. As such, the source can be placed inside the vacuum chamber, or outside the vacuum chamber with access through a thin, low-absorption window.

Another option is to irradiate the liquid after the chamber vacuum has been released. In this case, a valve is placed on the tube leading to the processing tent. Closing this valve after the tent and vacuum chamber have been evacuated and sonified dig allows the chamber to be returned to atmospheric conditions, while still maintaining a vacuum on the processed material. As such, the flexible bag then simply collapses upon the essentially incompressible fluid being treated. The advantages of this approach include very simple shielding and control arrangements. The only constraint is that the treatment bag must be relatively impermeable to oxygen so that the irradiation is completed before the dissolved oxygen concentration rises to unacceptable levels by diffusion from the surrounding air. Alternatively, the irradiation must be completed before significant amounts of oxygen pass through less impermeable bags.

In either of the above options, batch and semi-continuous operations can be readily achieved by simply irradiating the target for a specified time, with continuous monitoring of the applied radiation by conventional detectors and recorders. For continuous operation, however, the previously described plug flow must be constrained in a closed channel arranged so that the fluid is continuously rising in height. This constraint ensures that all of the fluid has sufficient residence time in the exposure chamber to receive full treatment; otherwise, the fluid could flow out of the channel too rapidly under the force of gravity. The driving force for the upward flow can be a pump, or a gravity head from the higher-placed vacuum chamber.

The type of force is particularly important for the cellular components of blood that are readily damaged by most mechanical pumps, as noted above. In this regard, gravity feeding thus provides little or no such damage. For this reason, the present invention is well suited for the leukoreduction of cellular blood components. In addition, leukoreduction by gamma irradiation avoids the problems of filter clogging, long processing times, high expense, and the related difficulties that complicate existing, filter-based technologies. Furthermore, an additional advantage in the present invention is that degassing prior to leukoreduction prevents oxygen radical attack on the walls of the leukocytes, and thus prevents the leakage of the cellular contents that are quite detrimental to erythrocytes. Note in this application that although cellular blood components require oxygen, these cells can survive in an oxygen-depleted environment long enough (several minutes) for decontamination. Oxygen can then be supplied to the fluid after the irradiation is completed. The above advantages of gamma exposure are particularly significant in terms of the recent recommendation for universal leukoreduction (Wall Street Journal, "Federal Panel Hears Debate On Filtering All Donated Blood," Jan. 25, 2001).

Unfortunately, one potential problem in the above decontamination processes is the formation of aggregates, particularly from albumin, under gamma irradiation. These aggregates are undesirable because they not only reduce the amount of usable protein, but they also require a separate, time-consuming step for removal. In the present invention, such aggregates are therefore destroyed by ultrasound. The underlying principle here is that ultrasound can be used to agglomerate or disperse solids in a liquid, depending on how the sound is applied. In the present invention, the irradiation chamber is therefore sonified uniformly along the chamber length during irradiation, thereby disrupting any small aggregates as soon as they form.

Another potential problem with gamma irradiation is the formation of reactive species from molecules other than oxygen. In particular, gamma radiation has sufficient energy to dissociate and/or excite water molecules. To reduce this effect, protein concentrates can be used. PCT Application number WO 0016872 describes a procedure for generating such concentrates. Because concentrates contain relatively little water by definition, the number of reactive water species is reduced proportionately, compared to the original protein solutions.

Being an electromagnetic radiation of the same energy as gamma radiation, x-rays can also achieve all of the above benefits. Unlike the nuclear decay sources used for gamma irradiation, x-rays are instead generated by high voltage, electron acceleration sources. Because of the energy requirements and maintenance costs of such accelerators, however, gamma radiation is currently the preferred of these two radiations for decontamination work.

Unfortunately, both gamma and x-ray sources are not only relatively expensive, but they also require strict shielding, licensure and other constraints.

For these reasons, UV sources are more commonly used for decontamination. There are four types of UV radiation, which in terms of increasing energy are UVA, UVB, UVC, and VUV. UVA and UVB are the relatively weak radiations associated with sun exposure. Being too weak to induce radical formation, these radiations unfortunately require some type of light-activated chemical to induce decontamination. As described above, however, the intent of this invention is to avoid the costs of any such chemicals, so these radiations are not useful here by themselves. Conversely, VUV, or vacuum ultraviolet, is much more energetic, being on the border of soft x-rays in terms of energy. VUV, however, is difficult to generate and is absorbed so readily that it is not practical for decontamination work.

UVC is therefore the preferred form of ultraviolet radiation in the present invention, particularly the UVC produced by mercury sources. These sources are useful because they emit light mostly at about 254 nm. Because these sources thus have relatively low emissions at wavelengths less than the 185 nm threshold required for ozone generation, they produce little of this undesirable gas. More importantly, however, this wavelength is in the middle of a local minimum of absorption that exists in the range of 250 to 260 nm for most proteins, but both DNA and RNA have a local absorption maximum in this range. For this reason, mercury lamp emissions thus selectively attack the DNA and RNA found in most contaminants, while sparing the other proteins in the material being treated. In particular, this selectivity is most useful for treating blood components because, as discussed earlier, most blood components lack the genetic materials DNA and RNA.

The exception is that leukocytes do contain these materials, but in this case, UVC irradiation is still of benefit in terms of leukoreduction. Specifically, in this application, UVC has all of the clinical advantages described above for gamma rays, as well as the advantage of selective protection of the surrounding proteins.

Having thus selected UVC as the ultraviolet radiation of choice, appropriate dosages must then be determined. There is a great deal of data on UVC dosages in terms of water purification and food processing, but protein solutions have unique requirements, notably regarding the types of contaminants.

In terms of blood products, parvovirus is of particular interest, as described above. Specifically, H. Sugawara has recently summarized the current state of the art of UVC inactivation of this virus in regard to plasma products (H. Sugawara et al, "Inactivation of parvovirus B19 in coagulation factor concentrates by UVC radiation: assessment by an in vitro infectivity assay using CFU-E derived from peripheral CD34+cells," Transfusion 2001 April; 41(4): 456–61).

The net result of this and similar studies is that the UVC irradiation should preferably be on the order of 1 to 10,000 $J/m^2$, more preferably 10 to 5,000 $J/m^2$, and even more preferably 100 to 3,000 $J/m^2$.

Having thus determined the appropriate dosages, the next concern is how to obtain this irradiation with minimum protein damage. The problems to be addressed are uniformity of exposure, excessive heat, the formation of aggregates, and the recovery of pathogens.

Beginning with the uniformity of the exposure, several dimensions must be considered. First, the treatment chamber must be of uniform thickness, as discussed above for the ultrasound system. Also as discussed for ultrasound systems, moving systems must have plug flow as described in first main embodiment.

Unlike ultrasound systems, however, the depth of the treatment chamber is critical for UVC systems. The underlying problem is that the optical absorption in the treated liquid follows an exponential curve according to Beer's Law. As such, the exposure on one side of the treatment chamber can be much less than the exposure on the other side of the chamber, even for relatively thin units. In the present invention, the UVC irradiation is therefore preferably applied from both sides of the treatment chamber. Under this arrangement, the exposure sum from the two opposing sources is thus nearly constant for moderate target widths.

In addition to the liquid, the walls of the treatment chamber can also absorb UVC. For this reason, these walls must also be of uniform thickness, and of UVC transparent material, preferably fused quartz.

Of course, uniform exposure also requires at least some uniformity in the UVC source itself. In this regard, spot lamps and tubes generate only relatively small zones of uniform exposure. Conversely, grid lamps, which consist of long, thin, tightly coiled tubes, yield much more uniform exposures. Such lamps (Model LF 180S, UVItec, Cambridge, UK) are therefore used in the present invention.

In addition to the above shape uniformity, the lamps must also have reasonable uniformity over time. The fundamental problem here is that all UV equipment is subject to "solarization," which is essentially degradation due to the high energy of the generated photons. As a consequence, the applied dose can be inadequate for decontamination if a simple timing procedure is used to control an aged lamp. It is therefore preferable to use an integrating monitor (Model RX 003, UVItec, Cambridge, UK) to ensure that the specified exposures are actually maintained over the lifetime of the lamp. Furthermore, placement of such a monitor beside each lamp thus ensures that a bank of lamps functions as intended. In this case, at least one monitor should also be placed opposite at least one lamp, beyond the liquid being treated, to ensure that the appropriate absorption levels are maintained; this is a particularly important consideration for blood products, in which the optical properties often differ greatly from sample to sample.

Unfortunately, all UVC lamps produce significant amounts of heat, and while grid lamps produce relatively little heat compared to their quite high UVC intensity, their heat is still a problem. Part of this heat can be controlled by fan-assisted convection over the lamps. This approach, however, does not limit the infrared component from the lamps, which is absorbed directly within the target. For this reason, a flow or spray of water is therefore used to cool the target, since water is a very poor absorber of UVC light. To prevent this cooling water or spray, or any leaking contaminated fluid, from falling into the lamps and causing electrical problems or breakage, the treatment module and lamps should be oriented vertically. This geometry also aids the maintenance of controlled flow for continuous systems, as discussed earlier.

Even with uniform UVC exposure and two cooling mechanisms, there is nevertheless a possibility of forming protein aggregates at isolated points in the treated liquid. As described above for gamma irradiation, however, these aggregates can be eliminated by exposure to ultrasound.

The final problem with UVC treatment is that after the sources have been turned off, there can be some recovery of the pathogens, apparently by an inherent repair mechanism. Recent work with discharge lamps, however, (see, WH Cover, "Effect of Broad Spectrum Pulsed Light (BSPL) on Platelet Function," Cambridge Healthtech Eighth Annual Symposium on Blood Product Safety, Feb. 4–7, 2002) indicates that other wavelengths of light can inhibit such recovery. Unfortunately, discharge lamps also produce a great deal of heat. Since mixtures of UVB and UVA are known to be more effective than either acting alone, and since the UV wavelengths are the most energetic in the emission of discharge lamps, a preferred approach is to include UVA and/or UVB sources in the treatment protocol to suppress pathogen repair. Since these wavelengths do not induce radical formation, their inclusion thus causes no intrinsic protein damage, and their infrared contribution can be readily handled by the existing cooling system. In addition, any polymer that is transparent to UVC is also transparent to UVA and UVB, so the design considerations reduce to only building a system capable of UVC treatment.

With the above considerations, UVC systems can be built for a variety of operating conditions and contaminated liquids. The overall approach is similar to that described above for gamma irradiation systems, and can thus be used for batch, semicontinuous, and continuous operation. The major difference is the limited penetration capability of UVC versus gamma irradiation, which leads to several concerns in regard to bag design.

The primary consequence of this limited UVC penetration range is that the disposable treatment bags must be made of UVC transparent material. In particular, Teflon® and similar fluoropolymers are quite transparent to UVC, and are thus the preferred materials; however, they are somewhat expensive and permeable to oxygen. For these reasons, thin films of other polymers, such as ethyl vinyl acetate, can be laminated with Teflon® to provide a reasonably cheap, strong, oxygen impermeable, UVC transparent container. Also, performing the exposure rapidly ensures that the decontamination is complete before significant amounts of oxygen can diffuse into the system.

Another problem in terms of treatment bags is that Teflon® and other fluoropolymers are difficult to seal with the inclusions that are required for sterile blood product ports and vacuum access. This problem is of little consequence when the degassing and UVC exposure processes are done in the same bag. On the other hand, when these processes are performed in separate bags, the degassing step should be done in any cheap, easily sealed bag material such as PVC, while the UVC exposure should be done in a higher cost, harder to seal, but UVC transparent, bag.

Yet another bag problem is that the access ports and connecting tubes are typically not UVC transparent, and can thus shield the pathogens from UVC exposure. The solution to this problem is similar to that described in embodiment I for ultrasound feed ports, except in this case any clamping must be done by UVC transparent materials to prevent shading effects. For example, the clamps can be made of fused quartz, but for greater mechanical strength, polymers such as Teflon® AF are preferred. Yet another alternative is to use stainless steel or other metallic pincers, tapered to reduce end shadows. In this case, the clamping should be done in a section of the bag that is fully illuminated, and also elevated to drain the fluid away from the clamping location. Under this arrangement, the available light will be minimally attenuated, thereby providing maximum treatment at the clamp location.

The final bag problem is that for relatively large treatment volumes, the thickness must remain small, and thus the surface area must be large. Beyond the matter of costs, this restriction also causes substantial hydrostatic pressures, particularly for the vertically oriented systems described earlier. One alternative is to use very heavy quartz plates to contain the treatment bags, but this approach is expensive and causes undesirable attenuation of the UVC light. It is therefore preferred that the center sections of the bags be joined front to back, thus reducing the loading on the fused quartz plates. In addition, it is also preferred that the boundary seal of the treatment bags include holes to match registration pins. These pins can be either permanently mounted in the periphery of the treatment chamber, or mounted in a plastic frame that allows for rapid insertion and removal of the bag assembly.

These considerations are particularly important for erythrocyte treatment. In this application, the strong attenuation of UVC by the heme groups in the erythrocytes restricts the fluid path in the treatment chamber to a thickness of about 30 to 60 microns. Even though this layer is thus very thin, the associated hydrostatic pressures are nevertheless still quite high. The joints in the center are thus not only useful in this application, but they also provide a means of mixing the flowing liquid. This mixing is achieved by staggering several consecutive joints, thereby splitting the fluid flow accordingly.

Unfortunately, as described earlier, such flow mixing is relatively weak except under the turbulent conditions that are quite detrimental to blood proteins. As such, whatever mixing is available by the addition of flow restrictions is inadequate to prevent the shading effect among multiple erythrocytes. For this reason, U.S. Pat. No. 6,219,584 describes vibrating the treatment chamber.

In the present invention, ultrasound is used to provide extremely effective vibration. The underlying principle is that ultrasound can agglomerate or disperse solids in a liquid, as noted earlier in the discussion of aggregate treatment. For maximum effectiveness in the present invention, the vibrating ultrasound is provided by a horn in direct contact with the treatment bag. Specifically, this horn should be in contact with the bottom of the treatment bag, thus ensuring adequate vibration for even partially filled bags. This approach thereby avoids vibrating the entire treatment chamber, which would be difficult due to problems in impedance matching, as well as possible chipping of the expensive fused quartz plates.

As noted in U.S. Pat. 5,997,812, the addition of ultrasound to a liquid being irradiated by UV not only improves mixing, but also improves the "killing effect of UV radiation."

VIII. In an Eighth Main Embodiment, the Present Invention Provides a Method for Decontaminating a Fluid, which Comprises:
   (a') a step for the treatment of a fluid with ultrasonic energy to obtain a de-oxygenated fluid; and
   (b') a step for the irradiation of said de-oxygenated fluid.

In this eighth main embodiment, the step (a') "for the treatment of a fluid with ultrasonic energy to obtain a de-oxygenated fluid" may be carried out in the same ways that step "(a) treating a fluid with ultrasonic energy to obtain a de-oxygenated fluid" is carried out in the context of the seventh main embodiment. In addition, the step (b') "for the irradiation of said de-oxygenated fluid" may be carried out in the same ways that step "(b) irradiating said de-oxygenated fluid" is carried out in the context of the seventh main embodiment.

IX. The Inventor has Further Discovered, in a Ninth Main Embodiment, that such Fluids may be Effectively Decontaminated by a Method Involving:
   (a) treating a fluid with ultrasonic energy to obtain a de-oxygenated fluid; and
   (b) contacting said de-oxygenated fluid with a pulsed electric field.

In this ninth main embodiment, the de-oxygenation of the fluid may be carried out as described above. After the fluid has been de-oxygenated, it is then contacted with a pulsed electric field (PEF).

The underlying concept of PEF is to use short pulses (tens of microseconds) of very high voltage (tens of kV) electric fields to decontaminate temperature sensitive materials. This approach is commonly used in the food industry, particularly for bacteria, parasites, etc. The limiting factor is that the target pathogen must be sufficiently large to establish a voltage gradient. While this limitation effectively excludes pathogens on the size of viruses or smaller, many pathogens can nevertheless be treated by PEF.

A major limitation of PEF is that the sample may break down during treatment. In particular, dissolved gasses readily cause breakdown. For this reason, Q. H. Zang has described the benefits of degassing apple cider prior to PEF treatment http://www.fst.ohio-state.edu/FS/pef/sld027.htm, slide 27/91 (1998). Under this approach, many more pulses can be applied to the sample before electrical breakdown, thus improving decontamination without product degradation.

This embodiment relies on a synergistic effect between the application of ultrasonic energy and PEF. The underlying principle of PEF is that the various fields can act on charged species, or even upon polar molecules.

Constant electric and magnetic fields are the simplest to analyze and implement. Beginning with electric fields, there is a long history of applying a current through a contaminated liquid to affect some kind of cleaning treatment. The overall approach is simply to put two electrodes on opposite sides of a pool of liquid and then apply electricity.

The essential problem of this approach is that electrochemical reactions, primarily at the electrodes, can contaminate the product. This is a critical concern for biological materials, such as plasma, that will be used for medical treatment.

A new means of avoiding this problem is to use a salt bridge across a sterile filter to couple the electrodes to the fluid to be treated. In a further enhancement, a thin tube leads from the filter and salt bridge, extending to the sides of the treatment bag. For further protection, a flow restriction is placed at the juncture of the tube and bag. After treatment, this tube is then heat sealed at the flow restriction, and the filter and salt bridge may then be discarded.

Under this arrangement, undesired compounds are first trapped at the leading edge of the salt bridge. Any residual compounds that escape this trap are then caught in the connecting tubes before they reach the bulk of the fluid.

An immediate extension of the constant electric field is the pulsed electric field, or PEF. PEF typically involves very high voltages, on the order of 20 kV, but very short duration. In particular, PEF and ozone are known to have a synergistic effect (R Unal, J G Kim, and A E Yousef, "Inactivation of *Escherichia coli* O1 57:H7, Listeria monocytogenes, and Latobacillus leichmannii by combinations of ozone and pulsed electric field," *J. Food Prot.*, June; 64(6), pp. 777–782 (2001)). In this embodiment, PEF is therefore combined with the above salt bridge and tube arrangement.

Like constant electric fields, strong magnetic fields have also been used for several decades in decontamination work. Recently, strong magnetic fields have been combined with UV irradiation (U.S. Pat. No. 5,997,812). This technique, however, does not apply well for biological systems without magnetically susceptible materials.

The most advanced form of electric and magnetic treatment is of course the electromagnetic field, as noted above for UV, gamma and x-rays. Synergistic effects with ozone have also been noted (MW Byun et al, "Gamma irradiation and ozone treatment for inactivation of *Escherichia coli* O157:H7 in culture media," *J. Food Prot.*, June; 61(6), pp. 728–730 (1998)). The net result is that the new technology has multiple opportunities for synergistic effects. In particular, ultrasound and PEF can be applied either together or separately during either or both the UV and the ozone steps described below.

In terms of plasma treatment in the new technology, the preferred location to apply PEF is thus immediately after the degassing step. As such, PEF can be done before, during, or after UVC or gamma irradiation (as described below). In particular, it should also be noted that the improved speed of ultrasonic vacuum degassing is of immense use in the PEF treatment of foodstuffs.

X. The Inventor has also Discovered, in a Tenth Main Embodiment, that such a Fluid may be Effectively Decontaminated by a Method Involving:
   (a') a step for the treatment of a fluid with ultrasonic energy to obtain a de-oxygenated fluid; and
   (b') a step for contacting said de-oxygenated fluid with a pulsed electric field. In this tenth main embodiment, the step (a') "for the treatment of a fluid with ultrasonic energy to obtain a de-oxygenated fluid" may be carried out in the same ways that step "(a) treating a fluid with ultrasonic energy to obtain a de-oxygenated fluid" is carried out in the context of the ninth main embodiment. In addition, the step (b') "for contacting said de-oxygenated fluid with a pulsed electric field" may be carried out in the same ways that step "(b) contacting said de-oxygenated fluid with a pulsed electric field" is carried out in the context of the ninth main embodiment.

XI. In an Eleventh Main Embodiment, the Present Invention Provides a Method for Decontaminating a Fluid, which Comprises:
   (a) treating a fluid with ultrasonic energy to obtain a de-oxygenated fluid; and
   (b) contacting said de-oxygenated fluid with ozone.

As described earlier, decontamination is best achieved by applying multiple, independent processes. Under this approach, the pathogens that escape one decontamination technique may not escape a second, or third, technique etc. In addition, any given technique can destroy only a limited number of pathogens before it also causes a significant amount of protein damage, so it is preferable to use multiple techniques at partial power instead of one technique carried to extreme limits. It is therefore desirable to integrate the above technologies with yet another independent technique. A particularly useful such technique is ozone exposure.

Ozone is a triatomic molecule of oxygen, while the common form of oxygen is diatomic. As a result, ozone is an unstable molecule and is thus extremely reactive. In particular, this high reactivity makes ozone an extremely strong decontamination agent. The underlying mechanism is that ozone rapidly attacks the complicated protein structures that pathogens require to propagate, thus causing rapid inactivation. An additional benefit is that after it has reacted, ozone then reverts to non-toxic molecules that are naturally present. As such, ozone and its products do not have to be removed from the treated material, thus saving a separate, expensive, and time-consuming step that is typically required for other decontaminating agents.

For these reasons, ozone has been used for many years in a variety of decontamination devices. Some of these applications involve treatment of a given area or volume by gas exposure, such as a room or a device inside an enclosure. While these applications are quite numerous, the main concern of the present invention is liquid treatment, whereby the ozone is absorbed into an aqueous solution. Such aqueous solutions, in turn, have many particular applications. In this regard, the most common use of ozone decontamination is for processing water, including both potable water treatment and pollution control. While some aspects of the present invention are applicable to such processes, however, the main application here is the decontamination of biological products, particularly blood products. But even in this somewhat restricted discipline, several such devices have already been disclosed.

For example, U.S. Pat. No. 4,632,980 discloses an ozone blood treatment device, in particular a technique for controlling damage to blood products while preferentially attacking enveloped viruses. There are, however, several problems with this patent, beginning with the restriction to enveloped viruses. Specifically, while enveloped viruses such as HIV were of primary concern in the early 1980's when this patent was under development, the subsequent development of advanced viral testing and the emergence of more non-enveloped viruses have greatly changed the needs of the blood industry. Another problem is that although this patent mentions pH, the pH of blood and blood products depends strongly on the choice of anticoagulant, and as discussed later, the pH strongly affects the behavior of dissolved ozone. Another significant problem is that the disclosed device uses a glass roller chamber, but since the clotting sequence can be initiated within glass vessels, such materials should therefore not be used for blood products. Furthermore, rollers of any material are inherently slow. Finally, the glass vessel and the associated seals would be expensive, difficult to store, and difficult to destroy once used.

Another ozone device for blood treatment is disclosed in U.S. Pat. No. 5,709,992. The main feature of this patent is a method for protecting red blood cells from ozone damage by adding reducing enzymes. As discussed below, however, red blood cells already have some intrinsic protection. Furthermore, as noted many times above, in blood work the added materials are commonly removed before use of the treated material, at considerable time and expense. Finally, the 48 hour processing time is simply too long to be accepted in normal blood bank operation.

An alternative approach is described in U.S. Pat. No. 5,882,591, which discloses a spraying system. The advantage of this system is that the finely divided spray promotes rapid deactivation. There are, however, several possible problems with this approach. In particular, while the inactivation of the contaminants in the small droplets is indeed quite rapid, the overall process of converting a large volume of fluid into a spray is not rapid. As such, the total process is too slow to be used in a blood bank environment. Another concern is the mechanical damage due to the spraying process, which increases as the droplet size decreases. Finally, there is also the concern of the confinement of the spray itself: aerosols of potentially contaminated blood products are usually avoided because of the danger of infection. While a number of traps could be developed, they would be expensive and not completely effective. In a large blood processing facility, the cumulative air loading would thus be quite dangerous.

All of the above techniques are essentially in vitro applications, in which the treated material is collected for later use. However, ozone can also be used for XCT, or extracorporeal treatments, as disclosed in U.S. Pat. No. 6,027,688. In this device, blood is withdrawn from the patient, treated, and then re-infused, with the intent of reducing the HIV burden. One problem is that this device is quite complicated and would thus be expensive to buy and operate. In addition, this device also has a glass treatment tube, which, as discussed above, could cause severe clotting, and thus lead to pulmonary embolism and death. Finally, even with long processing times, the disclosed 99% (or log 2) viral reduction is quite small compared to the log 6 or 7 that is desired.

The net result of the above and similar works is that ozone is a quite effective decontamination agent for protein solutions, but a major limitation is the overall speed of this process. It is therefore necessary to develop a faster ozone treatment technique. This development can be realized using basic ideal gas laws.

The first such consideration is the concentration of the input ozone gas: higher concentrations are preferable because they yield more collisions among the reacting species, and thus yield more product in less time. The limiting factor here is that gaseous ozone concentrations of greater than 20% are explosive. At lesser concentrations, a number of practical concerns limit the effective concentrations that can be achieved. The main such concern is that ozone is so reactive that it cannot be stored for prolonged time periods. Instead, ozone is typically generated at the site where it is to be used.

There are three major means of ozone generation: ultraviolet light exposure, corona discharge and chemical reaction (*Handbook of Ozone Technology and Applications*, Volume One, R. G. Rice and A. Netzer, Eds., Ann Arbor Science, The Butterworth Group, Kent, England, 1982).

Ultraviolet light sources function by first splitting diatomic oxygen molecules into singlet oxygen, which then reacts with other diatomic molecules to form triatomic ozone. Although this process is the origin of the earth's ozone layer, ultraviolet exposure is inefficient. The underlying problem is that while certain frequencies of light are quite effective in generating ozone, other frequencies are almost as effective at dissociating the formed ozone. As a result of these competing processes, UV units are limited to concentrations of less than 1%. Although UV sources are quite clean and easy to control, this low ozone concentration limits their use in decontamination work.

An alternative ozone generation technique is corona discharge. In this process, oxygen is passed through a channel bound by high voltage electrodes. The resulting discharge ruptures the diatomic molecules, and some of the resulting, high energy single oxygen molecules react with some of the neighboring oxygen molecules to form ozone. Typical yields are in the range of 1 to 15% by volume ozone.

Unfortunately, there are several problems with corona discharge systems. One such problem is that the feed gas may also contain nitrogen, water vapor, or other gasses. If so, there is a possibility that molecules other than oxygen and ozone may contaminate the product. Medical applications of discharge systems therefore typically use high grade oxygen as a feedstock, but this entails additional costs. In addition to this gaseous contamination, there is also the possibility that degradation of the electrodes may introduce solid contaminants into the product; therefore, expensive filters are required. Furthermore, the eroding electrodes also produce electromagnetic noise, which is undesirable in a medical environment. Yet another problem with discharge systems is that the resulting gas is so hot and dry that it can damage the proteins being treated. Finally, electric discharges are difficult to control, particularly at partial load operation. For these reasons, corona discharge units can be used for decontamination work, but a great deal of conditioning is necessary.

An alternative approach is to generate ozone by various chemical reactions. For example, U.S. Pat. No. 5,709,992 discloses one such technique for adding activated ceramic particles directly into the pool to be treated. A much more promising approach, however, is to use an electrochemical technique. For example, U.S. Pat. No. 5,989,407 by Lynntech, Inc. (which is incorporated herein by reference) discloses a device that produces ozone at concentrations of 10 to 15%. This device works on the principles of electrolysis of water, thereby avoiding the cost of expensive medical grade oxygen as a feedstock while also avoiding the problem of electromagnetic noise. In addition, the ozone produced by this device is self-pressurizing, relatively cool, and fully humidified.

Because of these advantages, electrochemical units are currently the preferred ozone sources for the present invention. In the following, several unique features of electrochemical ozone generators are described in detail, along with the modifications and extensions that are necessary that are necessary to exploit these features in practice.

Beginning with self-pressurization, the underlying ideal gas law here is that all gasses, including ozone, are much more soluble at elevated pressures. As such, an increase in pressure therefore results in more ozone in solution, and thus more rapid, more effective treatment.

To achieve these benefits, the ozone must be either generated at elevated pressure or generated at lower pressure and then compressed. Because compressing ozone is difficult and expensive, the above-noted ability to generate ozone at pressure is a major advantage of electrochemical ozone units.

Unfortunately, the available electrochemical units are not yet capable of generating ozone at pressures beyond about 50 psi. It is therefore necessary to compress the gas to reach higher pressures. The preferred means of compressing ozone is a diaphragm pump (BA series, Fluitron, Ivyland, Pa.). Diaphragm pumps are useful because they have no seals that can be destroyed by ozone contact, and the entire flow path can be constructed of easy to clean, chemically inert materials. The limiting factor in the design of such compressors is that ozone decomposes at higher temperatures. It is therefore necessary to start with the ozone as cold as possible, and then compress the ozone through multiple stages. At each stage, the temperature should not exceed about 40° C. To achieve this limit, the maximum compression ratio in each stage can be calculated by the standard adiabatic ideal gas laws. Water cooling of the compression heads thus ensures that the peak temperatures are kept well below the theoretical upper limit. While effective, such compressors are quite expensive, and will be discarded as advances are made in electrochemical generation. In the meantime, the output from the existing generators provides a cool, partially compressed feedstock. For example, the 50 psi output from an electrochemical ozone generator can be fed directly into a two stage diaphragm pump, with each stage operating at a pressure ratio of 1.7:1. The resulting gas is therefore at a pressure of about 150 psi, with a peak temperature of less than 35° C.

Of course, once generated, the ozone must be applied to the material to be treated. For blood work, one option is simply to add the pressurized ozone into a sterile blood bag system. The difficulty here is that conventional bags are not designed to handle such pressures. Although new bags could be built, they would be much more expensive than conventional units. Even then, should a bag rupture during treatment, it would then spray potentially contaminated plasma throughout the laboratory. Finally, from a practical standpoint, generating sufficient ozone to pressurize the bag would be expensive and time-consuming, and would waste much of the valuable ozone that could otherwise be used for attacking the contaminants.

For these reasons, a new exposure system is necessary. This system consists of a pressure cell, which is driven by a standard air compressor. By pressurizing this cell with air to the same pressure as the ozone, the pressure on both sides of the treatment bags is equalized. Cheap bags can thus be used, there is no risk of rupture, and the ozone requirements are greatly reduced. With conventional 110 VAC compression equipment, pressures up to about 10 atmospheres (about 150 psig) can be achieved easily, and if desired even higher pressures can be generated by 220 VAC equipment.

During the time that ozone is not required, such as during bag changes or ultrasonic vacuum degassing, it is desirable to maintain the ozone source at pressure so that processing can be continued immediately when necessary. With conventional gasses, the pressure is typically maintained in a simple storage tank. Ozone, however, degrades so rapidly that this is not an option. Furthermore, electrolytic units, such as the Lynntech device, must be operated continuously for best output.

For these reasons, the use of a bypass circuit is preferred. The first part of this circuit is a solenoid valve placed at the outlet of the ozone generator. When activated, this valve diverts the ozone around the treatment vessel and through a check valve that maintains the desired pressure. The output of this valve is then joined through a y-connection with the treatment chamber output. The resulting combined flows then proceed to a destruct unit that converts the ozone back to oxygen before venting. Although not necessary for operation of the decontamination unit per se, such destruct units ensure that the decontamination process does not contribute to low level ozone pollution.

Finally, for electrolytic units, it is necessary to balance the pressure loading on the generator cell. Specifically, electrolytic units produce ozone and oxygen on one side of this cell, and hydrogen on the opposite side. In practice, the hydrogen back pressure can be maintained simply by a check valve. Downstream processing can then be done at approximately atmospheric pressure, using a simple drain trap for water and an optional hydrogen destruct unit. This equipment can thus be conveniently arranged parallel to the ozone bypass circuit.

While the above system has been described for individual or batch units, the previously described feeding and emptying procedures for the vacuum operation embodiments can be readily modified to accommodate continuous flows. The only significant change is that the described pressure differences must be reversed.

After pressure, the next concerns are temperature and humidity, which are inter-dependent. The potential temperature problem here is that the gas may be so hot or cold that it damages the proteins. In addition, the humidity can be so low that the proteins could be excessively dried, or so high that the proteins could be diluted with excess moisture.

For precise control of the ozone temperature, a Peltier system is desirable (Model TLC-1400, TECA, Inc., Chicago, Ill.). Alternatively, conventional refrigeration and heating devices can also be used if proper controls are provided (Model RTE, Neslab, Portsmouth, N.H.). Both systems provide a source of either heated or cooled water. Connecting a heat exchanger to these devices therefore provides a simple means of regulating the ozone temperature.

A particularly simple arrangement is to use a Teflon® or similar plastic tube to connect the ozone source to the treatment unit. Teflon® is desirable in these applications because it is quite resistant to attack by ozone. Although Teflon® is somewhat permeable to gasses, these losses are not excessive. If desired, however, lower permeability forms of Teflon®, notably Teflon® PFA, can also be used. Another alternative is to use a Teflon® laminate with a low permeability plastic.

Placing loops of the selected tubing in the controlled temperature bath thus provides the desired ozone heating or cooling. Alternatively, metal heat exchangers could also be used, but in this case it is necessary to protect the metal surface from attack by the highly reactive ozone. An effective protective layer is Teflono®. For even faster heat transfer, stainless steel tubing can be used. In particular, tubing that has been treated with nitric acid rapidly forms an inert layer that resists further corrosion, without greatly reducing the heat flow (Stainless steel tubing: Nitric acid treated, Upchurch Scientific, Oak Harbor, Wash.).

Immediately downstream of the heat exchanger, a water trap is used to collect and remove any condensates in high humidity systems. The problem here is that the condensed water must be removed without losing the system pressure. As such, the first part of the water trap is a small pressure vessel. This vessel is connected to a scale, float, optical or electrical sensor to determine the level of the water in the trap. When the vessel becomes filled, a solenoid valve is then actuated to release the pressurized liquid into a drain. For complete draining a "flip-flop" circuit is used to keep the valve actuated during the entire draining process, with the state of the circuit reversed by a switch placed at the closing location. This valve should have Teflon® flow surfaces to resist attack by the ozone. Also, for minimal energy consumption, this valve should be "normally closed." Downstream of this valve, a flow restriction must be placed in the outlet tube to prevent excessive spraying at elevated pressures. An alternative approach is to use a peristaltic pump, if it is necessary to transport the liquid to a higher level than the ozone pressure can support. In either case, the drain must be closed before the trap is completely empty; otherwise, there will be some leakage of the ozone gas.

In the case of low humidity generators, a device to increase the humidity to the required level replaces the water trap. In this case, a source of high purity water is required, as well as some means to vaporize this water at low temperatures. Sonic humidifiers are well suited for this application. Finally, it is also possible to use a heated vaporization system if the entering ozone is sufficiently cool, or can be cooled after water addition.

With these combined features, the ozone is thus delivered to the treatment chamber at the proper concentration, pressure, temperature and humidity. However, while these conditions are quite effective in decontamination, it is possible to accelerate the process even more by incorporating the previously described degassing technology.

The underlying principle here is, again, a matter of basic ideal gas behavior. Specifically, each gas has its own characteristic solubility in a given liquid; furthermore, Fick's first law describes the diffusion of this gas in the liquid, while Henry's law describes the concentration of this gas in the liquid, relative to the partial pressure of this gas above the liquid.

Under normal conditions, water or a dilute aqueous solution thus has an oxygen concentration of about 35%, and a nitrogen concentration of about 63%; these values differ from the respective 21% and 78% values in air because oxygen is more soluble than nitrogen. When subsequently exposed to a saturated mixture of 15% ozone and 85% oxygen, the nitrogen concentration then decreases as the liquid takes up ozone and oxygen. Ozone, however, is about 13 times more soluble than oxygen, so the uptake of oxygen is more rapid. On the other hand, ozone reacts with the liquid in which it is dissolved. Thus, some of the oxygen in the ozone combines with some of the other components in the solution, and some of the remaining oxygen reverts to the normal, diatomic form. In either case, the incoming ozone eventually completely reacts to a lower energy form, leaving a decontaminated liquid that is enriched with oxygen, and depleted from other gasses.

Although the above sequence thus describes the events that occur in conventional ozone decontamination units, in the present invention an additional factor must be considered. Specifically, conventional liquids already contain some dissolved gasses that must be displaced when a new gas is introduced. Conversely, a degassed liquid has no such gasses present, and thus the intermolecular spaces that would otherwise be occupied by gas molecules are instead vacant. As a result, when the pressurized ozone is introduced, it essentially acts upon a liquid under partial vacuum, and the resulting uptake is therefore much more rapid than would occur under simple diffusion through a normal liquid. Furthermore, this rapid absorption allows the ozone to penetrate more deeply within the liquid before reacting or being displaced, thereby yielding a more uniform distribution of ozone within the liquid being treated. Compared to conventional liquids, the immediate benefits of degassing prior to ozone exposure thus include higher processing speeds and more thorough decontamination.

To obtain even greater improvements, the above sequence is cycled in the present invention. The underlying phenomena have been previously proposed for increasing the concentration of oxygen in water (see, Samuel Glasstone, *Textbook of Physical Chemistry*, Van Nostrand, New York, p.699, 1946). The basic concept here is to use the higher water solubility of oxygen versus nitrogen to differentiate these gasses. Using partial heating to drive out the nitrogen, several such cycles would eventually yield residual oxygen concentrations approaching 90%. In practice, of course, oxygen can be more rapidly and cheaply produced by cryogenic pumping.

Thus, while not practical for oxygen generation, this cycling approach is however quite useful in the present invention. The main modification is to use the above vacuum and ultrasound degassing system, thus sparing the cost and protein damage of heating. Since the relative solubility of ozone to oxygen is about 13:1, which is much greater than the above noted values for oxygen versus nitrogen, the concentration proceeds extremely rapidly. In particular, the concentration quickly reaches levels that are well beyond those that are obtained under normal circumstances.

The immediate concern is just how high these concentrations can reach. Unfortunately, there is no definitive answer here for two main reasons. First, because these concentrations are well beyond those that can be maintained in a steady state, they do not last long enough for accurate measurement.

The second problem in trying to determine the concentration limit is that ozone reacts with the liquid in which it is dissolved. For example, ozone has a half-life in oncedistilled water of about 20 minutes, but a half-life of 80 minutes or more in water that has had multiple distillations. Furthermore, small amounts of acids or neutral salts increase the solubility of ozone and extend the half-life of the solution. Conversely, alkalis decrease the solubility of ozone (see, Atherton Seidell, *Solubilities of Inorganic and Organic Compounds*, Van Nostrand, New York, p. 473, 1919).

The immediate result is that even small amounts of contaminants greatly affect the behavior of dissolved ozone. This is of particular concern in the present invention because the salt-buffered acid-base systems that are characteristic of biological systems can thus strongly affect the speed and degree of decontamination. Furthermore, in the case of blood, the effects of anticoagulants must also be considered because there are many different types of these agents in common use today, including various citrates, EDTA, heparin, etc., and each of these agents has its own unique chemistry.

The net result is that upper concentration limits cannot be strictly established because of the transient nature of such concentrations, combined with highly variable reaction rates that are specific to individual cases. Nevertheless, some practical guidelines can be established. For example, for human gaseous exposure, 0.1 ppm can be tolerated over an eight hour period.

For decontamination work, gaseous concentrations can be on the order of hundreds or even thousands of parts per million. Conventional liquid concentrations are on the order of 0.3 to 10 mg/L. This range is also the base for the present invention, but the peak transient concentrations are on the order of 100 to 200 mg/L.

On the other hand, ozone is quite toxic at these higher concentrations, and can rapidly damage delicate proteins. For this reason, the present invention utilizes the previously described degassing equipment to remove the excess ozone as soon as the decontamination is completed.

Finally, the above arguments hold for ozone treatment systems in general. For example, increased pressure will always force more ozone into solution. In actual practice, however, the behavior of any ozone decontamination system depends strongly on how the ozone is introduced into the liquid.

In the ozone industry, the process of introducing ozone into a liquid is called "contacting," and the devices used for this process are called "contactors." To be effective, the contactor must be designed to match the properties of the fluid being treated. For example, in the preparation of drinking water or in the treatment of toxic wastes, high levels of turbulence and shear can be tolerated without concern for damaging the liquid being processed; furthermore, the contactors can be fabricated from any reasonably strong construction material. As noted above, however, protein systems, notably those involving blood products, must be handled much more carefully, and plastics that will not induce the clotting sequence must be used instead of materials such as glass.

For example, these concerns are particularly important in the treatment of blood platelets, which are quite easily damaged by mechanical or thermal stress. In terms of contactor design, a unique factor is that platelets are processed in small volumes, on the order of 50 milliliters or so, depending on the equipment and the donor.

Figure 11:
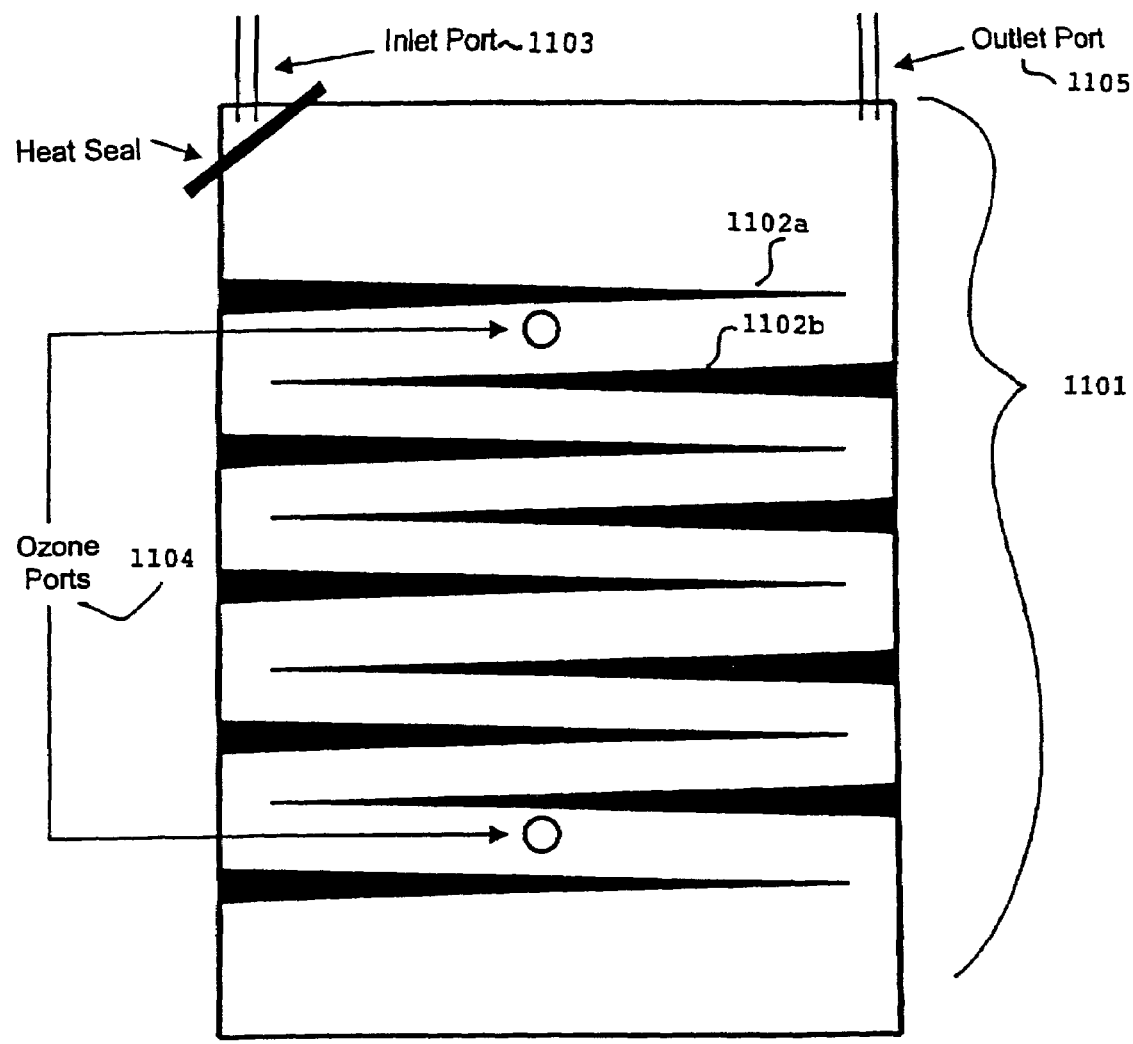
FIG. 11 is a schematic representation of another ozone contactor which is useful for platelets.

Because of this relatively small volume, the entire donation can be spread over the treatment chamber at one time. A particularly preferred chamber for the contacting of platelets is shown in FIG. 11; the treatment chamber consists of a rectangular or similarly shaped block 1101 with staggered, opposed shelves in the shape of sharp wedges 1102. With the chamber in the horizontal position, the liquid enters a trough or inlet port 1103 along one side. After filling this trough, the chamber is then rotated upwards to about 80 degrees, at which point the fluid flows over the first shelf 1102*a* towards the opposing wall. Because the shelf does not actually touch the opposing wall, however, the fluid drops down to the next shelf 1102*b* and the flow then reverses. Meanwhile, ozone is introduced through ports 1104. Note that this arrangement is unlike the above cited patents because the flow reversal thoroughly mixes the material at each step, with the top layer becoming largely the bottom layer and vice versa.

The rotation continues until all of the fluid is emptied from the inlet trough, which occurs at about 90 degrees. The entire arrangement is then rotated back into its original position, and then on to −90 degrees to repeat the process from the opposite direction. During these movements, ozone is continuously fed into one side of the treatment chamber, and spent gas removed from the opposite side. Because the motion of the chamber is thus essentially two reversing half-turns, the gas connections can be conventional flexible hoses. This arrangement thereby saves the costs and installation problems of the sealed bearings, etc., that are required for the continuous rotation units described earlier.

Additional enhancements of this device include an ultrasonic driver to improve the rate of fluid flow and to aid in the mixing of the ozone; a pressurized treatment cell; and an ultrasonic degassing option with vacuum assist. The benefits of each of these components have been discussed earlier, but even with these enhancements, this device cannot handle larger volumes of fluid effectively. It is therefore necessary to modify this device to treat plasma and other larger volume, heat-sensitive solutions.

Figure 5:
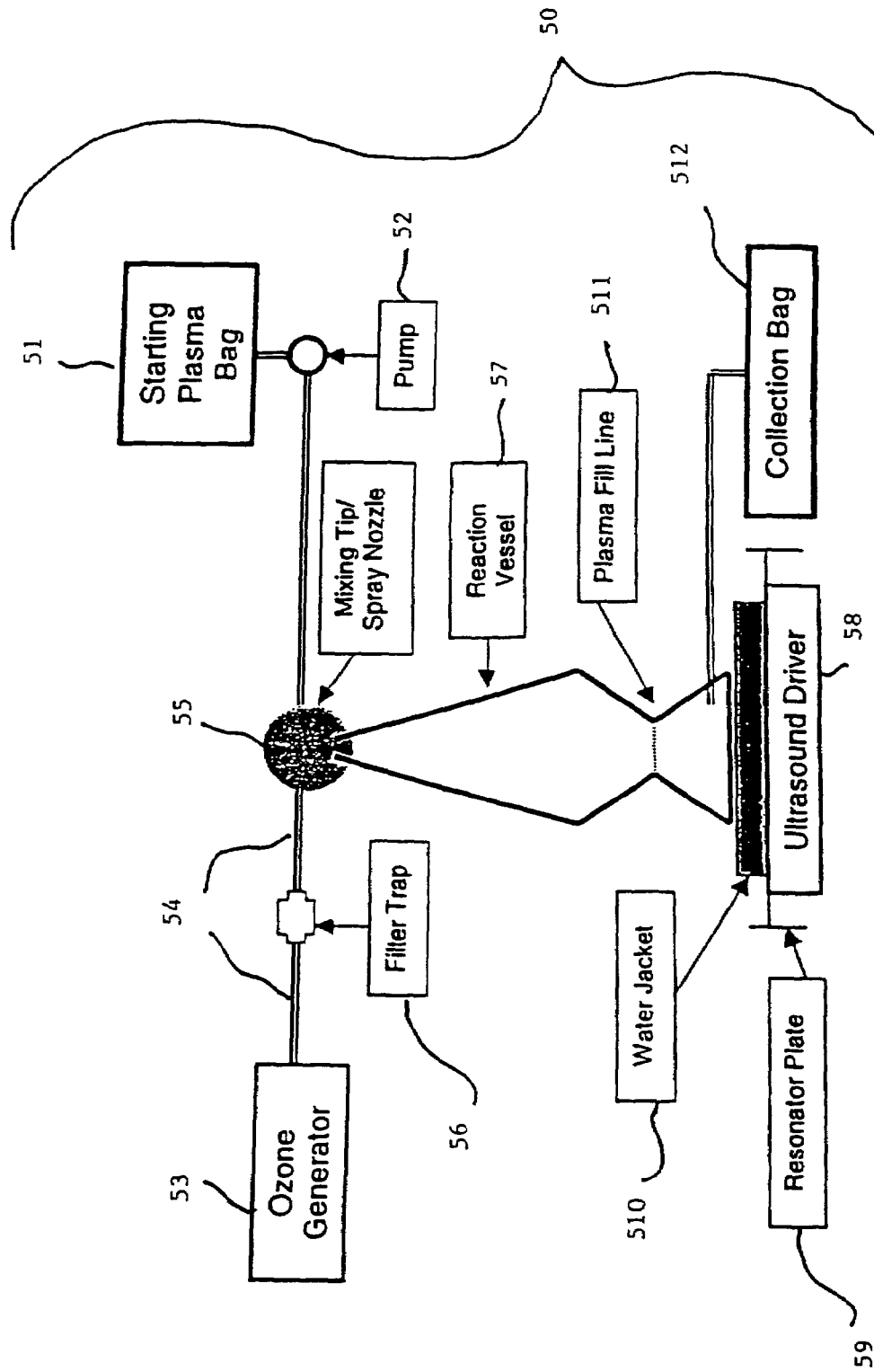
FIG. 5 is a schematic representation of a combined ozone and ultrasound treatment apparatus according to the present invention.

One such approach is shown in FIG. 5. This device employs an ultrasonic spray nozzle at the top of an enclosed chamber. Unlike the previously described spray system (U.S. Pat. No. 5,882,591), this device has no electrostatic fields, but it does incorporate elevated pressures, direct ultrasonic processing of the sprayed fluid, and other enhancements described more fully below.

Unfortunately, while the ultrasound greatly reduces the shear on the liquid being sprayed, this process can still damage delicate proteins and cell suspensions. Also as noted earlier for other spray applications (U.S. Pat. No. 5,882, 591), a fine spray of contaminated biological materials should be avoided whenever possible. It is therefore necessary to develop yet another contactor for general blood work, and similar applications.

The key feature of this contactor is that the fluid to be treated flows through an enclosed channel. Ozone is then fed into the liquid through a series of small holes in the channel wall.

While this arrangement thus has some similarities to conventional gas/liquid bubbling devices, there are however significant differences. Specifically, the ability to rotate the chamber aids in the bulk mixing of the fluid, thereby providing more uniform treatment. This mixing is further aided by the ultrasound, but ultrasound also has other important effects in the present application.

Historically, the use of ultrasound to aid ozone contacting has been discussed by W. S. Masschelein (see, "*Handbook of Ozone Technology and Applications, Volume One*," R. G. Rice and A. Netzer, eds., Ann Arbor Science, The Butterworth Group, Kent, England, p. 180, 1982; See also, C. Nebel, P. C. Unangst and R. D. Gottschling, "An Evaluation of Various Mixing Devices for Dispensing Ozone in Water," *Water Sew. Works Ref. No. R*-6 (1973)). In particular, it is noted that reversing the gas and liquid channels of a conventional ultrasonic nozzle produces a finely divided bubble distribution. Finally, as noted earlier, U.S. Pat. 4,597,876 describes ultrasonic resonance effects on ozone bubbles. In particular, it is known that ultrasound will drive small bubbles into the liquid, but larger bubbles will grow to the point that they can be removed.

In the present invention, ultrasound is coupled with a unique contactor to force as much ozone into the solution as possible. Specifically, the contactor in the present invention is driven directly by ultrasound. Furthermore, this ultrasound is delivered by a high amplitude horn, so that the oscillations are large in displacement. In addition, this displacement is larger than the diameter of the holes through which the ozone flows. The net result is that the ultrasound shears off extremely small bubbles into the surrounding liquid. Being much smaller than resonance, or even stable, size these small bubbles are then forced into the liquid rapidly under the action of ultrasound.

Under the above degassing, pressurization, and contacting procedures, it is thus possible to drive quite large amounts of ozone into the treated liquid. For effective decontamination, however, it is necessary to measure the amount of dissolved ozone. Because ozone is highly reactive, this measurement must be accurate to avoid over treatment. For feedback purposes, this measurement must be made in real time. Finally, for protein solutions, this measurement must be made under sterile conditions.

Optical measurement techniques satisfy all of these conditions. In particular, the absorption of UV light is a particularly useful measurement technique (Ocean Optics Model 2000, Dunedin, Fla.). To achieve this measurement in practice, a UV transparent window is provided in the ozone treatment path. Like the UV exposure bags, Teflon® is ideal, but expensive; lower quality plastics may be used if a very bright UV source is available.

The major limitation in this technology is the presence of gas bubbles. Although present as a result of decontamination, these bubbles are a significant problem in the measuring process because they are optically quite different from the concentrated ozone solution. To minimize this problem, the measurement cell may be made with a wide top and a narrow bottom. Under this geometry, the gas bubbles rise to the surface, leaving only liquid in the path of the measuring UV light beam.

The details for achieving the above processes in practice are described more fully in the following embodiments.

XII. In a Twelfth Main Embodiment, the Present Invention Provides a Method for Decontaminating Plasma by:

(a') a step for the treatment of a fluid with ultrasonic energy to obtain a de-oxygenated fluid; and (b') a step for the treatment of said de-oxygenated fluid with ozone.

In this twelfth main embodiment, the step (a') "for the treatment of a fluid with ultrasonic energy to obtain a de-oxygenated fluid" may be carried out in the same ways that step "(a) treating a fluid with ultrasonic energy to obtain a de-oxygenated fluid" is carried out in the context of the eleventh main embodiment. In addition, the step (b') "for the treatment of said de-oxygenated fluid with ozone" may be carried out in the same ways that step "(b) contacting said de-oxygenated fluid with ozone" is carried out in the context of the eleventh main embodiment.

XIII. In a Thirteenth Main Embodiment, the Present Invention Provides a Method for Decontaminating a Fluid by:

(a) mixing a fluid with ozone, to obtain an ozone-containing, fluid; and (b) treating said ozone-containing fluid with ultrasonic energy.

In this thirteenth embodiment, the treatment of the fluid with the ultrasonic energy may be carried out in the same ways and by using the same apparatus as described above in the context of the first, second, third, fourth, fifth, sixth, seventh, eighth, ninth, tenth, eleventh, and twelfth main embodiments.

In this thirteenth main embodiment, ultrasonic energy is used to enhance the decontamination effect of ozone. As noted above, ozone treatment is a standard decontamination technique. While quite effective, however, ozonation unfortunately suffers from relatively long treatment times. As also noted above, it is useful to combine techniques to yield more complete decontamination than can be achieved by using any one technique acting alone. This thirteenth main embodiment of the present invention therefore uses ultrasonic energy to accelerate the ozone decontamination process, and to improve the overall effectiveness of the combined system.

It is already known that ultrasound is effective in enhancing the speed of bacterial decontamination (see, W. S. Masschelein, "Handbook of Ozone Technology and Applications, Volume One," R. G. Rice and A. Netzer, eds., Ann Arbor Science, The Butterworth Group, Kent, England, p. 180, 1982). In addition, it is also known that there is a synergistic effect between ozone and ultrasound (see, Burleson G R; Murray T M; Pollard M "Inactivation of viruses and bacteria by ozone, with and without sonication," Appl Microbiol Mar. 29, 1975 (3):340–4).

The apparent mechanism behind these effects is that ultrasound is known to improve chemical reactivities, particularly those involving free radicals (V. Misik and P. Riesz, "Detection of primary free radical species in aqueous sonochemistry by EPR spectroscopy." in *Sonochemistry and Sonoluminescence*, edited by L. A. Crum, T. J. Mason, J. L. Reisse and K. S. Suslick, NATO ASI Series C, Kluwer Academic Publishers, Dordrecht, pp. 225–236, 1999). In addition, it is also possible that some of the observed enhancements could also be due to improved mixing.

In the present invention, the unique aspects of applying ultrasound to a liquid containing dissolved ozone is that the above conditions and techniques are applied to protect the proteins in solution during the decontamination process. In the following, this embodiment will be described in the context of plasma, and amounts to first mixing the ozone with the plasma. Next, the ozone-containing plasma is then treated with ultrasonic energy. In this embodiment, the plasma is treated with ultrasonic energy as described above.

Of course, it is to be understood that the term "treating said ozone-containing fluid with ultrasonic energy" does not require that the application of ultrasonic energy to the ozone-containing fluid commence after the introduction of ozone into the fluid has ceased. To the contrary, this term means that the application of ultrasonic energy to the ozone-containing fluid may commence: (1) prior to the commencement of the introduction of ozone into the fluid; (2) at the time the introduction of ozone into the fluid is commenced; (3) after the introduction of ozone into the fluid has commenced; or (4) after the introduction of ozone into the fluid has ceased. In fact, in an especially preferred sub-embodiment, the ultrasonic energy is applied to the fluid during the entire time that the ozone is introduced into the fluid.

XIV. In a Fourteenth Main Embodiment, the Present Invention Provides a Method for Decontaminating a Fluid by:
 (a') a step for mixing a fluid with ozone, to obtain an ozone-containing fluid; and
 (b') a step for the treatment of said ozone-containing fluid with ultrasonic energy.

In this fourteenth main embodiment, the step (a') "for mixing a fluid with ozone, to obtain an ozone-containing fluid" may be carried out in the same ways that step "(a) mixing a fluid with ozone, to obtain an ozone-containing fluid" is carried out in the context of the thirteenth main embodiment. In addition, the step (b') "for the treatment of said ozone-containing fluid with ultrasonic energy" may be carried out in the same ways that step "(b) treating said ozone-containing fluid with ultrasonic energy" is carried out in the context of the thirteenth main embodiment.

XV. In a Fifteenth Main Embodiment, the Present Invention Provides a Method for Decontaminating a Fluid by:
 (a) treating a fluid with ultrasonic energy to obtain a de-oxygenated fluid;
 (b) contacting said de-oxygenated fluid with ozone, to obtain an ozone-containing fluid; and
 (c) treating said ozone-containing fluid with ultrasonic energy.

The fifteenth main embodiment is essentially a combination of the eleventh and thirteenth main embodiments. Thus, in this fifteenth main embodiment, the fluid is first degassed using ultrasonic energy as discussed above. The degassed fluid is then contacted with ozone, and the ozone-containing fluid is treated with ultrasonic energy to enhance the reactivity of the ozone, as described in the ninth main embodiment.

XVI. In a Sixteenth Main Embodiment, the Present Invention Provides a Method for Decontaminating Fluid by:
 (a') a step for the treatment of a fluid with ultrasonic energy to obtain a de-oxygenated fluid;
 (b') a step for the treatment of said de-oxygenated fluid, to obtain an ozone-containing fluid; and
 (c') a step for the treatment of said ozone-containing fluid with ultrasonic energy.

In this sixteenth main embodiment, the step (a') "for the treatment of a fluid with ultrasonic energy to obtain a de-oxygenated fluid" may be carried out in the same ways that step "(a) treating a fluid with ultrasonic energy to obtain a de-oxygenated fluid" is carried out in the context of the fifteenth main embodiment. In addition, the step (b') "for the treatment of said de-oxygenated fluid, to obtain an ozone-containing fluid" may be carried out in the same ways that step "(b) contacting said de-oxygenated fluid with ozone, to obtain an ozone-containing fluid" is carried out in the context of the fifteenth main embodiment. Lastly, the step (c') "for the treatment of said ozone-containing fluid with ultrasonic energy" may be carried out in the same ways that step "(c) treating said ozone-containing fluid with ultrasonic energy" is carried out in the context of the fifteenth main embodiment.

XVII. In a Seventeenth Main Embodiment, the Present Invention Provides a Method for Decontaminating a Fluid by:
 (a) treating a fluid with ultrasonic energy to obtain a de-oxygenated fluid;
 (b) irradiating said de-oxygenated fluid, to obtain an irradiated fluid; and
 (c) contacting said irradiated fluid with ozone, to obtain an ozone-containing fluid.

This seventeenth main embodiment represents a combination of the irradiation and ozone-treatment embodiments described above. Thus, this main embodiment represents a combination of the fifth and seventh main embodiment, and the steps (a), (b), and (c) may be carried out in the same ways and with the same apparatus described above. As noted earlier, combined decontamination processes are quite attractive because they produce very high log reduction rates.

In this embodiment, the ozone-treatment decontamination may either precede or follow the irradiation decontamination. However, even though ultrasonic degassing is very effective, it is generally not desired to add extra dissolved oxygen species in the ozone process before subsequently removing them in the irradiation process. Furthermore, performing the ozone-treatment decontamination after the irradiation decontamination would allow any residual ozone additional time to react with the pathogens, which would thus improve the overall kill effectiveness. For these two reasons, it is preferred that the irradiation decontamination precede the ozone-treatment decontamination. Accordingly, in a preferred embodiment utilizing plasma as the fluid, this method comprises:

(a") treating plasma with ultrasonic energy to obtain de-oxygenated plasma;
(b") irradiating said de-oxygenated plasma, to obtain irradiated plasma; and
(c") mixing said plasma with ozone, to obtain ozone-containing plasma.

XVIII. In an Eighteenth Main Embodiment, the Present Invention Provides a Method for Decontaminating a Fluid by:

(a') a step for the treatment of a fluid with ultrasonic energy to obtain a de-oxygenated fluid;
(b') a step for the irradiation of said de-oxygenated fluid, to obtain an irradiated fluid; and
(c') a step for the treatment of said irradiated fluid, to obtain an ozone-containing fluid.

In this eighteenth main embodiment, the step (a') "for the treatment of a fluid with ultrasonic energy to obtain a de-oxygenated fluid" may be carried out in the same ways that step "(a) treating a fluid with ultrasonic energy to obtain a de-oxygenated fluid" is carried out in the context of the seventeenth main embodiment. In addition, the step (b') "for the irradiation of said de-oxygenated fluid, to obtain an irradiated fluid" may be carried out in the same ways that step "(b) irradiating said de-oxygenated fluid, to obtain an irradiated fluid" is carried out in the context of the seventeenth main embodiment. Lastly, the step (c') "for the treatment of said irradiated fluid, to obtain an ozone-containing fluid" may be carried out in the same ways that step "(c) contacting said irradiated fluid with ozone, to obtain an ozone-containing fluid" is carried out in the context of the seventeenth main embodiment.

XIX. In a Nineteenth Main Embodiment, the Present Invention Provides a Method for Decontaminating a Fluid by:

(a) treating a fluid with ultrasonic energy to obtain a de-oxygenated fluid;
(b) irradiating said de-oxygenated fluid, to obtain an irradiated fluid;
(c) contacting said irradiated fluid with ozone, to obtain an ozone-containing fluid; and
(d) treating said ozone-containing fluid with ultrasonic energy.

This embodiment represents another combination of the irradiation and ozone-treatment embodiments described above. Thus, this nineteenth main embodiment represents a combination of the fifth and thirteenth main embodiments, and the steps (a), (b), (c), and (d) may be carried out in the same ways and with the same apparatus described above.

As noted earlier, combined decontamination processes are quite attractive because they produce very high log kill rates. In this embodiment, the ozone-treatment decontamination may either precede or follow the irradiation decontamination. However, even though ultrasonic degassing is very effective, it is generally not desired to add extra dissolved oxygen species in the ozone process before subsequently removing them in the irradiation process. Furthermore, performing the ozone-treatment decontamination after the irradiation decontamination would allow any residual ozone additional time to react with the pathogens, which would thus improve the overall kill effectiveness. For these two reasons, it is preferred that the irradiation decontamination precede the ozone-treatment decontamination. Accordingly, in a preferred embodiment utilizing plasma as the fluid, this method comprises:

(a") treating plasma with ultrasonic energy to obtain de-oxygenated plasma;
(b") irradiating said de-oxygenated plasma, to obtain irradiated plasma;
(c") mixing said plasma with ozone, to obtain ozone-containing plasma; and
(d") treating the ozone-containing plasma with ultrasonic energy.

XX. In a Twentieth Main Embodiment, the Present Invention Provides a Method for Decontaminating a Fluid by:

(a') a step for the treatment of a fluid with ultrasonic energy to obtain a de-oxygenated fluid;
(b') a step for the irradiation of said de-oxygenated fluid, to obtain an irradiated fluid;
(c') a step for the treatment of said irradiated fluid, to obtain an ozone-containing fluid; and
(d') a step for the treatment of said ozone-containing fluid with ultrasonic energy.

In this twentieth main embodiment, the step (a') "for the treatment of a fluid with ultrasonic energy to obtain a de-oxygenated fluid" may be carried out in the same ways that step "(a) treating fluid with ultrasonic energy to obtain a de-oxygenated fluid" is carried out in the context of the nineteenth main embodiment. In addition, the step (b') "for the irradiation of said de-oxygenated fluid, to obtain an irradiated fluid" may be carried out in the same ways that step "(b) irradiating said de-oxygenated fluid, to obtain an irradiated fluid" is carried out in the context of the nineteenth main embodiment. The step (c') "for the treatment of said irradiated fluid, to obtain an ozone-containing fluid" may be carried out in the same ways that step "(c) contacting said irradiated fluid with ozone, to obtain an ozone-containing fluid" is carried out in the context of the nineteenth main embodiment. Lastly, step (d') "for the treatment of said ozone-containing fluid with ultrasonic energy" may be carried out in the same ways that step "(d) treating said ozone-containing fluid with ultrasonic energy" is carried out in the context of the nineteenth main embodiment.

XXI. In a Twenty-first Main Embodiment, the Present Invention Provides an Apparatus for Decontaminating a Fluid, Comprising:

(1) a chamber for containing a fluid;
(2) a vacuum source coupled to the chamber; and
(3) a source of ultrasonic energy coupled to the chamber, wherein said chamber comprises (i) a flat panel, (ii) an inlet, and (iii) an outlet; and wherein said flat panel of said chamber and said inlet are dimensioned such that a fluid flowing through said inlet and across said flat panel to said outlet will form a thin film and travel in plug flow at least during some portion of its flow across said flat panel.

Any surface of the chamber which comes into contact with the plasma should be constructed of materials that will have no have no deleterious effect on the fluid, especially when the fluid is plasma. Suitable materials for those portions of the chamber which come into contact with the plasma are as specified by FDA for contact with blood. Although not an absolute requirement, it is preferred that at least a portion of the chamber be constructed of a transparent material to permit visual inspection of the decontamination process.

In any case, PVC is currently widely used, and there are various polyolefin bags under development. The main concern with these new materials is that the plasticizer may leach out over time. For the present methods, however, the contact time is quite short. On the other hand, the sonification may accelerate the leaching process. However, because tests to date show no measurable degradation, there appears to be no unique restrictions for the present method and apparatus.

The chamber is configured to contain a flat panel or plane at the bottom. Although there is no particular limitation on the size of the flat panel, there are two general types of sizes. First, for individual units from an apheresis donation of about 600 ml, the flat panel would be approximately 25 by 25 cm. On the other hand, continuous, large scale units for pool processing would have planar sections on the order of several meters.

The chamber also contains an inlet and an outlet. The inlet is preferably located near the bottom of the chamber and extends along the width of one end of the flat panel. The inlet is preferably a divergent spreader to assist in forming the plasma into a thin film as it flows across the flat panel at the bottom of the chamber. The height of the inlet is preferably dimensioned such that plasma forms a thin film. The exact thickness of the film is not by itself critical. All that is required is that the gas bubbles reach the surface relatively quickly. In the case of very durable proteins, this is not even a consideration. For less durable proteins and cells, a thickness of 2 to 20 mm, preferably 2 to 10 mm, and more preferably then 2 to 4 mm may be used. This is by no means precise, and it is possible the thickness may be varied by simply changing the vacuum settings, power, etc. and then tuning to a different range.

The creation of plug flow is well known (John A. Roberson, Clayton T. Crowe, Engineering Fluid Mechanics, Third Edition, Houghton Mifflin Company, NY, 1985).

The dimensions of inlet and the flat panel are preferably adjusted such that the plasma flows across the flat panel in plug flow. Thus, the ratio of the length of the flat panel to the width of the inlet is less than twenty, preferably less than fifteen, more preferably less than about ten.

In a preferred embodiment, the inlet is connected to a device for controlling the flow rate of plasma across the flat panel. The flow of the fluid may be controlled as follows. In terms of blood, the treatment range includes plasma, as well as platelets and erythrocytes (red blood cells).

First, all blood applications should include a means to remove the white blood cells (leukocytes). While leukocytes are obviously useful in the donor, transfusion of these cells can result in a number of adverse immune reactions. Even worse, these cells also present an opportunity to transmit diseases, notably nvCJD (new variant Creutzfeldt-Jacob Disease). For this reason, these cells should either be destroyed, or preferably, removed. A simple approach is to use one of the many FDA approved filters, one example being those of Pall Corporation (New York).

Next, plasma should be heated to about 53° C. for one hour. This procedure alone kills many viruses. Another advantage of this heating is that the dissolved oxygen drops rapidly at such elevated temperatures. Another advantage is that cavitation is much easier at elevated temperatures. The actual heating method is not critical, as long as it is reasonably fast. There are several blood, plasma, and IV solution warmers on the market capable of providing the necessary heating.

Of course, some components of plasma (notably Factor V) are labile, and will not tolerate such treatment; likewise, platelets and rbc's cannot be heated this way. For these cases, the bulk of the material will be maintained at the lower temperature, and heat will be applied only as the liquid enters the degassing unit.

The fluid is then cooled immediately after degassing, thereby minimizing the total heat exposure. Of course, there is also the option of no heat at all.

The net effect is at this point, the fluid to be treated is in a bag, which may or may not be heated. The next task is to get this fluid into the degassing unit. As described earlier, one option is a peristaltic pump. While quite effective for robust materials such as plasma, rbc's and platelets would however suffer severe degradation because only finely spaced rollers on a very thin tube can achieve the required low, steady flow rate. This arrangement, unfortunately, would cause excessive pumping damage to the entrained cells. Furthermore, the vacuum on the discharge side would exacerbate the pumping damage.

For these reasons, cellular systems will use a body force system for fluid flow. Specifically, the suction from the vacuum system will provide the overall driving force. To prevent the fluid from being drawn in too rapidly, the flow will be retarded by several techniques. One option is to use a very narrow tube, thus causing frictional losses. Another option is a flow restriction, such as a pin hole in an occluding membrane. A third option is to place the inlet bag below the degassing unit, so that the suction must overcome gravity. A fourth option is to include the bag inside a partial vacuum system, so that the pressure difference between the degassing and feed side can be controlled. A fifth option is a variable screw arrangement, which can be tightened or loosened as necessary to control the flow through the connecting tube. All of these approaches, as well as other standard metering techniques, can be applied.

The only remaining concern is how to control the process in practice. The problem here is that the vacuum must be established, the ultrasound made ready, the UV lamps warmed, etc., before the liquid is drawn into the system. The necessary control can be achieved by placing a shut off valve on the feed tube. For complete automation, this valve may be controlled electronically.

In another preferred embodiment, the inlet is configured to be connected to the outlet of an individual apheresis donation unit. In this embodiment, the device for controlling the flow rate of the plasma may be contained within the individual apheresis donation unit itself or located between the inlet and the individual apheresis donation unit. Alternatively, the inlet may be configured to be easily connected and disconnected to any plasma container, such as a plasma bag.

The outlet is also preferably located near the bottom of the chamber at the end of the flat panel opposite that of the inlet. In any event, the outlet is positioned such that the plasma flowing across the flat panel will exit the chamber through the outlet after having traversed the flat panel.

In one preferred embodiment, the outlet is configured so as to be easily connected and disconnected to a container for receiving the decontaminated plasma. Such a container may range in size from many hundreds or even thousands of liters for apparatus used for the continuous decontamination of large pools of plasma units to as small as a few hundreds or even tens of ml for apparatus used to decontaminate individual units.

In another preferred embodiment, the chamber includes a second outlet which is in communication with a vacuum source, such as a vacuum pump. The second outlet is preferably located near the top of the chamber or at least above the top of the plasma layer, such that plasma is not sucked into the second outlet when a vacuum is applied to the chamber through the second outlet. Preferably, the vacuum source can provide a vacuum to the space above the thin film of plasma in the chamber of 2 to 100 mbar, preferably about 10 to 80 mbar, more preferably 20 to 60 mbar.

In another preferred embodiment, the apparatus comprises a liquid trap with a sterile filter located between the second inlet and the vacuum source.

The source of ultrasonic energy may be any which is capable of generating ultrasonic energy having the desired frequency and intensity. Such ultrasound generators include those described above.

The source of the ultrasonic energy is coupled to the chamber such that the desired intensity and frequency of ultrasonic energy may be applied to the thin film of plasma flowing across the flat panel. In a preferred embodiment, the apparatus comprises an ultrasound driver located beneath the flat panel. In a particularly preferred embodiment, the apparatus comprises a water jacket located between the ultrasound driver and the flat panel. In another particularly preferred embodiment, the apparatus comprises a resonator plate located between the ultrasound driver and the water jacket. The water jacket is preferably connected to a cooling and circulation system such that cooled water circulates through the water jacket when the ultrasonic energy is being applied to the plasma.

The present apparatus may further comprise additional sensors and data loggers to ensure regulatory compliance. Such additional sensors may include a hydrophone to ensure adequate cavitation or degassing, thermocouples to ensure adequate temperature maintenance, digital scales on the input and output bags to ensure proper flow rates as functions of time, and bar code readers and data printers to maintain a traceable path. Direct radical detection and recording are also possible. The hydrophone and thermocouples should be located in the chamber such that they are in communication or contact with the thin film of plasma as it flows across the flat panel.

The apparatus may be constructed such that all of the components are permanent or semi-permanent, i.e., such that all or most of the components are intended to be used repeatedly for the processing of large amounts of plasma. Alternatively, the apparatus may be divided into a permanent or semi-permanent subunit and a disposable subunit. In this embodiment, the permanent or semi-permanent subunit is constructed such that all or most of the components are intended to be used repeatedly for the processing of large amounts of plasma.

The permanent or semi-permanent subunit may comprise:
(1) a source of ultrasonic energy; and
(2) a region designed to accept a chamber, wherein said source of ultrasonic energy is coupled to said region designed to accept said chamber such that ultrasonic energy can be applied to a liquid in a chamber when said chamber is placed in said region.

The permanent or semi-permanent subunit may further comprise other fixed hardware, including a peristaltic pump, a water jacket, and a vacuum pump. The peristaltic pump is positioned such that it can be used to control the flow rate of plasma through the disposable unit. The water jacket is positioned such that it will be between the ultrasound driver and the chamber when the chamber is placed in the region designed to accept it. The vacuum pump is placed such that it can supply a vacuum to the gas above a thin film of plasma flowing through the chamber when the chamber is placed in the region designed to accept it. The permanent or semi-permanent subunit may further optionally comprise a resonator plate which is positioned such that it will be located between the waterjacket and the ultrasound driver.

The disposable subunit may comprise:
(1) a chamber, wherein said chamber has a flat panel, an inlet, and an outlet, and wherein said flat panel of said chamber and said inlet are dimensioned such that plasma flowing through said inlet and across said flat panel to said outlet will form a thin film and travel in plug flow.

The disposable unit may further comprise a second outlet which may be connected to the vacuum pump of the permanent or semi-permanent subunit for supplying a vacuum to the gas above the plasma.

Figure 3:
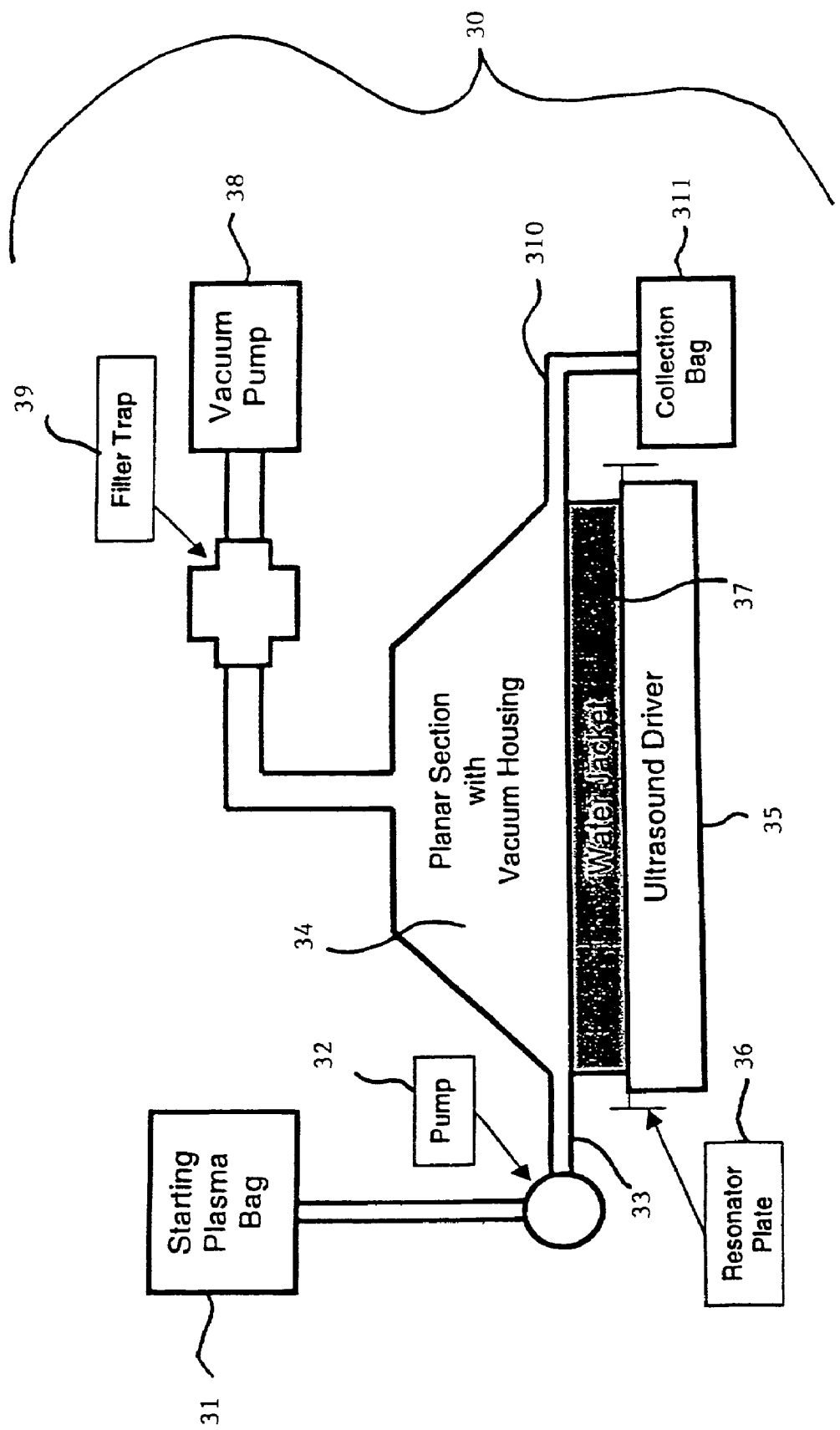
FIG. 3 is a schematic representation of an ultrasound treatment apparatus according to the present invention.
Figure 4:
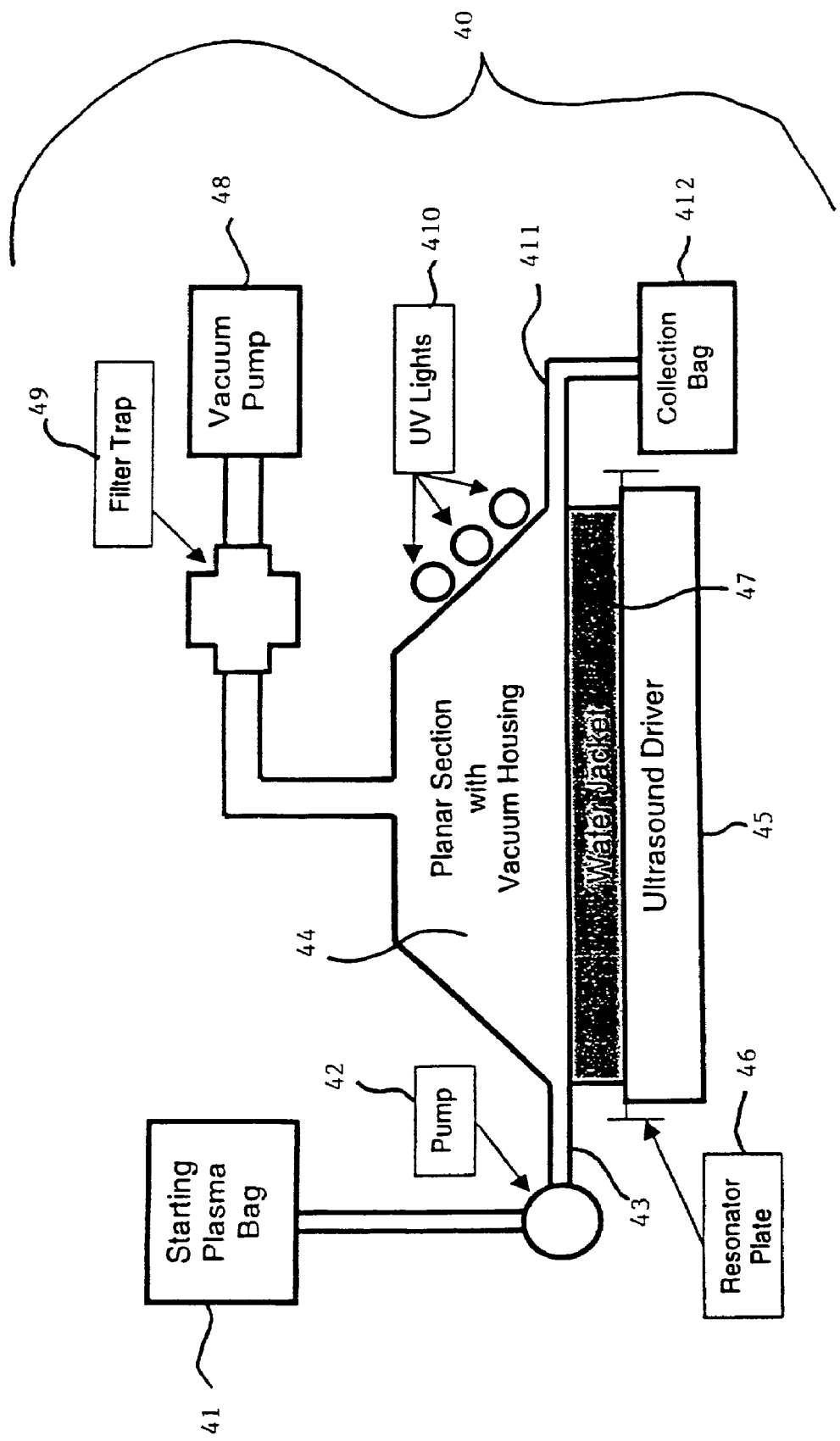
FIG. 4 is a schematic representation of another embodiment of a combined ultrasound treatment and UV treatment apparatus according to the present invention.

The use of a preferred embodiment of the present apparatus will now be described in more detail by referring to FIG. 3. FIG. 3 shows a decontamination system 30 designed for use in a method in which the plasma is decontaminated by the application of ultrasonic energy without application of UVC radiation or subsequent ozone treatment. The plasma enters the system from a plasma bag 31 or other source on the left, with the flow rate of the plasma controlled by a peristaltic pump 32. The plasma flow then crosses a divergent spreader 33, thus yielding a uniform plug flow of a thin film of plasma across the flat panel at the bottom of chamber 34, toward the collection bag 311. (Means for achieving plug flow of the plasma are also shown in FIG. 4. The plasma enters the unit from the left, the flow controlled by a peristaltic pump 42. This flow then crosses a divergent spreader 43, thus yielding a thin film of the plasma, which flows across the flat panel at the bottom of the main chamber 44 in plug flow.) Plug flow is achieved by keeping the planar section short relative to the entrance zone, which guarantees continuous plug flow in this design, using the general fluid mechanics rule that a flow section of about 20 times the inlet width is required to develop laminar flow under non-turbulent, low Reynolds numbers. The flow rate of the plasma across the flat panel is as described above.

The ultrasonic energy is applied to the plasma by means of the ultrasound driver 35, which is coupled to the flat panel at the bottom of chamber 34 via a resonator plate 36. Thus, as the plasma flows across the flat panel, it is sonified from below. The sonification is driven by an ultrasonic driver 35 acting on a metal plate 36 which is resonance coupled for efficient energy transfer.

The temperature of the plasma flowing across the flat panel is controlled by the water jacket 37. The water jacket 37 between resonator plate 36 and the flat panel prevents excess heat from the ultrasonic driver 35 from reaching the plasma; water is an excellent sound transmission medium, and any losses of ultrasonic energy are thus insignificant.

After flowing across the flat panel, the decontaminated plasma then exits the chamber via outlet 310 and enters the collection bag 311.

The gas above the plasma in chamber 34 and gas evolved from the plasma during application of the sonic energy to the plasma are removed from the chamber by the vacuum pump 38. Biological materials such as infectious agents are captured by the filter trap 39 to prevent contamination of the vacuum pump 38.

The entire process may be carried out under refrigeration, and the entire apparatus 30 or at least one or more of the starting plasma bag 31, chamber 34, and collection bag 311 may be contained in one or more refrigeration units.

Apparatus 30 in FIG. 3 may be constructed as a complete permanent or semipermanent unit, with only the starting plasma and collecting plasma bags being disposable or consumable subunits. Alternatively, and preferably, apparatus 30 in FIG. 3 is constructed as a permanent or semi-permanent subunit and a disposable or consumable subunit. In the context of apparatus 30 of FIG. 3, pump 32, ultrasound driver 35, resonator plate 36, water jacket 37, and vacuum pump 38, may be part of the permanent or semi-permanent subunit, while starting plasma bag 31, inlet 33, chamber 34, outlet 310, and collection bag 311 may be part of one or more disposable or consumable units. The vacuum line including the filter trap 39 may be part of either the permanent or semi-permanent subunit or a disposable or consumable subunit.

To keep costs down, the disposable or consumable units, with the exception of the collection bag, may be preferably blow molded from inexpensive plastics. In this regard, it should be noted that the rigorous conditions that apply to the plastics in plasma bags need not be met in the remainder of the disposable unit, because it will never be subjected to freezing, transport, or long term storage. The collection bag, however, preferably should meet these standards. Accordingly, it is preferred to use a conventional plasma bag. Preferably, for compatibility with existing practices, any disposable parts of the present apparatus should have no metal parts so the disposables or consumables can be incinerated.

When the chamber is part of a disposable or consumable unit, the walls of the chamber can be made of quite thin and/or flexible material. In other words, the disposable chamber may be a bag or liner for the region which is designed to accept it. When the chamber is a bag or flexible liner, it may be made to hold a desired shape or to conform to the shape of the region designed to accept it, by applying a slight vacuum to draw the liner out to the required dimensions under differential pressure, thus allowing the use of a very cheap treatment bag as the chamber.

In another preferred embodiment, the disposable bag used as the chamber further comprises a virus tight filter at one end of the bag to equilibrate the pressures inside and outside of the bag during vacuum processing. This FDA approved component also allows for easier mounting of the bag inside the region designed to accept the chamber. In another preferred embodiment, the disposable bag used as the chamber further comprises grommets at the inlet and outlet tubes to prevent them from collapsing during the application of the vacuum.

In another preferred embodiment, the chamber has a roughened inner surface. A roughened inner surface allows the evolved gas bubbles to travel up to local spikes on the bag liner. From these points, the ultrasonic vibrations can dislodge the bubbles relatively easily. For comparison, bubbles flattened along one side of a smooth bag surface are more difficult to remove, even with agitation.

The apparatus may further comprise certain safety features, including electrical shielding, splash guards, and particularly a commercial ultrasound shielding enclosure.

In another preferred variation, the present apparatus may further comprise a device or means for detecting when a particular amount of fluid has been processed. For example, when individual units are being processed into storage containers, it may be preferred to include a scale to detect when the storage container is full. Alternatively, an optical device which measures the level of fluid in the container may also be used.

It may also be preferred to include a scale to measure the amount of fluid in the input container or bag. Specifically, mounting the input bag on a scale (with computer output) provides a means to measure the flow rate, given the time from the digital controller. This flow rate, in turn, provides information which may be used to control the opening or closing of the valve system.

XXII. In a Twenty-second Main Embodiment, the Present Invention Provides an Apparatus for Decontaminating a Fluid, Comprising:
  (1') a means for containing said fluid;
  (2') a means for contacting said fluid with a vacuum; and
  (3') a means for introducing ultrasonic energy into said means for containing said fluid, wherein said means for containing said fluid comprises (i) a means for the introduction of said fluid into said containing means, (ii) a means for said fluid to flow through said containing means, and (iii) a means for the removal of said fluid from said containing means; and wherein said containing means is dimensioned such that a fluid flowing through said containing means will form a thin film and travel in plug flow at least during some portion of its flow through said containing means.

In this twenty-second main embodiment, the "means for containing said fluid" may be the same as described for the "chamber for containing a fluid" described above in the context of the twenty-first main embodiment; the "means for contacting said fluid with a vacuum" may be the same as the "vacuum source coupled to the chamber" described above in the context of the twenty-first main embodiment; and the "means for introducing ultrasonic energy into said means for containing said fluid" may be the same as the "source of ultrasonic energy coupled to the chamber" described above in the context of the twenty-first main embodiment. In addition, all the optional and preferred components described above in the context of the twenty-first main embodiment may also be present in this twenty-second main embodiment.

XXIII. In a Twenty-third Main Embodiment, the Present Invention Provides an Apparatus for Decontaminating a Fluid, Comprising:
  (1) a chamber for containing a fluid;
  (2) a vacuum source coupled to the chamber;
  (3) a source of ultrasonic energy coupled to such chamber; and
  (4) a source of UV, gamma, or x-ray radiation.

In this twenty-third main embodiment, the "chamber for containing a fluid" may be the same as the "chamber for containing a fluid" described above in the context of the twenty-first main embodiment; the "vacuum source coupled to the chamber" may be the same as the "vacuum source coupled to the chamber" described above in the context of the twenty-first main embodiment; and the "source of ultrasonic energy coupled to such chamber" may be the same as the "source of ultrasonic energy coupled to the chamber" described above in the context of the twenty-first main embodiment.

As noted above, the chamber and source of ultrasonic energy in this embodiment may be the same as described above in the context of the twenty-first main embodiment. However, if the source of UV, gamma, or x-ray radiation is placed such that the UV, gamma, or x-ray radiation must pass through a portion of the chamber wall to reach the plasma, then at least that portion of the chamber wall must be sufficiently transparent to the radiation so that the desired degree of decontamination is achieved.

The principle difference between the apparatus of this embodiment and that of the embodiment described above is the presence of the UV, gamma, or x-ray radiation source. The source of UV, gamma or x-ray radiation may be any that is capable of generating radiation of the desired frequency and intensity. Suitable sources of UV include those described above. As for gamma radiation, Cobalt-60 and Cesium-137 are the most common medical application sources. X-rays may be generated by standard, high voltage, electron accelerating sources.

In another preferred embodiment, the apparatus contains a dissolved-oxygen meter inside chamber. The dissolved-oxygen meter is located such that it can detect the oxygen content in a thin film of plasma flowing across the flat panel.

This apparatus may also be constructed such that all of the components are permanent or semi-permanent, i.e., such that all or most of the components are intended to be used repeatedly for the processing of large amounts of plasma. Alternatively, the apparatus may be divided into a permanent or semi-permanent subunit and a disposable subunit. In this embodiment, the permanent or semi-permanent subunit is constructed such that all or most of the components are intended to be used repeatedly for the processing of large amounts of a fluid, such as plasma.

The permanent or semi-permanent subunit comprises:
(1) a source of ultrasonic energy;
(2) a source of UV, gamma, or x-ray radiation; and
(3) a region designed to accept a chamber, wherein said source of ultrasonic energy is coupled to said region designed to accept said chamber such that ultrasonic energy can be applied to a liquid in a chamber when said chamber is placed in said region and wherein said source of UV, gamma, or x-ray radiation is positioned such that UV, gamma, or x-ray radiation can be applied to a liquid in a chamber when said chamber is placed in said region The permanent or semi-permanent subunit may further comprise other fixed hardware, including a peristaltic pump, a water jacket, and a vacuum pump. The peristaltic pump is positioned such that it can be used to control the flow rate of plasma through the disposable unit. The water jacket is positioned such that it will be between the ultrasound driver and the chamber when the chamber is placed in the region designed to accept it. The vacuum pump is placed such that it can supply a vacuum to the gas above a thin film of plasma flowing through the chamber when the chamber is placed in the region designed to accept it. The permanent or semi-permanent subunit may further optionally comprise a resonator plate which is positioned such that it will be located between the water jacket and the ultrasound driver.

The disposable subunit of this embodiment is essentially the same as that described above, with the proviso that at least one portion of the chamber wall must be constructed of material which is sufficiently UV-, gamma-, and/or x-ray-transparent, so that the plasma can be effectively decontaminated by the UV, gamma, and/or x-ray-radiation.

XXIV. In a Twenty-fourth Main Embodiment, the Present Invention Provides an Apparatus for Decontaminating a Fluid, Comprising:
(1') a means for containing said fluid;
(2') a means for contacting said fluid with a vacuum;
(3') a means for introducing ultrasonic energy into said means for containing said fluid; and
(4') a means for the treatment of said fluid with UV, gamma, or x-ray radiation.

In this twenty-fourth main embodiment, the "means for containing said fluid" may be the same as the "chamber for containing a fluid" described above in the context of the twenty-first and twenty-third main embodiments; the "means for contacting said fluid with a vacuum" may be the same as the "vacuum source coupled to the chamber" described above in the context of the twenty-first and twenty-third main embodiments; the "means for introducing ultrasonic energy into said means for containing said fluid" may be the same as the "source of ultrasonic energy coupled to such chamber" described in the context of twenty-first and twenty-third main embodiments; and the "means for the treatment of said fluid with UV, gamma, or x-ray radiation" may be the same as the "source of UV, gamma, or x-ray radiation" described above in the context of the twenty-third main embodiment. In addition, all the optional and preferred components described above in the context of the twenty-first main embodiment may also be present in this twenty-fourth main embodiment.

XXV. In a Twenty-fifth Main Embodiment, the Present Invention Provides an Apparatus for Decontaminating a Fluid, Comprising:
(1) a chamber for containing a fluid;
(2) a vacuum source coupled to the chamber;
(3) a source of ultrasonic energy coupled to such chamber; and
(4) a source of ozone, wherein said chamber comprises: (i) an inlet for introducing ozone from the source of ozone; (ii) an inlet for introducing plasma; and (iii) a device for mixing ozone from the source of ozone with a fluid.

The ozone may be generated as described above, in the context of the thirteenth through twentieth main embodiments. Having thus generated the ozone, the next concern is how to apply it to the fluid.

In the present preferred embodiment, two alternative methods or contactors may be used.

Accordingly, in a preferred embodiment the ozone is mixed with the fluid with a contactor which comprises:
(1) a substrate which has a lower surface and an upper surface and which has a plurality of passage-ways connecting said lower surface with said upper surface;
(2) a source of ultrasonic energy coupled to said substrate, such that said ultrasonic energy is introduced into the fluid by the vibration of said substrate;
(3) a source of ozone connected to said lower surface of said substrate.

In this preferred contactor, the ozone is introduced into the fluid by passing through the same substrate which couples the source of ultrasonic energy to the fluid. The ozone passes through the passage-ways in the substrate and is introduced into the fluid in the form of bubbles. The size of the bubbles may be controlled, at least in part, by controlling the size of the openings of the passage-ways to the fluid. Suitably, the openings are circular in shape with the diameters of the openings of the passage-ways having a size of 25 to 1000 microns, preferably 50 to 500 microns, depending on the ultrasonic frequency range. The size of the ozone bubbles introduced into the fluid is also influenced, in part, by the frequency and amplitude of the vibration of the substrate. Typically, the substrate will vibrate at a frequency of 20 to 250 kHz, preferably 20 to 100 kHz, with an amplitude greater than the diameter of the openings.

The first part of the ozone treatment system is the plasma input reservoir, which is in direct contact with heat transfer plates for cooling. As noted in a previous section, cooled liquids are much more receptive to gasses. The overall geometry of the reservoir is a cylinder, decreasing in size towards the base. At the bottom of this cylinder, the reservoir becomes rectangular in cross section. This rectangular cross section matches the inlet of the ozone nozzle. This nozzle is shaped like a "V" with small (several micron) holes on both sides of each planar section. These holes connect to an ozone source. Ultrasound is applied normal to the plane of the "V" along the direction of the bottom channel.

On the opposite side of the nozzle, a similar reservoir is placed to collect the treated fluid. The height of this second reservoir, however is less than the height of the first so that the liquid flows under gravity; alternatively, the fluid can be pumped.

With this arrangement, the ozone enters the liquid already divided into "ligaments." The direct action of the ultrasound on these gaseous ligaments is immediate disruption into bubbles. It should be noted in particular that the motion of the ultrasonic horn is on the order of a mm, which is much greater than the ozone orifice diameters. As such, the fine gas bubbles are typically spread over a wide area. Also, this motion allows many orifices to be spaced close together, with subsequent rows staggered, to yield a quite uniform distribution. In practice, fewer orifices are placed on the inlet side because the incoming downward flow tends to force the rising bubbles together, leading to undesirable larger sizes. Conversely, buoyancy on the exit side has the opposite effect, so more gas can be introduced here.

There are several benefits of such an arrangement. First, the fluid in the reservoir is immediately exposed to some gas, thus improving the overall treatment time. Second, the requirement that all of the liquid must pass through the nozzle ensures uniform treatment. Third, the continued ozone treatment on the exit side also extends the total treatment time, under good mixing conditions. Fourth, the small, micron-sized bubbles are much less than the optimum for resonance for a typical 20 kHz source, and are therefore rapidly driven into solution by the applied ultrasound, as discussed earlier. Finally, the low amplitude source improves mixing and diffusion, without excessive bubble growth or protein damage due to cavitation.

Allowing the narrow sides of the "V" to flex slightly under ultrasonic motion can further enhance this mixing. In this case, the flexing allows the essentially incompressible fluid to move more readily relative to the orifices of the nozzle. In addition, a single driver at the base of the "V" is more cost effective than a pair of drivers on each side.

After ozone treatment, the liquid is then collected into a second reservoir, as described above. From here, the liquid is then pumped by a peristaltic unit through a heater into a vacuum/ultrasound degasser as described earlier. As described earlier, the fluid is then partially degassed, preferentially removing the oxygen while leaving the ozone. After degassing at this slightly elevated temperature, the fluid is then recycled into the starting reservoir.

The entire process can be repeated as many times as desired. In this process, the overall intent is to achieve a high concentration of ozone rapidly. For optimum time utilization, part of the fluid can be in the degassing component while the remainder of the fluid is in the ozone nozzle component. Some of the material is thus continuously being processed, thereby decreasing the overall system time requirements.

The ozone flow rate into the fluid depends on the pressure applied to the lower surface of the substrate and on the size and density of the passage-ways. As noted above, the size of the passage-ways, in part, determines the size of the bubbles introduced into the fluid. Also as noted above, the size of the bubbles is important because bubbles greater than a critical size are stable and grow so large that they escape the liquid, while bubbles smaller than this critical size are unstable and are driven back into the solution by the ultrasound. Because the critical size limit depends on the frequency of the ultrasound, all bubbles less than the critical size are suitable.

Thus, the amount of ozone introduced into the fluid is typically controlled by varying the pressure of ozone applied to the lower surface of the substrate and by careful selection of the size and the density of passage-ways in the substrate. Typically, the ozone is applied to the lower surface of the substrate at a flow velocity of 1 to 10 mm/sec, preferably 1 to 5 mm/sec. The critical factor limiting the flow velocity on the ozone is the exit pressure, after the ozone leaves the passage-ways. Specifically, it is desirable that the gas be moving slowly, on the order of less than 1 cm/sec, along with negligible residual pressure, to prevent damage to the delicate proteins and/or any cells. For example, passing the output of the above described ozone generator through 400 holes each of 75 micron diameter yields a maximum velocity of about 0.6 cm/sec. In actual practice, the flow velocity is much slower due to pressure losses, as desired. Using 100 holes per square cm, distributed as described above, yields a total surface area of 4 cm$^2$.

In one particularly preferred sub-embodiment, the substrate is part of a v-shaped trough, with one "leg" of the "v" taller than the other. The inside surface of the tall "leg" corresponds to the upper surface of the substrate described above, and the outside surface of the tall "leg" corresponds to the lower surface of the substrate described above. The fluid flows down the inside surface of the tall "leg" (the upper surface of the substrate), where it is effectively contacted with the ozone, to the bottom and then up and over the short "leg."

In another particularly preferred sub-embodiment, the substrate forms part of a hollow apparatus which has an approximate U shape. In this preferred sub-embodiment, the fluid flows from an inlet (preferably after degassing and even more preferably after exposure to UV, gamma, and/or x-ray radiation). In one embodiment, the outside member of the hollow "U," corresponds to the substrate, and its inside surface corresponds to the upper surface of the substrate, while its outside surface corresponds to the lower surface of the substrate. In another embodiment, both the inside and outside members of the hollow "U" correspond to the substrate, with both inside surfaces corresponding to the upper surface of the substrate and both outside surfaces corresponding to the lower surface of the substrate.

XXVI. In a Twenty-sixth Main Embodiment, the Present Invention Provides an Apparatus for Decontaminating a Fluid, Comprising:

(1') a means for containing said fluid;

(2') means for contacting said fluid with a vacuum;

(3') a means for introducing ultrasonic energy into said means for containing said fluid; and (4') a means for generating ozone, wherein said means for containing said fluid comprises: (i) a means for the introduction of ozone from said means for generating ozone into said containing means; (ii) a means for the introduction of said fluid into said containing means; and (iii) a means for mixing said ozone from said means for generating ozone with said fluid in said containing means.

In this twenty-sixth main embodiment, the "means for containing said fluid" may be the same as the "chamber for containing a fluid" described above in the context of the twenty-fifth main embodiment; the "means for contacting said fluid with a vacuum" may be the same as the "vacuum source coupled to the chamber" described above in the context of the twenty-fifth main embodiment; the "means for introducing ultrasonic energy into said means for containing said fluid" may be the same as the "source of ultrasonic energy coupled to such chamber" described above in the context of the twenty-fifth main embodiment; and the "means for generating ozone" may be the same as the "source of ozone" described above in the context of the twenty-fifth main embodiment. Moreover, the "(i) a means for the introduction of ozone from said means for generating ozone into said containing means" and the "(iii) a means for mixing said ozone from said means for generating ozone with said fluid in said containing means" may together form any of the ozone contactors described above in the context of the twenty-fifth main embodiment.

XXVII. In a Twenty-seventh Main Embodiment, the Present Invention Provides an Apparatus for Decontaminating a Fluid, Comprising:
  (1) a chamber for containing a fluid;
  (2) a vacuum source coupled to the chamber;
  (3) a source of ultrasonic energy coupled to such chamber;
  (4) a source of UV, gamma, or x-ray radiation; and
  (5) a source of ozone, wherein said chamber comprises: (i) an inlet for introducing ozone from the source of ozone; (ii) an inlet for introducing a fluid; and (iii) a device for mixing ozone from the source of ozone with a fluid.

In this twenty-seventh main embodiment: (1) the "chamber for containing a fluid;" (2) the "vacuum source coupled to the chamber;" (3) the "source of UV, gamma, or x-ray radiation;" (4) the "source of ultrasonic energy coupled to such chamber;" and (5) the "source of ozone" may be any of the corresponding elements described above in the twenty-first, twenty-third, and twenty-fifth main embodiments. Moreover, the "device for mixing ozone from the source of ozone with a fluid" may be any of the ozone contactors described above in the context of the twenty-fifth main embodiment.

Thus, the apparatus of the twenty-seventh main embodiment is designed for implementation of a process in which the fluid is first degassed, then exposed to UV, gamma, or x-ray radiation, and then treated with ozone, i.e., the methods of main embodiments seventeen through twenty.

XXVIII. In a Twenty-eighth Main Embodiment, the Present Invention Provides an Apparatus for Decontaminating a Fluid, Comprising:
  (1') a means for containing said fluid;
  (2') a means for contacting said fluid with a vacuum;
  (3') a means for introducing ultrasonic energy into said means for containing said fluid;
  (4') a means for the treatment of said fluid with UV, gamma, or x-ray radiation; and
  (5') a means for generating ozone, wherein said means for containing said fluid comprises: (i) a means for the introduction of ozone from said means for generating ozone into said means for containing; (ii) a means for the introduction of said fluid into said means for containing; and (iii) a means for mixing said ozone from said means for generating ozone with said fluid in said means for containing.

In this twenty-eighth main embodiment, the "means for containing said fluid" may be the same as the "chamber for containing a fluid" described above in the context of the twenty-first, twenty-third, twenty-fifth, and twenty-seventh main embodiments; the "means for contacting said fluid with a vacuum" may be the same as the "vacuum source coupled to the chamber" described above in the context of the twenty-first, twenty-third, twenty-fifth, and twenty-seventh main embodiments; the "means for introducing ultrasonic energy into said means for containing said fluid" may be the same as the "source of ultrasonic energy coupled to such chamber" described above in the context of the twenty-first, twenty-third, twenty-fifth, and twenty-seventh main embodiments; the "means for the treatment of said fluid with UV, gamma, or x-ray radiation" may be the same as the "source of UV, gamma, or x-ray radiation" described above in the context of the seventh main embodiment; and the "means for generating ozone" may be the same as the "source of ozone" described above in the context of the twenty-fifth and twenty-seventh main embodiments. Moreover, the "(i) a means for the introduction of ozone from said means for generating ozone into said means for containing" and "(iii) a means for mixing said ozone from said means for generating ozone with said fluid in said means for containing" may together form any of the contactors described above.

XXIX. In a Twenty-ninth Main Embodiment, the Present Invention Provides an Apparatus for Contacting Ozone with a Liquid, which Comprises:
  (1) a substrate which has a lower surface and an upper surface and which has a plurality of passage-ways connecting said lower surface with said upper surface;
  (2) a source of ultrasonic energy coupled to said substrate, such that said ultrasonic energy is introduced into a liquid by the vibration of said substrate;
  (3) a source of ozone connected to said lower surface of said substrate.

This twenty-ninth main embodiment corresponds substantially to the contactor shown in FIG. 8, which is described in detail below.

The basic principles behind the ozone contactor could also be applied to adding other gasses to liquids. Specifically, the underlying principle is to degas the liquid first, and then add the desired gasses immediately afterward, using a sonic assist contactor. Finally, partial degassing to remove reacted products and/or undesired species should then be done.

Of course, the most common application liquid is water, but this could be extended to include aqueous solutions, or even other liquids. The gasses could include everything from ozone to carbon monoxide or dioxide to various nitrogen compounds, etc. As such, the end product would not necessarily be something for sterilization, but instead could include various feedstocks for the chemical industry.

XXX. In a Thirtieth Main Embodiment, the Present Invention Provides an Apparatus for Contacting a Gas, e.g., Ozone, with a Fluid, said Apparatus Comprising:
  (1) a rotatable chamber;
  (2) a source of a gas connected to said chamber; and
  (3) a source of ultrasonic energy coupled to said chamber, wherein said chamber comprises an a fluid inlet;

wherein said chamber comprises a first sidewall and a second sidewall and said first and second sidewalls are positioned opposite to each other;

wherein said chamber further comprises a plurality of partitions, and said partitions are attached to said first and second sidewalls in an alternating arrangement, and each partition attached to said first sidewall projects toward said second sidewall, and each partition attached to said second sidewall projects toward said first sidewall, such that said plurality of partitions forms a plurality of shelves;

wherein said inlet is positioned in said chamber such that a fluid entering said chamber through said inlet occupies a first shelf;

wherein said chamber is capable of rotating such that on rotation of 90 to −90° of said chamber fluid which occupies said first shelf will flow to a second shelf;

wherein said source of gas is connected to said chamber to permit mixing of a gas with a fluid in said chamber; and wherein said source of ultrasonic energy is coupled to at least one of said partition, to permit application of ultrasonic energy to fluid which occupies a shelf formed by said at least one partition.

The apparatus of this thirtieth main embodiment corresponds to that depicted in FIG. 11 and which is described below. The contactor of this thirtieth main embodiment is especially useful for contacting ozone with fluids which contain platelets, and its use and operation and described in detail in connection with the description of FIG. 11. However, it is noted that the discussions above which relate to the materials used for the chamber, the source of ozone, and the source of ultrasonic energy apply to this thirtieth main embodiment.

Of course it is to be understood that any and all of the steps and/or components described in the above-disclosed methods and apparatus may be carried out or operated by means of computer control. Such computer control substantially reduces the possibility and risk of problems and/or malfunctions resulting from human error.

XXXI. The Figures:

Various other objects, features and attendant advantages of the present invention will be more fully appreciated as the same becomes better understood from the following detailed description when considered in connection with the accompanying drawings in which like reference characters designate like or corresponding parts throughout the several views.

FIG. 1 is a schematic flow chart of the method of the fifteenth through eighteenth main embodiments, which are especially preferred. In the first step shown in FIG. 1, the fluid is subjected to a temperature preparation step. In a second step, the fluid is degassed by application of ultrasonic energy. In the third step shown in FIG. 1, the degassed fluid is irradiated. In the fourth step shown in FIG. 1, the irradiated fluid is treated with ozone.

Although these steps are shown as progressive, this does not mean that the technology must perform only one function at a time. In this regard, it should be noted that the first step in the process (heating of the entire plasma bag) may require an hour or more. Likewise, degassing and UV exposure may take a half-hour or so, while the ozone exposure may take a similar time, or more if multiple cycles are used. To avoid tying up the entire machine during these separate cycles, a clinical unit would have two or more bags being warmed simultaneously. As one of these bags reaches the completion of its heat treatment, it is degassed, etc., while the other bag continues its heat processing. Likewise, at the end of the process, several different bags can be undergoing ozone exposure, while other units are being heated, degassed, etc. As a result, the unit is kept processing at all times for maximum return on investment.

Figure 2:
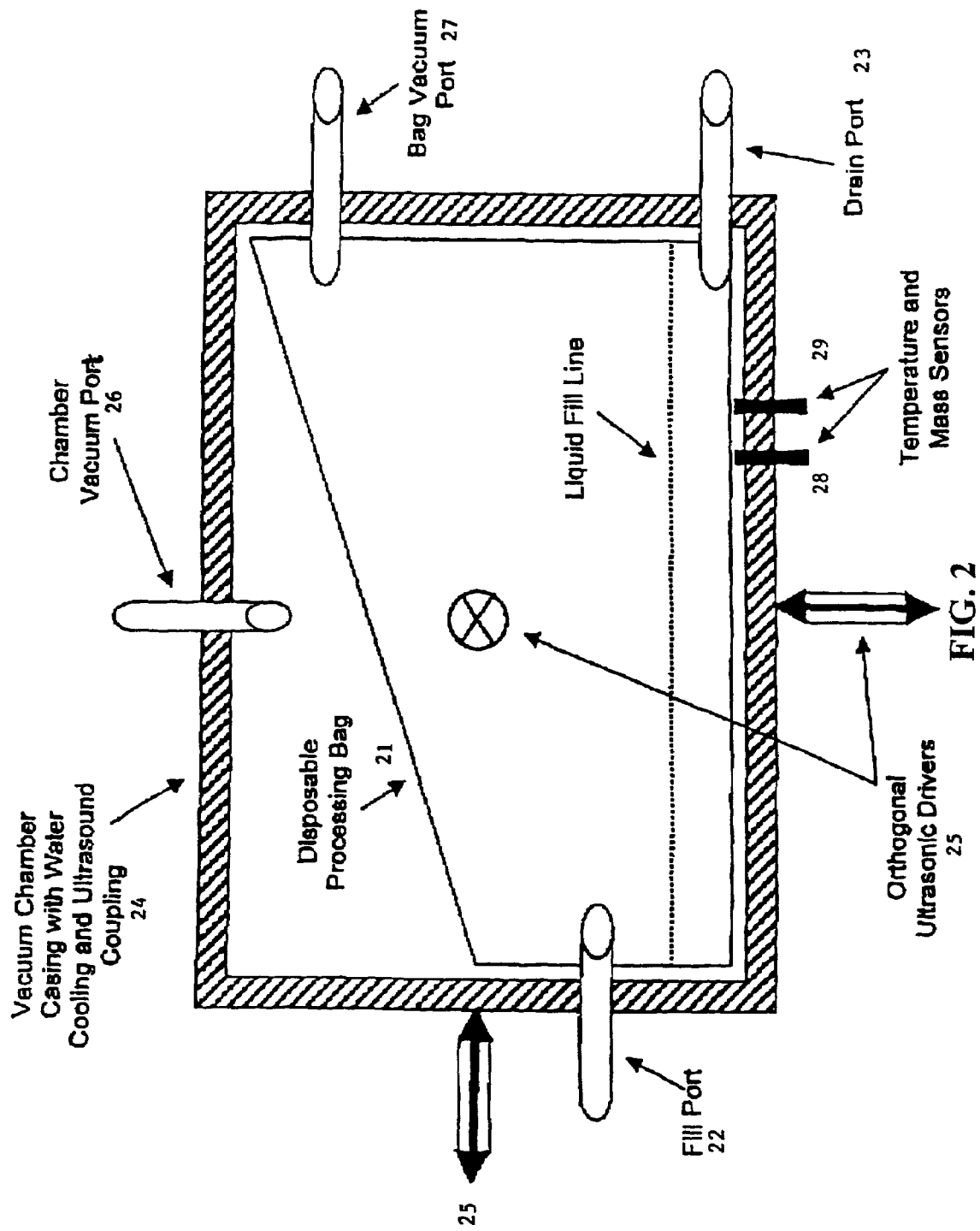
FIG. 2 is a schematic representation of an ultrasonic degassing chamber according to the present invention.

FIG. 2 shows a preferred apparatus which is useful for ultrasonic degassing as carried out in the third and fourth main embodiments. When using the apparatus shown in FIG. 2, the fluid enters the chamber, which is a flexible, disposable bag, 21, through an inlet, 22, and eventually exits through a drain port, 23. The disposable bag is received inside a vacuum chamber, 24, which is equipped with water cooling and ultrasonic drivers, 25, such that ultrasonic energy is introduced into the fluid. The flexible, disposable bag, 21, is maintained in an expanded shape by means of a vacuum applied to the outside of the bag via a chamber vacuum port, 26 or by fasteners mated to the fixed vacuum chamber walls. A vacuum is applied to the fluid inside the bag via bag vacuum port, 27. The vacuum chamber, 24, is also equipped with temperature and mass sensors, 28 and 29, so that the flow rate and heating due to the introduction of ultrasonic energy may be monitored and controlled.

FIG. 3 shows a preferred apparatus of the present invention which corresponds to the twenty-first and twenty-second main embodiments. In the embodiment shown in FIG. 3, the fluid is introduced into the main chamber 34 through an inlet 33 from a starting plasma bag 31. The feed rate of the fluid may be controlled by pump 32. The fluid is sonified from below, as it flows across the planar section of the main chamber 34. The ultrasonic energy is provided by the ultrasound driver 35, which is coupled to the fluid via the resonator plate 36. The temperature of the fluid may be controlled by a water jacket 37. During sonification, the dissolved gasses, including oxygen may be released from the fluid and then trapped in the plastic housing. This housing and the planar section are a sealed unit, thus preventing external air from being drawn into the system. Evolved gasses may then captured by the vacuum pump 38. For safety, the vacuum line may incorporate a sterile coupling and a filter trap 39 to prevent any pathogens from contaminating the vacuum pump. The decontaminated fluid is then collected in the collection bag 311.

FIG. 4 shows another preferred apparatus of the present invention which corresponds to the twenty-first and twenty-second main embodiments. FIG. 4 shows a decontamination system 40 designed for use in a method in which the fluid, in particular plasma, is decontaminated by the application of ultrasonic energy without application of UVC radiation or subsequent ozone treatment. The plasma enters the system from a plasma bag 41 or other source on the left, with the flow rate of the plasma controlled by a peristaltic pump 42. The plasma flow then crosses a divergent spreader 43, thus yielding a uniform plug flow of a thin film of plasma across the flat panel at the bottom of chamber 44.

The ultrasonic energy is applied to the plasma by means of the ultrasound driver 45, which is coupled to the flat panel at the bottom of chamber 44 via a resonator plate 46. Thus, as the plasma flows across the flat panel, it is sonified from below. The sonification is driven by an ultrasonic driver 45 acting on a metal plate 46 which is resonance coupled for efficient energy transfer.

The temperature of the plasma flowing across the flat panel is controlled by the water jacket 47. The water jacket 47 between resonator plate 46 and the flat panel prevents heat from the ultrasonic driver 45 from reaching the plasma;

water is an excellent sound transmission medium, and any losses of ultrasonic energy are thus insignificant.

The gas above the plasma in chamber 44 and the gas evolved (particularly oxygen) from the plasma during application of the sonic energy to the plasma are removed from the chamber 44 by vacuum pump 48. Chamber 44 is a sealed unit, thus preventing external air from being drawn into the system. For safety, the vacuum line incorporates a sterile coupling and a filter trap 49 to prevent any pathogens from entering into and contaminating the vacuum pump.

After the plasma has been de-oxygenated, the plasma then passes under irradiation source (in this case, UV lights) 410 for decontamination. Note that the water jacket 47 extends under this section to prevent excess heating of the plasma by the UV lights 410. In FIG. 4, the ultrasound driver 45 also extends under the section in which the plasma passes under the UV lights 410. Extension of the ultrasound driver 45 under this section provides enhanced decontamination due to improved mixing of the plasma during UV exposure, as well as the dispersal of any aggregates. In an alternative arrangement, the ultrasound generator does not extend under the region where the plasma passes under the UV lights 410. However, even when the ultrasound generator does not extend under the region where the plasma passes under the UV lights 410, it is preferred that the water jacket 47 extends under the region where the plasma passes under the UV lights 410.

After UV (or gamma ray or x-ray) exposure in this section, the flow then enters a converging zone (outlet) 411, which leads to a tube connected to a collection vessel or bag 412 for the decontaminated product. Optionally, the flow may pass through a converging zone, which leads to a tube that passes through an optional peristaltic pump and then into collection bag 412.

The entire process may be carried out under refrigeration, and the entire apparatus 40 or at least one or more of the starting plasma bag 41, chamber 44, and collection bag 412 may be contained in one or more refrigeration units.

Apparatus 40 in FIG. 4 may be constructed as a complete permanent or semipermanent unit, with only the starting plasma and collecting plasma bags being disposable or consumable subunits. Alternatively, and preferably, apparatus 40 in FIG. 4 is constructed as a permanent or semipermanent subunit and a disposable or consumable subunit. In the context of apparatus 40 of FIG. 4, pump 42, ultrasound driver 45, resonator plate 46, waterjacket 47, and vacuum pump 48, may be part of the permanent or semipermanent subunit, while starting plasma bag 41, inlet 43, chamber 44, outlet 411, and collection bag 412 may be part of one or more disposable or consumable units. The vacuum line including the filter trap 49 may be part of either the permanent or semi-permanent subunit or a disposable or consumable subunit.

As described above, the disposable or consumable units, with the exception of the collection bag, may be preferably blow molded from inexpensive plastics, while it is preferred to use a conventional plasma bag and the disposable parts of the present apparatus should have no metal parts so they can be incinerated.

When the chamber is part of a disposable or consumable unit, the chamber walls can be made of quite thin and/or flexible material, with only a small window for UV transmission directly under the lamps. In other words, the disposable chamber may be a bag or liner for the region which is designed to accept it. When the chamber is a bag or flexible liner, it may be made to hold a desired shape or to conform to the shape of the region designed to accept it, by applying a slight vacuum to draw the liner out to the required dimensions under differential pressure, thus allowing the use of a very cheap treatment bag as the chamber. An additional enhancement is the presence of another window in the bottom of the bag to allow exposure from both sides of the fluid layer by a second source of UV, gamma, or x-ray radiation.

In another preferred embodiment, the disposable bag used as the chamber further comprises a virus tight filter at one end of the bag to equilibrate the pressures inside and outside of the bag during vacuum processing. This FDA approved component also allows for easier mounting of the bag inside the region designed to accept the chamber. In another preferred embodiment, the disposable bag used as the chamber further comprises grommets at the inlet and outlet tubes to prevent them from collapsing during the application of the vacuum.

In another preferred embodiment, the chamber has a roughened inner surface. A roughened inner surface allows the evolved gas bubbles to travel up to local spikes on the bag liner. From these points, the ultrasonic vibrations can dislodge the bubbles relatively easily. For comparison, bubbles flattened along one side of a smooth bag surface are more difficult to remove, even with agitation.

This apparatus may further comprise certain safety features, including electrical shielding, splash guards, and particularly a commercial ultrasound shielding enclosure.

In the embodiment shown in FIG. 4, the plasma is sonified from below, as it flows across the planar section at the bottom of the main chamber 44. During sonification, the dissolved gasses, including oxygen are thus released from the plasma and are then trapped in the plastic housing. This housing and the planar section are a sealed unit, thus preventing external air from being drawn into the system. The evolved gasses are then captured by the vacuum pump. For safety, the vacuum line incorporates a sterile coupling and a filter trap to prevent any pathogens from contaminating the vacuum pump.

Certain of the components of the apparatus shown in FIG. 4, as well as certain optional components not shown in FIG. 4 will now be discussed in more detail.

1. Input reservoir, 41. The first of these components is simply a bag to receive the output from the degassing unit. For those materials requiring tight temperature control, this reservoir incorporates a heat exchanger. In extreme cases, such as platelets, this reservoir is preceded by a heating/cooling pack as described for the inlet to the degassing unit. With or without heat transfer capabilities, however, the main function of the reservoir is simply to provide a uniform pressure head for the gravity flow throw the rest of the system. As such, the reservoir is broad and shallow, so that there is relatively little pressure difference between a fall reservoir and a nearly empty reservoir.

2. UVC lamps, 410. To achieve rapid and thorough processing, high intensity UV lamps are necessary. Several such UVC sources have recently been marketed (Spectronics Corporation, Westbury N.Y., and UVItech, Cambridge, England). Unfortunately, these lamps also produce a great deal of heat, and any such heating must be controlled to avoid protein damage. One means of obtaining this control is simply to blow air across the UV sources, which is indeed one of the reasons for performing UV exposure at atmospheric, instead of vacuum, conditions. A second consideration is that the cell does not need to be exposed to the lamps at all times. For example, if there is a delay between batches of fluid from the degassing unit, exposing the cell contents to the lamps would result in excessive UV exposure. To avoid protein damage during such times, the beam path must be interrupted. There are several possible ways of achieving this interruption in practice. One option is simply to turn off the UV lamps. This approach is quite simple, and is preferred in those cases in which the lamps can be restarted rapidly. For those lamps that require a relatively long warming time, however, power cycling is not an option. In this case, the cell can be removed from the beam path, but this is difficult for those applications in which the cell is attached to numerous mounts, tubes, etc. The preferred approach, however, is to use a shutter arrangement between the sources and the flow cell to block the light when necessary.

In addition, there is also the problem of direct radiative heating of the sample. In this case, the incoming radiation generates heat in the liquid that is not readily dissipated through the flow cell walls. The net result is essentially a greenhouse effect, which is a particular problem for erythrocytes because they are optically dense and red. For cases where this heat is a significant problem, the flow cell is modified to include a thin layer of cooling water or other heat exchange liquid around the material to be treated, but constrained to separate channels. Finally, for protection from lamp failure or from inadvertent leaks, the lamps must be separated from the flow cell by a thin, UV transparent shield.

3. Output pump. At the end of the UV treatment chamber, the connecting hose may lead to an ozone exposure unit, rather than collection bag 412. In this case, the essential problem is that the ozone unit typically operates at much greater pressures than the atmospheric pressure that exists in the UV unit. Thus, some provision must be made to handle this pressure difference. As described earlier for the transition from the vacuum degassing unit to the UV unit, the two alternative approaches are a pressure lock chamber or a peristaltic pump. Again, each has the previously described advantages and disadvantages.

4. Monitoring equipment. As for monitoring, the essential problem is that UV systems tend to degrade over time in a process called "solarization." To compensate for this loss in performance, several UV manufacturers (for example, the Spectroline part of Spectronics Corporation, Westbury, N.Y.) have developed automatic monitoring and correction systems. These units monitor the actual UV emissions, and then adjust the exposure times accordingly. Although originally developed for cross linking UV sensitive reagents onto a substrate, this technology is directly transferable here.

5. Flow regulation. The remaining concern is to control the flow through the system. The most important consideration here is that the liquid must be exposed to the light long enough for effective treatment, but not so long as to lead to excessive protein damage. The approach here is to control the flow as described for the inlet to the degassing unit, using flow restrictions, pulsed flow, mass measurements, etc. The essential consideration here is to keep the UV exposure unit working quickly enough to process continuously all of the output from the degassing unit. In this regard, the reservoir has to maintain sufficient head to pass all liquids rapidly, even though there may be substantial variations in viscosity from one unit to the next. While this holds in most cases, a control loop is also incorporated to terminate flow into the degassing unit if necessary.

System operation: The overall system operation follows more or less from the above component descriptions. Basically, fluid from the degassing unit enters the feed reservoir. Under gravity, the fluid then flows through a valve system to control the flow rate. Next, the fluid enters the UV chamber, which is cooled by water and air flow. Shutters between the lamps and the flow chamber interrupt the light when the flow stops. After treatment, the fluid is then pumped out to the ozone exposure unit, or to a collection bag if ozone is not to be used.

Like the rest of the unit, including the ozone exposure module, the first step in the startup process is to evacuate the fluid path with the vacuum pump. This is necessary to ensure that there is no oxygen in the system that might be absorbed by the fluid, and thus form oxygen radicals during UV exposure.

As for shut down, the exposure chamber should be tilted as described for the degassing unit so that only a minimum amount of fluid is left behind. The reason for this effort is that the fluid is very valuable and thus must be collected as well as possible; furthermore, any residual material is simply a biohazard, thus presenting a disposal problem.

As noted above, it is preferred that the UVC illumination be done from both sides. This provides for much more uniform exposure. In particular, this uniformity makes red blood cell treatment possible; otherwise, the strong absorption by hemoglobin prevents adequate treatment. In this case, using double side exposure allows the use of a flow layer on the order of 10 to 40 microns, more preferably in the range of 30–40 microns. At this thickness, the variation in intensity is less than 10% even for high hematocrit samples. Note that these dimensions are based on the size of erythrocytes, which are about 10 microns in length. Although quite precise, the required level of machining is available from specialized companies, such as Mindrum Precision, Inc., Rancho Cucamonga, Calif. This firm specifies a flatness tolerance of about 0.5 microns for its UV flowcells.

To treat red blood cells effectively, the illuminator must be sonified at low intensity to promote uniform mixing and ensure plug flow. It should be noted that illuminator sonification was previously mentioned to prevent aggregation of plasma proteins.

For easy manipulation, it is preferred that the flexible bags be mounted on a rigid frame that matches the processing equipment. This frame can be either reused or discarded. With or without the use of such frames, the bags should be manufactured with registration holes in their borders. Of course, the frame and/or the processor must have matching pins for these holes. This arrangement thus provides an easy way of aligning the bags in the processor, and also helps to prevent accidental misalignment by the operators.

To achieve the necessary precision, particularly for red blood cell treatment, the frame and/or bag assembly must be mounted in a recess inside the quartz flow cell. As such, the quartz thus provides rigid support after the fluid enters the treatment zone. Also, the quartz surfaces thus are in direct contact at the boundary, thereby ensuring tight tolerances. To avoid excessive pressures during the contact process, the opposing panels are mounted on rubber supports, which compress on contact. Note that the sonification must therefore be applied directly to the panels under this arrangement, which will otherwise excessively damp the sound waves.

The last problem is to control the flow of the system. In a preferred configuration, all of the donation sample is illuminated in one step (for example, plasma or platelets). In this case, all of the degassed liquid is poured into the top of the exposure chamber in one operation. The lamps are then turned on. After the end of the treatment all of the liquid is then drained. The only problem here is that the clamp at the exit of the tube must not shadow the treatment volume. This can be avoided by designing a protrusion onto the clamp to extend sharply beyond the clamp body. Constructing this protrusion from UVC transparent materials, such as Teflon®AF or quartz, eliminates any remaining shadow effects.

FIG. 5 shows another preferred apparatus, which corresponds to the apparatus of the twenty-fifth and twenty-sixth main embodiments and is useful for carrying out the method of the thirteenth through sixteenth main embodiments. In FIG. 5, the fluid, plasma, in the illustrated case, enters the ozonation unit from the plasma bag, 51, via a pump, 52, where it is mixed with ozone in a mixing tip/spray nozzle, 55. The ozone enters the mixing tip/spray nozzle, 55, from an ozone generator, 53, passing through a filter trap, 56. The fluid and the ozone are mixed in the mixing tip/spray nozzle, 55, and enter the reaction vessel, 57, as a spray or mist. The fluid collects at the bottom of the reaction vessel, 57, to the fill line, 511. Ultrasonic energy is applied to the fluid at the bottom of the reaction vessel, 57, via an ultrasound driver, 58, and a water jacket, 510, is placed between the bottom of the reaction vessel, 57, and the ultrasound driver, 58, to control the degree of heating. When the treatment is complete the fluid is drained from the reaction vessel, 57, via a line to a collection bag, 512.

The use of this preferred embodiment of the present apparatus to decontaminate plasma will now be described in more detail by referring to FIG. 5. FIG. 5 shows a decontamination system 50 in which plasma enters the system from a plasma bag 51 or other source on the right, the flow controlled by a peristaltic pump 52. Ozone from a conventional generator 53 is then passed through a connecting tube 54 to the mixing tip/spray nozzle assembly 55. Like the vacuum line in the light exposure line, the ozone feed tube is passed through a filter 56 and trapped across a sterile coupling to prevent inadvertent contamination of the ozone generator 53. After mixing the ozone and plasma, the product is then collected in the reaction vessel 57. Like the processor tray in the light exposure unit, this vessel sits on an ultrasonic driver 58 coupled to a resonator plate 59 and separated from the reaction vessel 57 by a water-driven cooling jacket 510. After sonification, the product is then drained into a collection vessel.

Apparatus 50 in FIG. 5 may be constructed as a complete permanent or semi-permanent unit, with only the starting plasma and collecting plasma bags being disposable or consumable subunits. Alternatively, and preferably, apparatus 50 in FIG. 5 is constructed as a permanent or semi-permanent subunit and a disposable or consumable subunit. In the context of apparatus 50 of FIG. 5, pump, 52, ozone generator, 53, ultrasound driver, 58, resonator plate, 59, and water jacket, 510, may be part of the permanent or semi-permanent subunit, while starting plasma bag, 51, reaction vessel, 57, and collection bag, 512, may be part of one or more disposable or consumable units. The ozone line, 54, including the filter trap, 56, and the mixing tip/spray nozzle, 55, may each be part of either the permanent or semi-permanent subunit or a disposable or consumable subunit.

In another preferred embodiment, the disposable bag used as the chamber further comprises a virus tight filter at one end of the bag to equilibrate the pressures inside and outside of the bag during vacuum processing. This FDA approved component also allows for easier mounting of the bag inside the region designed to accept the chamber. In another preferred embodiment, the disposable bag used as the chamber further comprises grommets at the inlet and outlet tubes to prevent them from collapsing during the application of the vacuum.

In another preferred embodiment, the chamber has a roughened inner surface. A roughened inner surface allows the evolved gas bubbles to travel up to local spikes on the bag liner. From these points, the ultrasonic vibrations can dislodge the bubbles relatively easily. For comparison, bubbles flattened along one side of a smooth bag surface are more difficult to remove, even with agitation.

The main expense of the current disposables is the equipment required to produce thin layers or sprays in which the ozone can make intimate contact with the contaminants. Ultrasound provides several alternatives to this problem, the main benefits being in the mixing process itself. The basis for these effects is the ability of ultrasound to modify the properties of a liquid. One such effect is the tendency for ultrasound to mix gasses into the surface of a liquid if the applicator horn is not deeply immersed into the liquid. Because the resulting poor coupling causes reduced cavitation, such operation of conventional ultrasound equipment is to be avoided (*High Intensity Ultrasonic Processor User's Guide*, Sonics & Materials, Inc. Newton, Conn., 1999).

Reduced cavitation and gas entrapment, however, is just what is required for this project. To encourage these processes, the ozone and plasma will therefore be brought together in a mixing chamber in which a plastic extender is placed just above the plasma surface. When sonified, this extender will then oscillate in and out of the plasma, thus entrapping small ozone pockets 20,000 times per second.

After forming this finely divided mixture, the next step is conceptually similar to the spraying systems, or "nebulizers" of existing ozone technologies. The problem with these conventional systems, however, is that they cause too much shear for plasma proteins. The alternative is to use ultrasound to spray the already partially mixed plasma and ozone mixture, thus yielding even better mixing. Fundamentally, this process is not unique to this application; various ultrasonic nozzles are available commercially to produce a fine, soft spray. The only modification for this process is to use an extended length of plastic tubing as a nozzle, the end of which is free at an antinode to whip under sonification. While this simple arrangement is not as effective as commercial nozzles, it is quite cheap.

Having thus developed a dispersed spray, the next concern is to contain and process it. These goals can be met by directing the spray into a small plastic reaction vessel. The spray then accumulates into pools, which coalesce into a volume of liquid. When sonified at low intensity, any ozone gas bubbles disperse, aided by the enhanced diffusion and decreased viscosity effects of ultrasound.

Next, a short burst of more intense ultrasound is applied to the reaction vessel. At this time there is some radical formation, but this can be minimized by using a reaction vessel shaped like an hourglass, thus yielding progressively less surface area up to the fill line at the midpoint. Much more important than radical formation, however, is the increase in ozone reaction speed. This speed is crucial not only for overall processing speed, but also because ultrasound is quite effective at removing ozone from aqueous solutions. The apparent mechanism behind this rapid purging is partly due to increased chemical reactivity and partly due to simple degassing. Effective decontamination thus requires rapid ozone and pathogen reactions, before the ozone is lost.

The overall arrangement for such a unit is shown in FIG. 5. As done for the light exposure unit, the first step in this process is to use a peristaltic pump to control the flow rate of the plasma. Ozone from a conventional generator is then passed through a connecting tube to the mixing tip/spray nozzle assembly. Like the vacuum line in the light exposure line, the ozone feed tube is filtered and trapped across a sterile coupling to prevent inadvertent contamination of the ozone generator. After mixing the ozone and plasma, the product is then collected in the reaction vessel. Like the processor tray in the light exposure unit, this vessel sits on an ultrasonic driver separated by a water cooling pack. After sonification, the product is then drained into a collection vessel.

Figure 6:
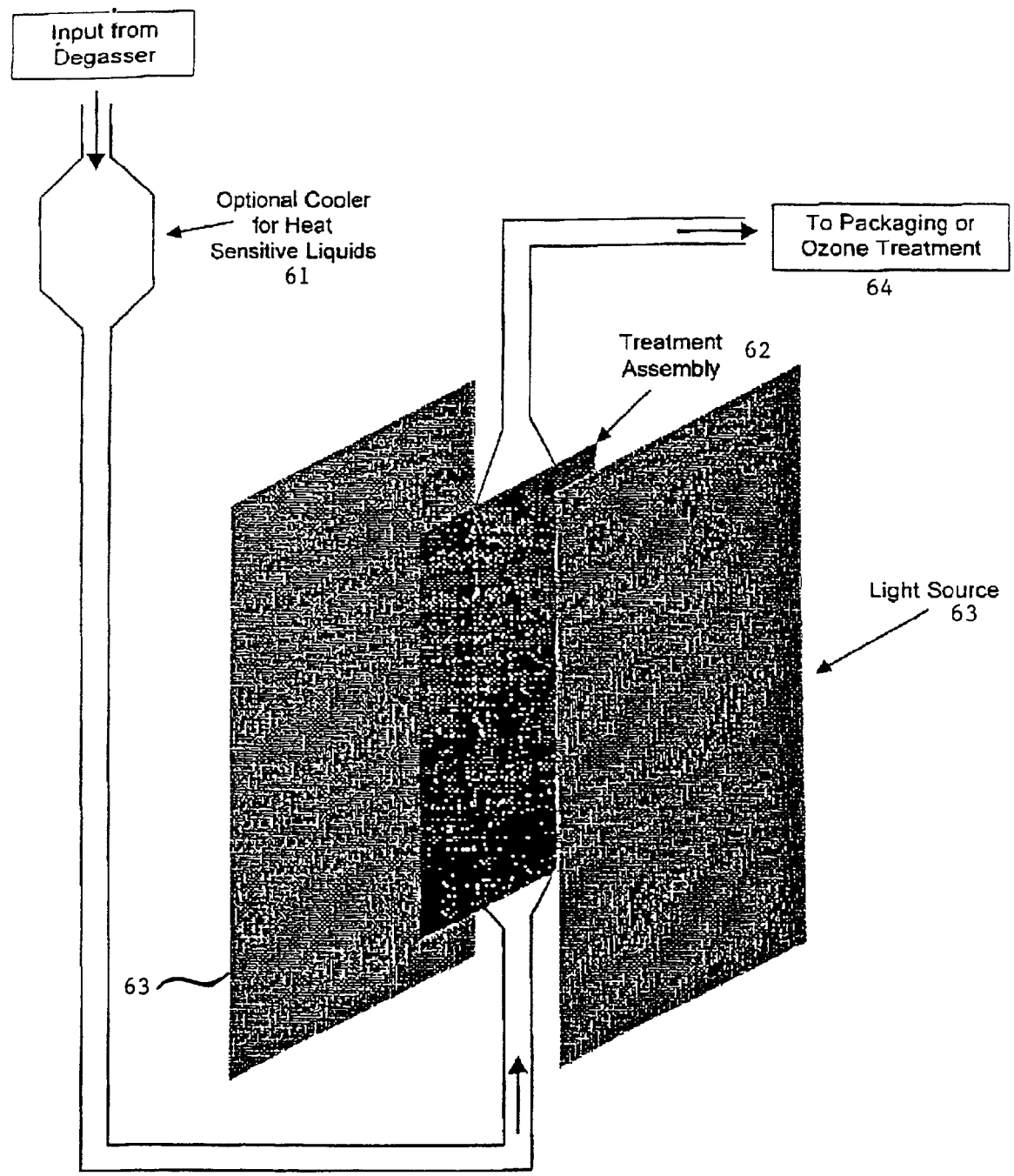
FIG. 6 is a cross-sectional view of an UV treatment chamber and components according to the present invention.

FIG. 6 depicts a portion of another preferred apparatus of the present invention, which corresponds to the twenty-fifth and twenty-sixth main embodiments and is useful for carrying out the method of the thirteenth through sixteenth main embodiments, in continuous, as opposed to batch-wise manner. In FIG. 6, the fluid enters from an earlier ultrasonic degassing unit, which is not shown, and may pass through an optional cooler, 61. The fluid then is formed into a thin film in the treatment assembly, 62, where it passes between one, preferably two, light sources, 63. The fluid then passes on to ozone treatment or packaging, 64.

Figure 7:
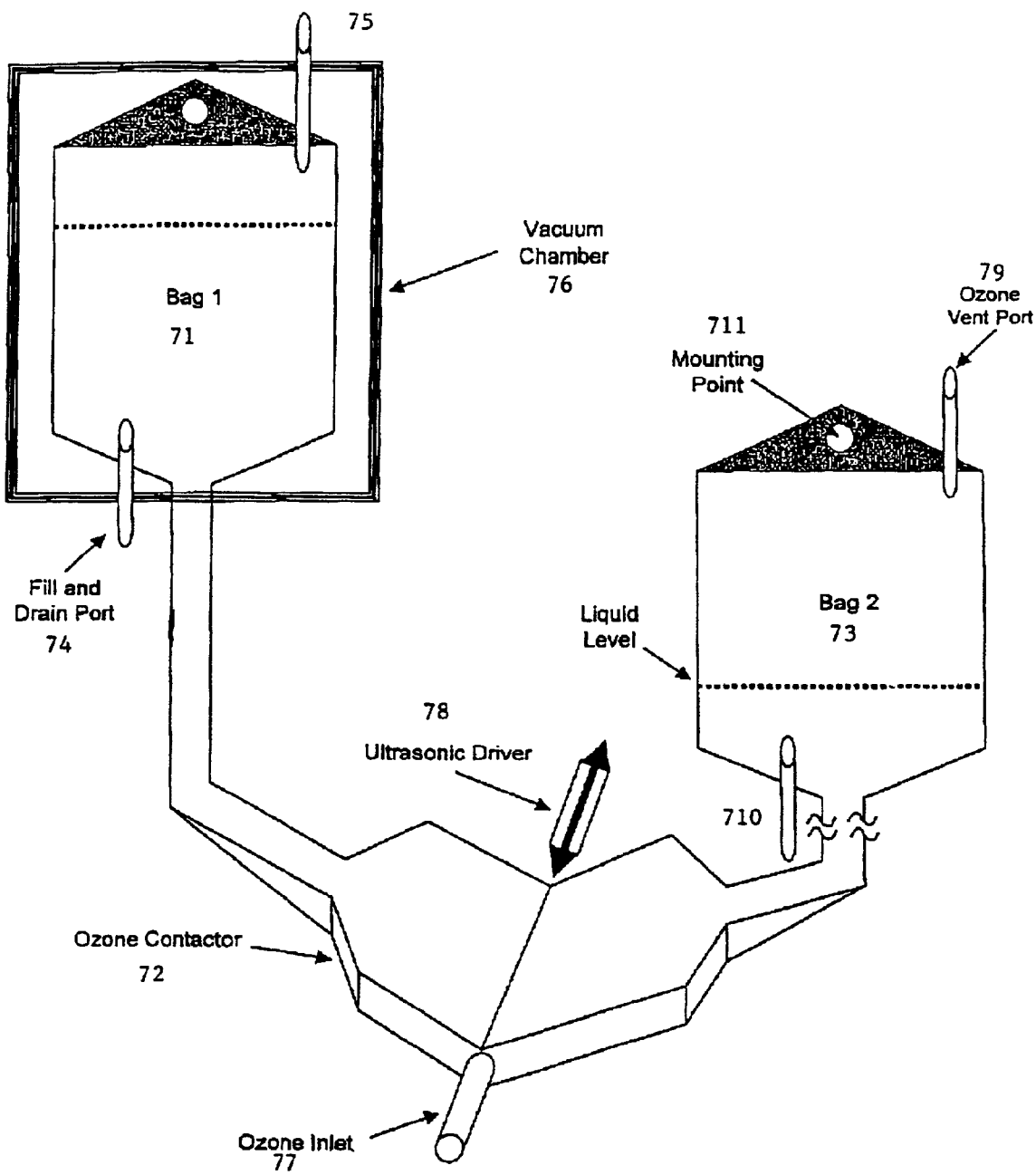
FIG. 7 is a schematic representation of an ozone contactor according to the present invention.

FIG. 7 shows a preferred embodiment of the apparatus of the twenty-fifth and twenty-sixth main embodiments, which is useful for carrying out the methods of the thirteenth through sixteenth main embodiments. A portion of FIG. 7 also corresponds to a preferred embodiment of the contactor of the twenty-eighth main embodiment. In FIG. 7, the fluid passes from bag 1, 71, through ozone contactor, 72, to bag 2, 73. Bag 1, 71 is equipped with a fill and drain port, 74, through which the fluid may be introduced, and an equalizer port, 75, through gas may be introduced to fill the void created by exiting of the fluid from the bag 1, 71. Bag 1, 71, is maintained within a vacuum chamber, 76, to allow for partial degassing, so that the spent ozone, which becomes oxygen, can be replaced by fresh ozone. An alternative approach to the vacuum chamber is to use very high treatment pressures, in excess of 150 psi. In this case, simply releasing the pressure to ambient causes the excess gas to evolve rapidly. A further enhancement for high pressure operation is to surround the fluid bags to be treated by solid blocks inside a pressure chamber. Under this approach, the air compressor is not necessary, because the blocks fill the available residual space in the chamber, thereby preventing the disposable bags from over expanding and subsequent rupture. As the fluid passes through the contactor, 72, it is simultaneously exposed to ozone and ultrasonic energy. The ozone is introduced into the contactor, 72, via an ozone inlet, 77, and into the fluid via a plurality of passage-ways in the inner surfaces (not shown) of the contactor, 72, while the ultrasonic energy is introduced into the fluid via the vibration of the inner surfaces of the contactor, 72, driven by an ultrasonic driver, 78. After passing through the contactor, 72, the fluid enters bag 2, 73, which is equipped with a vent port, 79, to vent the gas displaced by the entering fluid, and a drain port, 710, for draining the fluid. Both bag 1 and bag 2 may be equipped with a mounting ring, 711.

For repeated treatment, such as indicated above for degassing, there are two options. One such option is to progress from one disposable bag to another. This is preferred wherever possible.

Alternatively, the bags could be reused. Of course, such reuse raises the question of residual contamination. Note, however, that all parts of the system are subject to direct ozone gas exposure, and thus are continually being cleaned. Specifically, the surfaces are cleaner than the liquid passing through the system in bulk because when no bulk fluid is present, the surfaces are coated by at most a thin fluid layer, which is readily treated by ozone exposure.

It is also possible to extend this reuse option even further. Specifically, the above description first uses a UV system followed by a separate ozone processor. This is the option that frees up the individual components most rapidly, i.e., one donated unit can be exposed to UV, while a second unit is being treated with ozone. Another approach is to reuse the vacuum degasser bag from the UV unit in the ozone unit, again with enough ozone flow to decontaminate the bag between cycles.

Likewise, it is also possible to make the UV degasification bag from UVC transparent material so that a single bag suffices for both processes. The determining factor here is whether an individual site is more concerned with throughput or disposable expense. For example, a major metropolitan blood collection center would use maximum throughput, while an isolated military field hospital or a hospital in a lesser-developed country would minimize the requirements for disposables. Such considerations can be made only on a site-by-site analysis.

Figure 8:
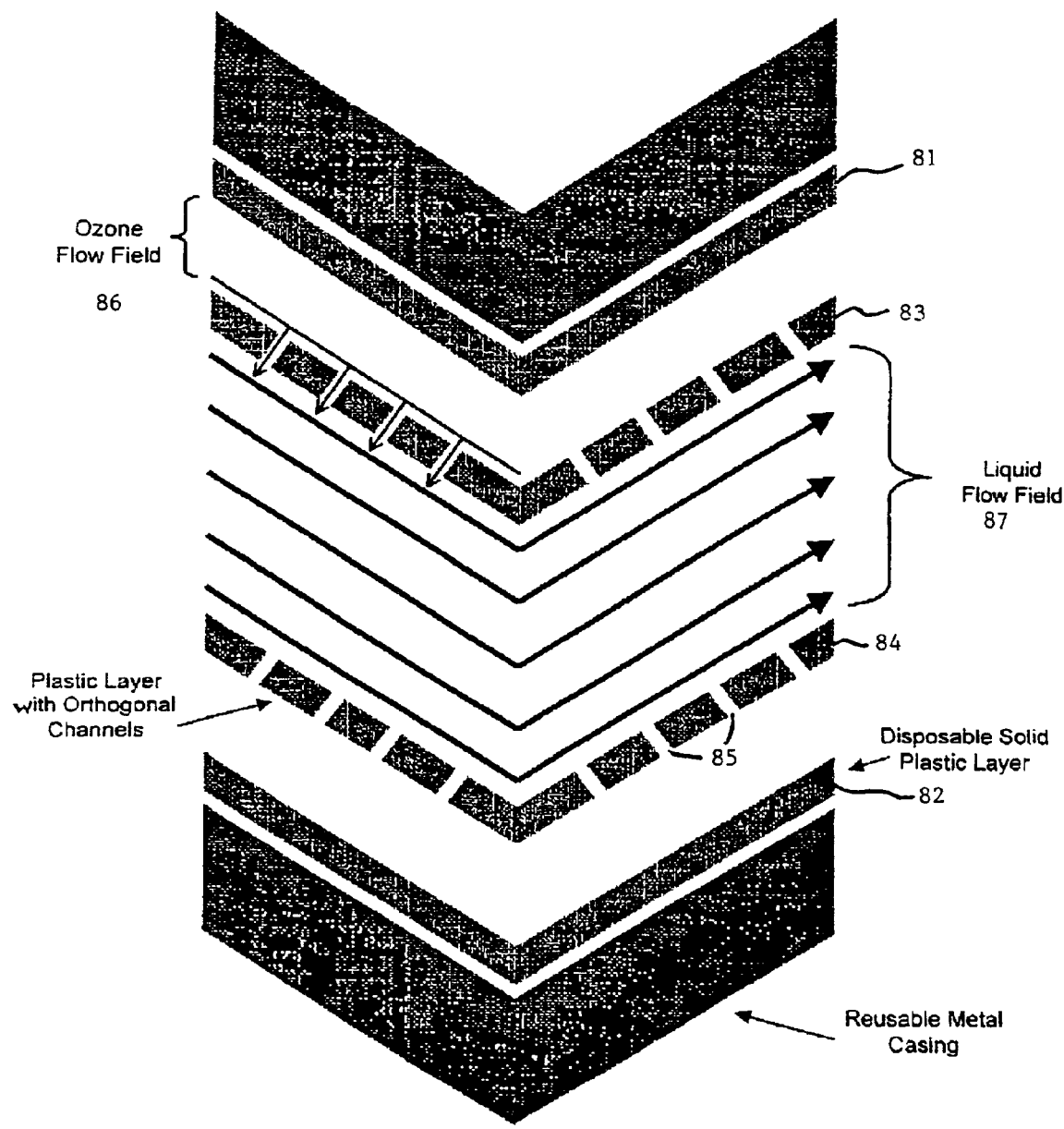
FIG. 8 is a schematic representation of an ozone contactor according to the present invention.

FIG. 8 is a detailed cross-sectional view of the contactor portion of the apparatus shown in FIG. 7. The contactor of FIG. 8 is made up of 4 distinct layers, which form three different flow fields. First there are upper and lower outer layers, 81 and 82, respectively. Second, there are upper and lower inner layers, 83 and 84, respectively, which are perforated by a plurality of channels, 85. It should be noted that the upper and lower inner layers correspond to the substrate(s) described above in the context of the twenty-seventh and twenty-eighth main embodiments, and the channels correspond to the passage-ways described above in the context of the twenty-seventh and twenty-eighth main embodiments. The lumen formed by the upper outer and inner layers, 81 and 83, and by the lower outer and inner layers, 82 and 84, are connected to the ozone inlet, 77, depicted in FIG. 7, and permit the flow of ozone through the contactor, and are referred to as ozone flow fields, 86. The lumen formed by the upper and lower inner layers, 83 and 84, is connected to a source of the fluid such as bag 1, 71, depicted in FIG. 7, and is referred to as the liquid flow field, 87. As the fluid flows through the liquid flow field, 87, ozone is introduced into the fluid through the channels, 85. Simultaneously, ultrasonic energy is introduced into the fluid by the vibration of the upper and lower inner surfaces, 83 and 84 by means of an ultrasound generator (not shown) which is coupled to the upper and lower inner surfaces, 83 and 84.

Figure 9:
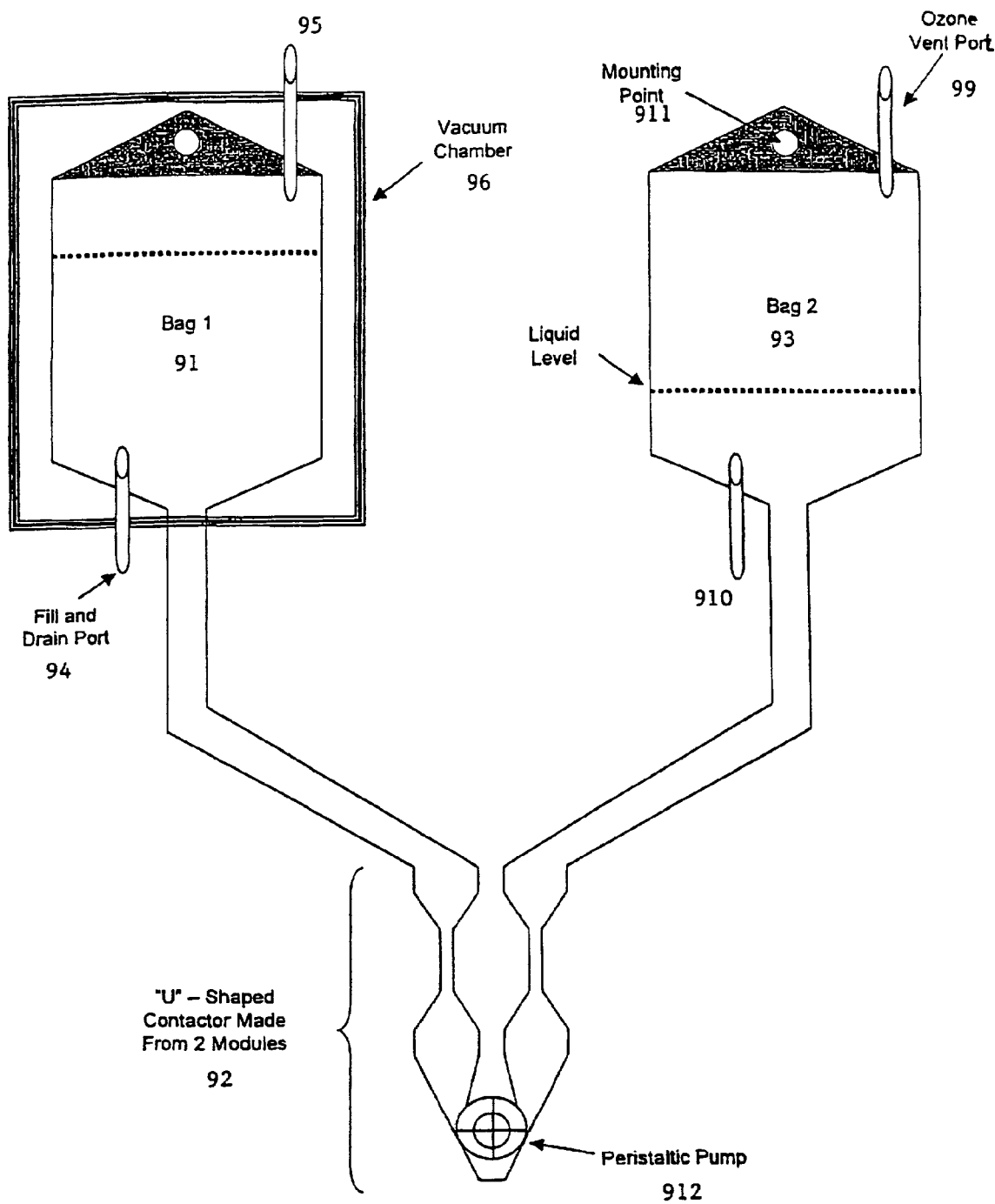
FIG. 9 is a schematic representation of a preferred embodiment of an ozone contactor.

FIG. 9 shows another preferred embodiment of the apparatus of the twenty-fifth and twenty-sixth main embodiments, which is useful for carrying out the methods of the thirteenth through sixteenth main embodiments. A portion of FIG. 9 also corresponds to a preferred embodiment of the contactor of the twenty-ninth main embodiment. In FIG. 9, the fluid passes from bag 1, 91, through ozone contactor, 92, to bag 2, 93. Bag 1, 91 is equipped with a fill and drain port, 94, through which the fluid may be introduced, and an equalizer port, 95, through gas may be introduced to fill the void created by exiting of the fluid from the bag 1, 91. Bag 1, 91, is maintained within a vacuum chamber, 96, to allow for partial degassing, so that the spent ozone, which becomes oxygen, can be replaced by fresh ozone. As the fluid passes through the contactor, 92, it is simultaneously exposed to ozone and ultrasonic energy. The ozone is introduced into the contactor, 92, via an ozone inlet (not shown) and into the fluid via a plurality of passage-ways in the inner surfaces (not shown) of the connector, 92, while the ultrasonic energy is introduced into the fluid via the vibration of the inner surfaces of the connector, 92, driven by an ultrasonic driver (not shown). After passing through the contactor, 92, the fluid enters bag 2, 93, which is equipped with a vent port, 99, to vent the gas displaced by the entering fluid, and a drain port, 910, for draining the fluid. Both bag 1 and bag 2 may be equipped with a mounting ring, 911. The flow of the fluid from bag 1, 91, through the contactor, 92, to bag 2, 93, is assisted by a pump, 912.

Figure 10:
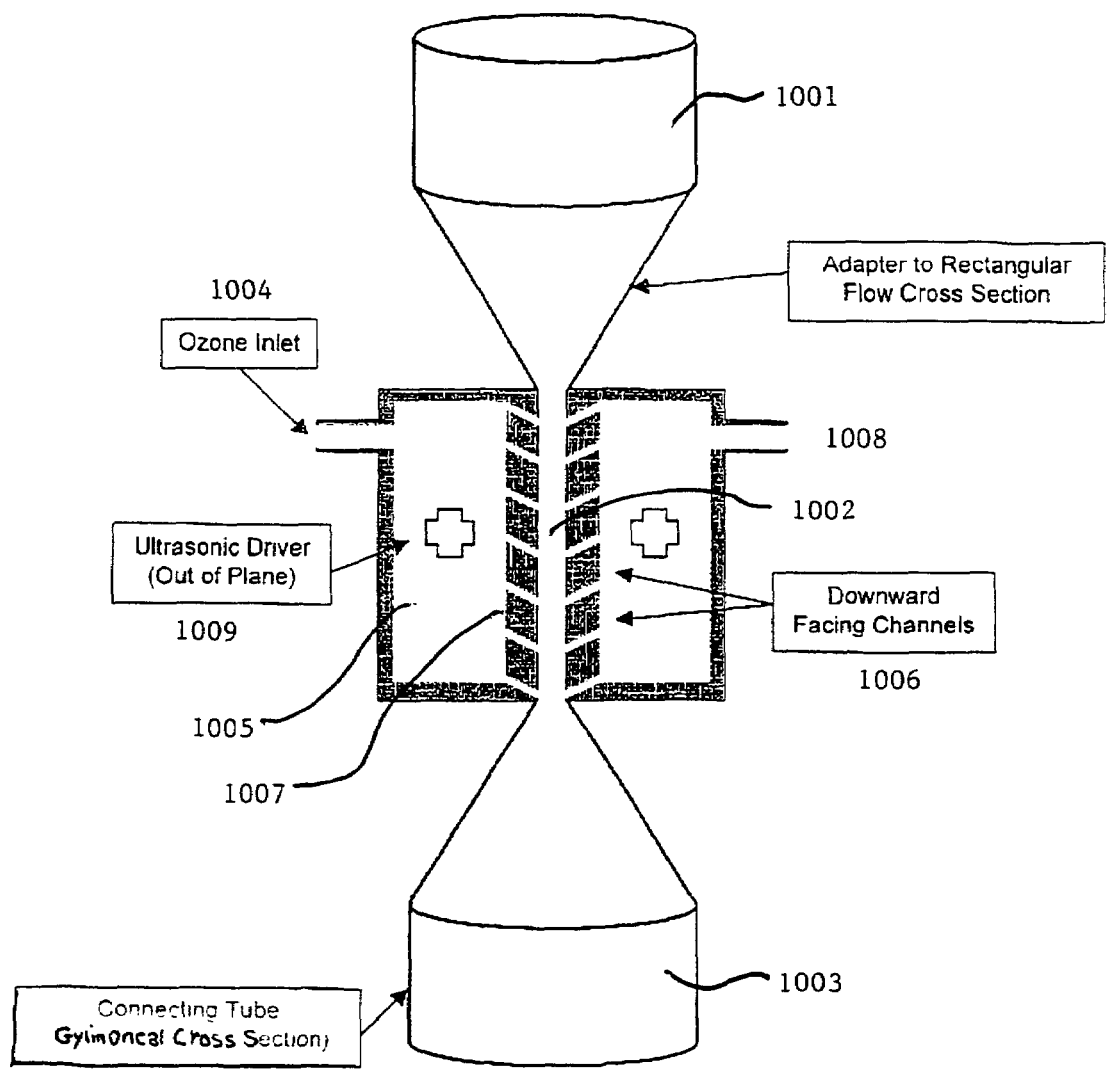
FIG. 10 is a schematic representation of a preferred embodiment of another ozone contactor.

FIG. 10 shows a cross-sectional view of a preferred embodiment of an ozone contactor according to the twenty-ninth main embodiment of the present invention. In FIG. 10, the fluid flows from the inlet, 1001, through the fluid flow field, 1002, to the outlet, 1003. The ozone enters the ozone inlet, 1004, flows through the ozone flow field, 1005, and is introduced into the fluid flow field, 1002, through a plurality of channels, 1006, in the walls forming the fluid flow field, 1007. Any excess ozone exits the ozone flow field, 1005, through an exit, 1008. The walls which form the fluid flow field, 1007, are made to vibrate by being coupled to one or more ultrasonic drivers, 1009.

FIG. 11 shows a cross-sectional view of another ozone contactor which is particularly useful for platelets. In the contactor shown in FIG. 11, the treatment chamber consists of a rectangular or similarly shaped block 1101 with staggered, opposed shelves in the shape of sharp wedges 1102. With the chamber in the horizontal position, the liquid enters a trough or inlet port 1103 along one side. After filling this trough, the chamber is then rotated upwards to about 80 degrees, at which point the fluid flows over the first shelf 1102a towards the opposing wall. Because the shelf does not actually touch the opposing wall, however, the fluid drops down to the next shelf 1102b and the flow then reverses. Meanwhile, ozone is introduced through ports 1104. Note that this arrangement is unlike the above cited patents because the flow reversal thoroughly mixes the material at each step, with the top layer becoming largely the bottom layer and vice versa.

The rotation continues until all of the fluid is emptied from the inlet trough, which occurs at about 90 degrees. The entire arrangement is then rotated back into its original position, and then on to −90 degrees to repeat the process from the opposite direction. During these movements, ozone is continuously fed into one side of the treatment chamber, and spent gas removed from the opposite side. Because the motion of the chamber is thus essentially two reversing half-turns, the gas connections can be conventional flexible hoses. This arrangement thereby saves the costs and installation problems of the sealed bearings, etc., that are required for the continuous rotation units described earlier.

For all of the foregoing embodiments, the last step is to shut down the system and store the product. As noted earlier, small solenoids can be used to tilt the components to drain the quite valuable product as completely as possible. This concept can also be extended to drop the exit side of the "v" of the spray nozzle.

One approach is to collect the product after the last ozone injection pass. This would leave a substantial amount of ozone in the liquid. As it reacts and decays to oxygen, this residual ozone would provide a slight increase in decontamination effectiveness. Also, the resulting oxygen would be quite beneficial to red blood cells and platelets.

Conversely, if the product is to be frozen, the collection should be taken after the product is degassed as thoroughly as possible. This step reduces the formation of gas bubbles (commonly observed as small pockets and streaks in ice cubes) in the frozen product, and thus leads to less product damage during the freezing process.

It is recognized that some variation of the exact conditions and/or parameters of the present methods may be needed to achieve optimum results for certain types of pathogens and infectious agents and fluids. In particular, it is recognized that some of the conditions and/or parameters of the present methods may need to be varied to achieve optimum results for certain types of pathogens and infectious agents, while minimizing plasma protein damage. Such conditions and/or parameters which might need to be varied include the precise intensity and/or frequency of the ultrasonic energy; the precise intensity and/or frequency of the UV, gamma, and/or x-ray radiation; the precise amount of ozone to be mixed with the plasma; the pressure of the ozone; and the precise temperature and/or time of any step.

In recognition of the fact that the precise conditions and/or parameters of the present methods may need to be varied to achieve optimum results for certain types of pathogens and infectious agents, while minimizing damage to the plasma proteins, the following discussion of how to assess and optimize the precise conditions and parameters used in the present methods is provided. The efficacy of any of the present decontamination methods for any given pathogen or infectious agent may be determined by:

(1) determining the concentration or activity of a selected pathogen in a sample of the fluid;

(2) carrying out one of the present decontamination methods on said sample of fluid, to obtain a sample of decontaminated fluid; and (3) determining the concentration or activity of said selected pathogen in said sample of decontaminated fluid.

The parameters of any of the present decontamination methods may be optimized by assessing the efficacy of the method against the pathogen in a first test, then again assessing the efficacy of the method after varying one or more parameters and/or conditions of the method, and then comparing the results of the two tests. Of course, it may be necessary to compare the results of more than two tests to fully optimize any one condition or parameter. Accordingly, it may be preferable to carry out a battery of tests to construct a hyper-dimensional matrix of test results.

The amount of damage to a particular fluid (e.g., plasma) protein and the optimization of any of the present methods in regard to the minimization of plasma protein damage may be carried out in the same way, with the exception of determining protein concentration or activity rather than pathogen concentration or activity.

Any such testing on plasma itself, of course, requires plasma. However, unfortunately, the concentrations of plasma proteins vary widely from donor to donor. This is a significant problem because these variations are usually greater than the fractional protein damage caused by the decontamination methods themselves, thus making direct comparisons difficult. For example, the standard reference range for fibrinogen is 200 to 400 mg/dl, but even a relatively poor (in terms of harshness to the plasma proteins) decontamination technique would destroy less than 25% of this protein. As a result, the variation in the plasma proteins from individual unit to individual unit would thus mask the entire range of protein damage.

Accordingly, when assessing the efficacy or optimizing the present decontamination methods for a particular pathogen or infectious agent it is preferred to use a reference plasma obtained by pooling several donations and then extracting multiple units of the same volume. The use of such a reference plasma establishes a common basis for comparison. Pooling also eliminates much testing expense: with a pool, the protein levels can be tested once to establish starting conditions, but for individual units, each starting condition must be tested separately. This pooling technique has proven to be quite successful in earlier work done by the present inventor, in which it was found that the inherently large error in blood testing equipment could be better offset by multiple tests of a single pool, versus repeated tests of single units. It should be noted that this pooling is for assessment and optimization purposes only, i.e., it does not restrict in any way the ability of the present methods to process individual plasma units.

For the purposes of initial assessment and optimization for a particular pathogen, it may be preferred to lower costs by using non-human plasma. In this regard, bovine plasma provides a useful starting point without the cost or handling problems associated with human products. Once the certain parameters, such as flow rates, ultrasound intensities, etc., have thus been optimized for bovine plasma, human plasma may then be used.

Of course, it should be understood that the plasma as obtained from the donor(s) might not contain any detectable amounts of the pathogen or infectious agent of interest. In such cases, a known amount of the pathogen or infectious agent may be added to the plasma.

The next concern is what plasma protein to test. Given the multitude of components in plasma, there are many options, notably Factor VIII, fibrinogen, von Willebrands factor and various immunoglobulins. Of these proteins, fibrinogen is the most appropriate: it is clinically significant, it is commercially valuable, it is easy to test, it is readily damaged by existing decontamination techniques and its widespread use by other investigators provides a means for direct comparisons.

Obviously, handling live human pathogens is expensive and difficult. For this reason, model viruses, which simulate actual human viruses, may be used for experimental decontamination testing. Specifically, their low cost, low risk, and direct applicability to actual pathogens have led to complete industry and regulatory acceptance. Because of these benefits, many test viruses have been isolated and are now in common use. Typical examples of such model viruses include Sindbis and BVDV (Bovine Viral Diarrhea Virus) for human HCV, and duck HBV for human HBV (B. Horowitz, "Virus Inactivation by Solvent/Detergent Treatment and the Manufacture of SD-Plasma," *Vox Sang*, vol. 74, Suppl. 1, pp. 203–206 (1998)).

While these are certainly significant viruses, however, much of the recent interest in the blood industry has focused on human parvovirus B19. From a clinical standpoint, erythema infectiosum or "fifth disease" from parvovirus is mainly a concern during pregnancy, and thus poses much less risk to the general population than hepatitis or AIDS. In terms of the blood industry, parvovirus infection is actually so common that Plas+SD is sold with the claim that the pooled donors effectively contribute antibodies. On the other hand, parvovirus is extremely difficult to eradicate by conventional techniques. The net result is that there is some question within the blood industry about the cost-effectiveness of attacking this particular virus. Within the decontamination discipline, however, parvovirus is of great interest as a test standard because any technique that is effective against such a robust virus would also be extremely effective against lesser pathogens. Accordingly, it may be preferred to use parvovirus, in particular porcine parvovirus (PPV), as the standard test virus for the optimization of the conditions and/or parameters of any one of the present methods.

Having thus selected the plasma and a test virus, the next concern is how to measure the effectiveness of the proposed technology. Fortunately, such measurements are actually quite simple using standard procedures. Specifically, the plasma may be first spiked with the test virus and then split into two fractions. One fraction is then maintained as a control, while the other fraction is subjected to the decontamination methods being assessed or optimized. For statistical analysis, six samples may be taken at each test point. The test results for a given pathogen can be reported in terms of a logarithmic reduction factor.

It should be noted that the logarithmic reduction factor is a quantitative measurement. As such, it can be inserted directly into a standard test matrix. Because ultrasonic effects are nonlinear, this matrix is in turn nonlinear. This matrix can, however, be reduced by standard steepest descent techniques. The result is an optimized system, within the limits of resolution of the test points. For example, given Beer's exponential law of optical absorption, it is anticipated that the logarithmic reduction factor will drop substantially beyond a critical fluid depth. Having thus established this critical value, the residence time can then be optimized by changing the pump rate and/or the dimensions of the treatment chamber.

Although the literature has some limited information on the ability of various proteins to withstand ultrasound, there is unfortunately a great deal of variation in application techniques, heat control, sonifier design, power measurements, etc. For example, power can be measured as the wattage applied to the transducer, or ultrasonic generator, but if the system is not tuned for resonance, the power actually applied to the sample can be much less. The net result is that transferring such results from one case to another is thus quite unreliable. Thus, it may be preferred to use the above-described optimization method to determine to original or factory settings for a particular apparatus design. It may also be preferred to use the above-described optimization method to perform routine calibrations of apparatus. In this regard, it may be preferred to use the amount of dissolved oxygen in the plasma before and after sonification as a measurement of the amount of sonic energy being applied to the plasma by a given apparatus.

It should be recognized that the present methods may not be effective by themselves for the complete removal of all contaminants. Accordingly, it may be desired in certain circumstance to utilize a small amount of quencher in conjunction with those embodiments which involve irradiation. The advantages in the context of the present invention are lower quench concentrations, reduced chemical cost, reduced removal cost, and less bioburden.

It should also be recognized that in addition to using the present combinations of ultrasound and vacuum prior to UV exposure, the present methods may also be used to prepare anaerobic synthesis systems for biotechnology applications. The advantage here is that the processed systems are then be ready for immediate UV and/or ozone treatment.

Other features of the invention will become apparent in the course of the following descriptions of exemplary embodiments, which are given for illustration of the invention and are not intended to be limiting thereof.

EXAMPLES

The following examples are presented only as representative of the equipment and techniques described above. These examples are not intended to limit the scope of the technology, or the materials that can be treated. The following examples describe increasingly more sophisticated experiments, beginning with a basic system, and then progressing towards more specialized devices. In each case, blood products are used, although different blood products are used for different experiments.

In each case, however, the same test virus is used: porcine parvovirus. As described above in embodiment VII, parvovirus is of particular interest because destruction of this small, robust, non-enveloped virus implies destruction of lesser viruses as well. Also as noted in embodiment VII, the porcine form of parvovirus is convenient to handle because it cannot infect humans.

As for sources, porcine parvovirus is quite widespread throughout the agricultural industry, and is thus commonly available. For detailed experimental work, however, a well-defined source is desired, such as the American Type Culture Collection, Manassas, Va., Item number VR-742.

Likewise, because parvovirus is so widespread, many veterinary facilities and schools can analyze it. A particularly well known group, however, is the American BioResearch Laboratories, located in Sevierville, Tenn.

As for test solutions, plasma is particularly useful because it has both heat-tolerant components, notably fibrinogen, and heat-sensitive components, notably Factor VIII. For convenience, bovine plasma can be used instead of human plasma; in any case, porcine plasma should not be used due to the high likelihood of existing antibodies. Although bovine plasma is readily available from slaughterhouses, higher quality material is available from facilities dedicated to the maintenance of healthy donor animals, such as Quad Five, Ryegate, Mont. In addition to plasma, erythrocytes can also be obtained from bovine sources; alternatively, out of date human cells can also be used, following the convention that scarce transfusable materials should not be used for basic experimental purposes. Likewise, human platelets, which have a shelf life of only 5 days, are also available on an out of date basis. All blood banks have such materials, but the largest supplier is the American Red Cross, which has offices nationwide.

Having thus identified the materials and their sources, testing must then be arranged. Because all of the above blood products have significant clinical interest, testing can be preformed readily in any modern hematology laboratory. For example, bovine blood products are routinely analyzed at the University of Georgia Veterinary School in Athens, Ga., while human blood is tested at the Emory University Hospital Hematology Laboratory in Atlanta, Ga.

With such suppliers and support services, a broad range of experiments can be performed. The first such test is a heat-tolerant plasma protein, fibrinogen. This protein is particularly interesting because it is a crucial part of surgical glues, such as Tisseel by Baxter Healthcare, Deerfield, Ill.

Example 1

Heat-tolerant Plasma Protein

This test is designed for a heat tolerant protein, fibrinogen. This test is also designed for a small quantity, on the order of several ml, because this is the volume of material that can be extracted from a single unit of donated plasma. The test procedure is described below.

First, configure the equipment to handle a small, heat-tolerant material. The required system equipment includes a warming component, a small vacuum module, a UVC exposure module, and an ozone treatment module. The disposable is a small, single unit device, consisting of a liner for the heater, a Teflon® bag to serve in both the vacuum chamber and UVC irradiator, a pair of bags for the ozone exposure unit, an ultrasonic ozone contactor, two virus tight filters, and sterile connecting tubing. Load the disposable items and apply vacuum to evacuate the system to 50 mbar.

Next, dilute 1 ml of porcine parvovirus by 10:1 in bovine plasma. For statistical purposes, prepare 6 sets of six samples each. Retain one set as a control. Heat the remainder of the samples to 52° C. to aid in degassing. Remove 1 set at this point to check for heat effects. Next, immediately degas the remaining sets, and remove one set to check for protein damage. Monitor the degassing process with a hydrophone, and record the elapsed process time. Next, expose all but one of the remaining sets to UVC irradiation for 5 minutes at a distance of 10 cm from the lamps, record the total dosage, and remove one set. Expose the remaining two sets (one UVC treated, and one not) to ozone at 3 atmospheres for 15 minutes.

After these experiments are complete, place all samples on ice and transport to blood and virus testing facilities. After testing, analyze samples to determine confidence levels and any statistically significant differences.

Results: Compared to the controls, the heating and degassing alone show no significant differences in viral loading or protein damage. Conversely, the UVC irradiation alone shows a Log 6 reduction in active parvovirus loading; likewise the ozone treatment alone shows a Log 6 reduction in parvovirus. The combined UVC and ozone shows an apparent Log 12 reduction, although at such levels, detection is much more difficult. In all cases, the fibrinogen loss is less than 5%, which is essentially within the limit of error of the measuring equipment.

Example 2

Heat-sensitive Plasma Protein

This test is designed for a heat tolerant protein, Factor VIII, which is known to be quite labile. All of the test conditions are as above, except that no heating is done on the sample prior to degassing. To compensate for this difference, increase the vacuum to 40 mbar, and extend the degassing time as indicated by the hydrophone monitor.

Results: As observed for fibrinogen, the degassing tests show no measurable decontamination or protein damage. Also as observed for fibrinogen, both UVC and ozone show Log 6 reduction in parvovirus, and the combined process shows Log 12, again with the problem of low level detection. Finally, the protein levels are reduced by less than 5%, which is within the limits of the measuring equipment.

Example 3

Batch Plasma

This test is designed to evaluate the system when processing sequential batches of material. The specific material is a single donor unit of plasma. As such, it is larger than the volumes tested above, but smaller than the volumes that would be treated by the continuous flows discussed below in Example 4. To accommodate this volume, the equipment described in the previous example must be changed as follows.

Because the volume to be treated cannot be handled in the small disposables described earlier, larger units, with provisions for transferring the flow from module to module, must be used. First, replace the single use vacuum chamber liner with a multiple use unit, which amounts to using a liner with an inlet and exit for the processed fluid. Next, replace the irradiation bag with a larger unit, and orient this unit upwards as described earlier to ensure proper residence times. Next, replace the ozone treatment bags with larger units. Finally, as an additional test, degas and then ozone saturate the fluid three times.

Results: The individual UVC and ozone cases each yield Log 6 virus reductions, with Log 12 for the combined process. For the repeated ozone exposure, the viral reduction is Log 9. In all cases, the Factor VIII damage is less than 5%.

Example 4

Continuous Flows

This test is designed to evaluate the system when processing a continuous flow of material. The specific material is again plasma, but in this case the large flow corresponds to the treatment of a pool of material for subsequent fractionation. To accommodate this volume, the equipment described in the previous example must be changed as follows.

The major modification is to change the batch flow equipment to continuous flow equipment. Specifically, the major changes are made to the degassing and ozone treatment modules, along with their associated modules; the batch flow UVC module can also be used for continuous flows with only the addition of a flow controller on the feed pump.

For the degassing module, 4 separate steps are used for this experiment. The degassed liquid is then returned to atmospheric pressure across the discharge of a peristaltic pump that is gravity fed from the degassing trays. UVC exposure follows immediately, and then the fluid is exposed to ozone. The residence time in the UVC and ozone modules is about 15 minutes each, with the actual treatment time being continuously varied slightly about this value according to the respective dosage monitors.

Results: The individual UVC and ozone cases each yield Log 6 virus reductions, with Log 12 for the combined process. The Factor VIII damage is less than 5%.

Example 5

Erythrocytes

This test is designed to determine the effect of decontamination on a living cellular structure. The equipment and conditions are essentially as described for Example 1, except for three factors. The first concern is that a much larger illumination chamber (30 cm by 10 cm) is used to treat a larger surface area than required for the relatively transparent fluid used in Example 1; the volumes are nevertheless similar because the erythrocyte chamber is much thinner at about 40 microns. The second difference is that the heating is done only to 45° C., instead of 52° C., because erythrocytes are known to withstand this lower temperature well during hyperthermia treatments, but the higher (52° C.) temperature could compromise their cell membranes. The third concern is that the erythrocytes are exposed to oxygen, or oxygen/ozone, immediately after irradiation because these cells require oxygen to survive. Note that nerve cells in the brain are known to suffer irreversible damage after only 6 minutes without oxygen, but erythrocytes are much more durable. Furthermore, decreasing the temperature immediately after degassing also helps to maintain cellular integrity.

After performing the previously described procedures, the viral test results are Log 6 reduction for both UVC and ozone, while the combined process is about Log 12. Cell damage in such testing is commonly measured by hemolysis. Observing the number of damaged cells immediately after the process indicates gross mechanical damage, while measuring the cell damage 24 hours later indicates the viability of the treated cells (see, G. F. Doebbler, A. W. Rowe and A. P. Rinfret, "Freezing of Mammalian Blood," in *Cryobiology*, Harold T. Meryman (ed.), Academic Press Inc., London, 407, 1966). In this experiment, the treated materials could not be distinguished from the controls, thereby indicating no significant damage.

Example 6

Platelets

This test is designed for the platelet ozone contactor. The equipment and conditions are essentially as described in Example 1 for heated, small volumes, except for three factors. The first difference is the use of a special ozone contactor designed solely for platelets, and shown in FIG. 11. The second difference is that the heating is done only to 22° C., instead of 52° C., because FDA regulations state that platelets must be maintained at 22±2° C. to retain viability. The third factor is that the illumination must be done immediately after degassing, as reported above for erythrocytes, because platelets require oxygen for long term maintenance.

The results of this test are Log 6 reduction of parvovirus during UVC and ozone, and Log 12 for the combined processes. To determine platelet damage, the first test is a simple optical procedure widely used in the platelet industry. This test amounts to simply observing the flow of the platelets in their special oxygen-permeable bag. Normal platelets should sparkle, while damaged platelets often agglomerate, and thus do not sparkle when illuminated. In this experiment, the treated platelets exhibit the same sparkle as shown by the controls. The second test is to determine clotting effectiveness, which is done by forming a clot from the gel and then rupturing it, thereby indicating whether or not the platelets function as necessary. In this experiment, the clots formed from the control are indistinguishable from the clots formed from the treated material, thereby indicating no appreciable damage to the platelets during decontamination.

Summary: The above examples indicate that the new technology inactivates a robust virus to acceptable levels with minimum damage to the materials being treated.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for decontaminating a fluid, comprising treating the fluid with ultrasonic energy, while contacting the fluid with a vacuum, wherein said fluid is a protein-containing biological fluid selected from the group consisting of plasma, serum, saliva and spinal fluid.

2. The method of claim 1, wherein said treating further comprises simultaneously treating, said fluid with at least two different frequencies of ultrasonic energy.

3. The method of claim 1, which further comprises treating said fluid with said ultrasonic energy to obtain a de-oxygenated fluid; and irradiating said de-oxygenated fluid.

4. The method of claim 1, which further comprises treating said fluid with said ultrasonic energy to obtain a de-oxygenated fluid; and contacting said de-oxygenated fluid with ozone.

5. The method of claim 1, which further comprises mixing said fluid with ozone, to obtain an ozone-containing fluid prior to treating said fluid with said ultrasonic energy.

6. The method of claim 1, which further comprises treating said fluid with said ultrasonic energy to obtain a de-oxygenated fluid; contacting said de-oxygenated fluid with ozone to obtain an ozone-containing fluid; and treating said ozone-containing fluid with ultrasonic energy.

7. The method of claim 1, which further comprises treating said fluid with said ultrasonic energy to obtain a de-oxygenated fluid; irradiating said de-oxygenated fluid to obtain an irradiated fluid; and contacting said irradiated fluid with ozone to obtain an ozone-containing fluid.

8. The method of claim 1, which further comprises treating said fluid with said ultrasonic energy to obtain a de-oxygenated fluid; irradiating said de-oxygenated fluid to obtain an irradiated fluid; contacting said irradiated fluid with ozone to obtain an ozone-containing fluid; and treating said ozone-containing fluid with ultrasonic energy.

9. A method for decontaminating a fluid, comprising a step for the treatment of a fluid with ultrasonic energy, while contacting said fluid with a vacuum, wherein said fluid is a protein-containing biological fluid selected from the group consisting of plasma, serum, saliva and spinal fluid.

10. The method of claim 9, wherein said step for the treatment of said fluid further comprises simultaneous treatment of said fluid with at least two different frequencies of ultrasonic energy.

11. The method of claim 9, wherein said step for the treatment of said fluid with ultrasonic energy produces a de-oxygenated fluid; and further comprising a step for the irradiation of said de-oxygenated fluid.

12. The method of claim 9, wherein said step for the treatment of said fluid with ultrasonic energy produces a de-oxygenated fluid; and further comprising a step for treatment of said de-oxygenated fluid with ozone.

13. The method of claim 9, which further comprises a step for mixing said fluid with ozone to obtain an ozone-containing fluid prior to said step for the treatment of said ozone-containing fluid with ultrasonic energy.

14. The method of claim 9, wherein said step for the treatment of said fluid with ultrasonic energy produces a de-oxygenated fluid; the method further comprising a step for the treatment of said de-oxygenated fluid with ozone to obtain an ozone-containing fluid; and a step for the treatment of said ozone-containing fluid with ultrasonic energy.

15. The method of claim 9, wherein said step for the treatment of said fluid with ultrasonic energy produces a de-oxygenated fluid; the method further comprising a step for the irradiation of said de-oxygenated fluid to obtain an irradiated fluid; and a step for the treatment of said irradiated fluid with ozone to obtain an ozone-containing fluid.

16. The method of claim 9, wherein said step for the treatment of said fluid with ultrasonic energy produces a de-oxygenated fluid; the method further comprising a step for the irradiation of said de-oxygenated fluid to obtain an irradiated fluid; a step for the treatment of said irradiated fluid with ozone to obtain an ozone-containing fluid; and a step for the treatment of said ozone-containing fluid with ultrasonic energy.

* * * * *